(12) United States Patent
Ponath et al.

(10) Patent No.: US 7,402,410 B2
(45) Date of Patent: Jul. 22, 2008

(54) HUMANIZED IMMUNOGLOBULIN REACTIVE WITH α4β7 INTEGRIN

(75) Inventors: Paul D. Ponath, Boston, MA (US); Douglas J. Ringler, Revere, MA (US); S. Tarran Jones, Radlett (GB); Walter Newman, Boston, MA (US); José Saldanha, Middlesex (GB); Mary M. Bendig, London (GB)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/511,164

(22) Filed: Aug. 28, 2006

(65) Prior Publication Data
US 2006/0292140 A1 Dec. 28, 2006

Related U.S. Application Data

(62) Division of application No. 08/700,737, filed on Aug. 15, 1996, now Pat. No. 7,147,851.

(51) Int. Cl.
C12N 15/13 (2006.01)
C12N 15/63 (2006.01)
C12N 5/10 (2006.01)
C12P 21/04 (2006.01)

(52) U.S. Cl. .................. 435/69.6; 536/23.53; 435/325; 435/328; 435/320.1

(58) Field of Classification Search .................. None
See application file for complete search history.

(56) References Cited

U.S. PATENT DOCUMENTS

| | | | |
|---|---|---|---|
| 4,816,397 A | 3/1989 | Boss et al. |
| 4,816,567 A | 3/1989 | Cabilly et al. |
| 5,225,539 A | 7/1993 | Winter |
| 5,258,498 A | 11/1993 | Huston et al. |
| 5,403,919 A | 4/1995 | Butcher |
| 5,530,101 A | 6/1996 | Queen et al. |
| 5,538,724 A | 7/1996 | Butcher et al. |
| 5,558,864 A | 9/1996 | Bendig et al. |
| 5,585,089 A | 12/1996 | Queen et al. |
| 5,624,821 A | 4/1997 | Winter et al. |
| 5,648,260 A | 7/1997 | Winter et al. |
| 5,665,595 A | 9/1997 | Petell et al. |
| 5,693,761 A | 12/1997 | Queen et al. |
| 5,693,762 A | 12/1997 | Queen et al. |
| 5,821,337 A | 10/1998 | Carter et al. |
| 5,840,299 A | 11/1998 | Bendig et al. |
| 5,859,205 A | 1/1999 | Adair et al. |
| 5,871,734 A | 2/1999 | Lobb et al. |
| 5,888,507 A | 3/1999 | Burkly |
| 5,932,214 A | 8/1999 | Lobb et al. |
| 6,551,593 B1 | 4/2003 | Ringler et al. |

FOREIGN PATENT DOCUMENTS

| | | | |
|---|---|---|---|
| EP | 0 239 400 A2 | 9/1987 |
| EP | 0 303 463 B1 | 11/1994 |
| GB | 2209757 B | 10/1990 |
| JP | 63 03990 | 11/1994 |
| WO | WO 86/01533 | 3/1986 |
| WO | WO 88/07089 A1 | 9/1988 |
| WO | WO 89/07142 A1 | 8/1989 |
| WO | WO 90/07321 | 7/1990 |
| WO | WO 90/07861 | 7/1990 |
| WO | WO 91/03252 | 3/1991 |
| WO | WO 91/09967 | 7/1991 |
| WO | WO 92/11018 | * 7/1992 |
| WO | WO 93/02191 | 2/1993 |
| WO | WO 93/15764 | 8/1993 |
| WO | WO 94/12214 | 6/1994 |
| WO | WO 94/13312 | 6/1994 |
| WO | WO 94/16094 | 7/1994 |
| WO | WO 94/17828 | 8/1994 |
| WO | WO 94/29351 | 12/1994 |
| WO | WO 95/19790 | 7/1995 |
| WO | WO 97/18838 | 5/1997 |
| WO | WO 98/06248 | * 2/1998 |
| WO | WO 88/07089 | 9/1998 |

OTHER PUBLICATIONS

Webster's II New Riverside University Dictionary, The Riverside Publishing Company, 1988, p. 755.*

Mountain, A. and Adair, J.R., "Engineering Antibodies for Therapy," *Biotechnol. Genet. Eng. Rev.*, 10:1-142 (1992).

(Continued)

*Primary Examiner*—Ron Schwadron
(74) *Attorney, Agent, or Firm*—Hamilton, Brook, Smith & Reynolds, P.C.

(57) ABSTRACT

The present invention relates to isolated nucleic acids encoding humanized immunoglobulins having binding specificity for α4β7 integrin, isolated nucleic acids encoding a humanized immunoglobulin heavy chain and isolated nucleic acids encoding a humanized light chain having binding specificity for α4β7 integrin. The invention also relates to expression vectors and host cells comprising a nucleotide sequence which encodes a humanized immunoglobulin or antigen-binding fragment thereof having binding specificity for α4β7. The invention further relates to methods of preparing a humanized immunoglobulin, humanized immunoglobulin heavy chain and humanized immunoglobulin light chain that has binding specificity for α4β7 integrin.

23 Claims, 20 Drawing Sheets

OTHER PUBLICATIONS

Woodside, D.G., et al., "Specific Inhibition of T Lymphocyte Coactivation by Triggering Integrin β1 Reveals Convergence of β1, β2, and β7 Signaling Pathways," *J. Immunol.*, 157:700-706 (1996).

van der Voort, R., et al., "Paracrine Regulation of Germinal Center B Cell Adhesion Through the c-Met-Hepatocyte Growth Factor/Scatter Factor Pathway," *J. Exp. Med.*, 185(12):2121-2131 (1997).

Rott, L.S., et al., "Expression of Mucosal Homing Receptor α4β7 by Circulating CD4+ Cells with Memory for Intestinal Rotavirus," *J. Clin. Invest.*, 100(5):1204-1208 (1997).

Lobb, R.R., et al., "The Role of α4 Integrins in Lung Pathophysiology," *Eur. Respir. J.*, 9 (Supp 22):104s-108s (1996).

Goldenberg, D.M., "New Developments in Monoclonal Antibodies for Cancer Detection and Therapy," *CA Cancer J. Clin.*, 44:43-64 (1994).

Owens, R.J. and Young, R.J., "The Genetic Engineering of Monoclonal Antibodies," *J. Immunol. Methods*, 168(2):149-165 (1994).

Lazarovits, A.I. and Karsh, J., "α4β7 Integrin in Rhematoid Arthritis," In *Leucocyte Typing V—White Cell Differentiation Antigens*, S.F. Schlossman, et al., eds., (Oxford: Oxford University), pp. 1686-1687 (1995).

Lazarovits, A.I., et al., "Lymphocyte Activation Antigens—I. A Monoclonal Antibody, Anti-Act 1, Defines a New Late Lymphocyte Activation Antigen," *J. Immunol.*, 133:1857-1862 (1984).

Erle, D.J., et al., "Expression and Function of the MAdCAM-1 Receptor, Integrin α4β7, on Human Leukocytes," *J. Immunol.*, 153:517-528 (1994).

Postigo, A.A., et al., "α4β7 Integrin Mediates B Cell Binding to Fibronectin and Vascular Cell Adhesion Molecule-1," *J. Immunol.*, 151:2471-2483 (1993).

Lazarovits, A.I. and Karsh, J., "Differential Expression in Rheumatoid Synovium and Synovial Fluid of α4β7 Integrin—A Novel Receptor for Fibronectin and Vascular Cell Adhesion Molecule-1," *J. Immunol.*, 151:6482-6489 (1993).

Schweighoffer, T., et al., "Selective Expression of Integrin α4β7 on a Subset of Human CD4+ Memory T Cells with Hallmarks of Gut-Trophism," *J. Immunol.*, 151:717-729 (1993).

Riechmann, L., et al., "Reshaping Human Antibodies for Therapy," *Nature*, 332:323-327 (1988).

Bendig, M.M., "Humanization of Rodent Monoclonal Antibodies by CDR Grafting," *Methods: A Companion to Methods of Enzymology*, 8:83-93 (1995).

Page, M.J., and Sydenham, M.A., "High Level Expression of the Humanized Monoclonal Antibody Campath-1H in Chinese Hamster Ovary Cells," *Bio/Technol*, 9:64-68 (1991).

Bednarczyk, J.L., et al., "Identification of a Combinatorial Epitope Expressed by the Integrin α4β7 Heterodimer Involved in the Regulation of Cell Adhesion," *J. Biol. Chem.*, 269:8348-8354 (1994).

Yacyshyn, B.R., et al., "Crohn's Disease, Ulcerative Colitis, and Normal Intestinal Lymphocytes Express Integrins in Dissimilar Patterns," *Gastroenterol.*, 107:1364-1371 (1994).

Pals, S.T., et al., "Expression of the Mucosal Homing Receptor α4β7 in Malignant Lymphomatous Polyposis of the Intestine," *Gastroenterol.*, 107:1519-1523 (1994).

Teague, T.K., et al., "Integrin α4β7 Co-Stimulation of Human Peripheral Blood T Cell Proliferation," *Cell Adhesion Comm.*, 2:539-547 (1994).

Tiisala, S., et al., "αEβ7 and α4β7 Integrins Associated with Intraepithelial and Mucosal Homing, are Expressed on Macrophages," *Eur. J. Immunol.*, 25:411-417 (1995).

Wan, H.C., et al., "Expression of α4β7 Integrin on Eosinophils and Modulation of α4-Integrin-Mediated Eosinophil Adhesion via CD4," *Int. Arch. Allergy Immunol.*, 107:343-344 (1995).

Berg, E.L., et al., "L-Selectin-Mediated Lymphocyte Rolling on MAdCAM-1," *Nature*, 366:695-698 (1993).

Berlin, C., et al., "α4 Integrins Mediate Lymphocyte Attachment and Rolling under Physiologic Flow," *Cell*, 80:413-422 (1995).

Yang, Y., et al., "Construction and Adhesive Properties of a Soluble MAdCAM-1-Fc Chimera Expressed in a Baculovirus System: Phylogenetic Conservation of Receptor-Ligand Interaction," *Scand. J. Immunol.*, 42:235-247 (1995).

Hamann, A., et al., "Role of α4-Integrins in Lymphocyte Homing to Mucosal Tissues In Vivo," *J. Immunol.*, 152:3282-3293 (1994).

Podolsky, D.K., et al., "Attenuation of Colitis in the Cotton-top Tamarin by Anti-α4 Integrin Monoclonal Antibody," *J. Clin. Invest.*, 92:372-380 (1993).

Podolsky, D.K., "Inflammatory Bowel Disease (First of Two Parts)," *N. Eng. J. Med.*, 325(13):928-937 (1991).

Podolsky, D.K., "Inflammatory Bowel Disease (Second of Two Parts)," *N. Eng. J. Med.*, 325(14):1008-1016 (1991).

Springer, T.A., "The Sensation and Regulation of Interactions with the Extracellular Environment: The Cell Biology of Lymphocyte Adhesion Receptors," *Annu. Rev. Cell Biol.*, 6:359-402 (1990).

Picker, L.J. and Butcher, E.C., "Physiological and Molecular Mechanisms of Lymphocyte Homing," *Annu. Rev. Immunol.*, 10:561-591 (1992).

Hynes, R.O., "Integrins: Versatility, Modulation, and Signaling in Cell Adhesion," *Cell*, 69:11-25 (1992).

Berlin, C., et al., "α4β7 Integrin Mediates Lymphocyte Binding to the Mucosal Vascular Addressin MAdCAM-1," *Cell*, 74:185-195 (1993).

Springer, T.A., "Traffic Signals for Lymphocyte Recirculation and Leukocyte Emigration: The Multistep Paradigm," *Cell*, 76:301-314 (1994).

Briskin, M.J., et al., "MAdCAM-1 Has Homology to Immunoglobulin and Mucin-Like Adhesion Receptors and to IgA1," *Nature*, 363:461-463 (1993).

Salmi, M., et al., "Aberrant Binding of Lamina Propria Lymphocytes to Vascular Endothelium in Inflammatory Bowel Diseases," *Gastroenterology*, 106:596-605 (1994).

Silber, A., et al., "Recruitment of Lymphocytes during Cutaneous Delayed Hypersensitivity in Nonhuman Primates is Dependent on E-Selectin and Vascular Cell Adhesion Molecule 1," *J. Clin. Invest.*, 93:1554-1563 (1994).

Salmi, M., et al., "Dual Binding Capacity of Mucosal Immunoblasts to Mucosal and Synovial Endothelium in Humans: Dissection of the Molecular Mechanisms," *J. Exp. Med.*, 181:137-149 (1995).

Andrew, D.P., et al., "Distinct but Overlapping Epitopes Are Involved in α4β7-Mediated Adhesion to Vascular Cell Adhesion Molecule-1, Mucosal Addressin-1, Fibronectin, and Lymphocyte Aggregation," *J. Immunol.*, 153:3847-3861 (1994).

Osband, M.E., and Ross, S., "Problems in the Investigational Study and Clinical Use of Cancer Immunotherapy," *Immunol. Today*, 11(6):103-105 (1990).

Waldmann, T.A., "Monoclonal Antibodies in Diagnosis and Therapy," *Science*, 252:1657-1662 (1991).

Harris, W.J. and Emery, S., "Therapeutic Antibodies-The Coming of Age," *TIBTECH*, 11:42-44 (1993).

Kettleborough, C.A., et al., "Humanization of a Mouse Monoclonal Antibody by CDR-Grafting: The Importance of Framework Residues on Loop Conformation," *Protein Eng.*, 4(7):773-783 (1991).

Briskin, M.J., et al., "Structural Requirements for Mucosal Vascular Addressin Binding to Its Lymphocyte Receptor α4β7," *J. Immunol.*, 156:719-726 (1996).

Yuan, Q., et al., "Cloning and Sequence Analysis of a Novel $\beta_2$-related Integrin Transcript from T Lymphocytes: Homology of Integrin Cysteine-rich Repeats to Domain III of Laminin B Chains," *Int. Immunol.*, 2(11):1097-1108 (1990).

Yuan, Q., et al., "Cloning and Sequence Analysis of a Novel β2-related Integrin Transcript from T Lymphocytes: Homology of Integrin Cysteine-rich Repeats to Domain III of Laminin B Chains," *Int. Immunol.*, 3(12): 1373-1374 (1991).

Feagan, B.G., et al., "An Ascending Dose Trial of a Humanized $A_4B_7$ Antibody in Ulcerative Colitis (UC)," *Gastroenterol.* 118(4):A874. (Abstract No. 4851), (2000).

Gorman, S.D., et al., "Humanisation of Monoclonal Antibodies for Therapy," *Sem. Immunol.*, 2(6):457-466 (1990).

O'Kennedy, R., et al., "Antibody Engineering: An Overview," *Essays Biochem.*, 26:59-75 (1991).

Winter G., et al., "Humanized Antibodies," *Immunol. Today*, 14(6): 243-246 (1993).

Feagan, B.G., et al., "Treatment of Ulcerative Colitis with a Humanized Antibody to the α4β7 Integrin," *N. Eng. J. Med.*, 352(24):2499-2507 (2005).

Shaw, D.R., et al., "Mouse/Human Chimeric Antibodies to a Tumor-Associated Antigen: Biologic Activity of the Four Human IgG Subclasses," *J. Natl. Cancer Inst.*, 80(19):1553-1559 (1988).

Rudinger, J., "Characteristics of the Amino Acids as Components of a Peptide Hormone Sequence," in *Peptide Hormones*, Parsons, J.A. (Ed.), University Park Press, Baltimore, MD, pp. 1-7, (1976).

Information for Contributions,: *J. Immunol.*, 151(11) (1993).

Springer, T.A., et al., "Leucocyte Typing V White Cell Differentiation Antigens, vol. Two," Oxford University Press, pp. 1443-1456 (1995).

Nieto, M., et al., "Expression of Functionally Active Alpha 4 Beta 1 Integrin by Thymic Epithelial Cells," *Clin. Exp. Immunol*, 106:170-178 (1996).

Mawhorter, S.D., et al., "Identification of Surface Molecules Associated with Physiologic Activation of Eosinophils. Application of Whole-blood Flow Cytometry to Eosinophils," *J. Immunol.*, 156:4851-4858 (1996).

Yuan, Q., et al., "Human Peripheral Blood Eosinophils Express a Functional c-*kit* Receptor for Stem Cell Factor that Stimulates Very Late Antigen 4 (VLA-4)-mediated Cell Adhesion to Fibronectin and Vascular Cell Adhesion Molecule 1 (VCAM-1)," *J. Exp. Med.*, 186:313-323 (1997).

Schulz, O., et al., "Proteolytic Cleavage of CD25, the α Subunit of the Human T Cell Interleukin 2 Receptor, by Der p 1, a Major Mite Allergen with Cysteine Protease Activity," *J. Exp. Med.*, 187:271-275 (1998).

Pritsch, O., et al., "Can Immunoglobulin $C_H1$ Constant Region Domain Modulate Antigen Binding Affinity of Antibodies?," *J. Clin. Invest.*, 98:2235-2243 (1996).

Rudikoff, S., et al., "Single Amino Acid Substitution Altering Antigen-binding Specificity," *Proc. Natl. Acad. Sci. USA*, 79:1979-1983 (1982).

* cited by examiner

Sequence Range: 1 to 494

5' primer region

```
         10              20              30              40              50
          *               *               *               *               *
TTACKRGWMK WC ATG RRA TGS ASC TRK RTC ATY YTC TTC TTG GTA TCA ACA
           M   X   X   X   X   X   I   X   F   L   V   S   T>
         60              70              80  FW1         90
          *               *               *               *               *
GCT ACA AGT GTC CAC TCC CAG GTC CAA CTG CAG CAG CCT GGG GCT GAG
 A   T   S   V   H   S   Q   V   Q   L   Q   Q   P   G   A   E>
                         ↑ Signal peptide cleavage site
100         110         120         130         140
 *           *           *           *           *           *
CTT GTG AAG CCT GGG ACT TCA GTG AAG CTG TCC TGC AAG GGT TAT GGC
 L   V   K   P   G   T   S   V   K   L   S   C   K   G   Y   G>

150         160    CDR1 170         180  FW2    190
 *           *           *           *           *           *
TAC ACC TTC ACC AGC TAC TGG ATG CAC TGG GTG AAG CAG AGG CCT GGA
 Y   T   F   T   S   Y   W   M   H   W   V   K   Q   R   P   G>

200         210         220 CDR2   230         240
          *           *           *           *           *           *
CAA GGC CTT GAG TGG ATC GGA GAG ATT GAT CCT TCT GAG AGT AAT ACT
 Q   G   L   E   W   I   G   E   I   D   P   S   E   S   N   T>

250         260         270    FW3    280         290
          *           *           *           *           *           *
AAC TAC AAT CAA AAA TTC AAG GGC AAG GCC ACA TTG ACT GTA GAC ATT
 N   Y   N   Q   K   F   K   G   K   A   T   L   T   V   D   I>

300         310         320         330
          *           *           *           *           *
TCC TCC AGC ACA GCC TAC ATG CAG CTC AGC AGC CTG ACA TCT GAG GAC
 S   S   S   T   A   Y   M   Q   L   S   S   L   T   S   E   D>

340      * FW3 *      350         360         370    * CDR3 *   380
          *                           *           *                       *
TCT GCG GTC TAC TAT TGT GCA AGA GGG GGT TAC GAC GGA TGG GAC TAT
 S   A   V   Y   Y   C   A   R   G   G   Y   D   G   W   D   Y>

390         400 FW4     410         420         430        C_H
 *           *           *           *           *           *           *
GCT ATT GAC TAC TGG GGT CAA GGC ACC TCA GTC ACC GTC TCC TCA GCC
 A   I   D   Y   W   G   Q   G   T   S   V   T   V   S   S   A>

440         450         460         470         480         490
          *           *           *           *           *           *
AAA ACG ACA CCRYCN CSYKTMTMYC YYSBDNNCCC YKGRWSCYTG GNNGAAGCTT
 K   T   T>
                                                3' primer region
GGGA
```

FIG. 1

Sequence Range: 1 to 428

```
              10          20          30          40          50
     .     *      .     *      .     *      .     *      .     *
TTACTTGACG ACTCGGG ATG GGA TGG AGC TAT ATC ATC TTC TTC TTG GTA TCA
                    M   G   W   S   Y   I   I   F   F   L   V   S>

60          70          80          90          100
     *      .     *      .     *      .     *      .     *
ACA GCT ACA AGT GTC CAC TCC CAG GTC CAA CTG CAG CAG CCT GGG GCT
 T   A   T   S   V   H   S   Q   V   Q   L   Q   Q   P   G   A>

110         120         130         140
     .     *      .     *      .     *      .     *      .
GAG CTT GTG AAG CCT GGG ACT TCA GTG AAG CTG TCC TGC AAG GGT TAT
 E   L   V   K   P   G   T   S   V   K   L   S   C   K   G   Y>

150         160         170         180         190
  .     *      .     *      .     *      .     *      .     *
GGC TAC ACC TTC ACC AGC TAC TGG ATG CAC TGG GTG AAG CAG AGG CCT
 G   Y   T   F   T   S   Y   W   M   H   W   V   K   Q   R   P>

200         210         220         230         240
  *      .     *     *      .     *      .     *      .     *
GGA CAA GGC CTT GAG TGG ATC GGA GAG ATT GAT CCT TCT GAG AGT AAT
 G   Q   G   L   E   W   I   G   E   I   D   P   S   E   S   N>

250         260         270         280         290
     .     *      .     *      .     *      .     *      .     *
ACT AAC TAC AAT CAA AAA TTC AAG GGC AAG GCC ACA TTG ACT GTA GAC
 T   N   Y   N   Q   K   F   K   G   K   A   T   L   T   V   D>

300         310         320         330         340
     .     *      .     *      .     *      .     *      .     *
ATT TCC TCC AGC ACA GCC TAC ATG CAG CTC AGC AGC CTG ACA TCT GAG
 I   S   S   S   T   A   Y   M   Q   L   S   S   L   T   S   E>

350         360         370         380
     .     *      .     *      .     *      .     *      .
GAC TCT GCG GTC TAC TAT TGT GCA AGA GGG GGT TAC GAC GGA TGG GAC
 D   S   A   V   Y   Y   C   A   R   G   G   Y   D   G   W   D>

390         400         410         420
  *      .     *      .     *      .     *      .
TAT GCT ATT GAC TAC TGG GGT CAA GGC ACA TCA GTC ACC
 Y   A   I   D   Y   W   G   Q   G   T   S   V   T>
```

FIG. 2

Sequence Range: 1 to 535

5' primer region

```
          10           20            30            40           50
  *|   *    *     *     *    *     *     *     *   |*    *
CGATTACTAG TCGAC ATG AAG TTG CCT GTT AGG CTG TTG GTG CTT CTG TTG
                 M   K   L   P   V   R   L   L   V   L   L   L
                                        Signal peptide cleavage site
              60           70       |      80           90
       *    *    *    *    *|   *    *    *    *    *
      TTC TGG ATT CCT GTT TCC GGA GGT↓GAT GTT GTG GTG ACT CAA ACT CCA
       F   W   I   P   V   S   G   G   D   V   V   V   T   Q   T   P>

100          110          120          130          140
  *    *    *    *    *    *    *    *    *    *
     CTC TCC CTG CCT GTC AGC TTT GGA GAT CAA GTT TCT ATC TCT TGC AGG
      L   S   L   P   V   S   F   G   D   Q   V   S   I   S   C   R>

150          160          170          180          190
  *    *    *    *    *    *    *    *    *    *
    TCT AGT CAG AGT CTT GCA AAG AGT TAT GGG AAC ACC TAT TTG TCT TGG
     S   S   Q   S   L   A   K   S   Y   G   N   T   Y   L   S   W>

200          210          220          230          240
       *    *    *    *    *    *    *    *    *    *
      TAC CTG CAC AAG CCT GGC CAG TCT CCA CAG CTC CTC ATC TAT GGG ATT
       Y   L   H   K   P   G   Q   S   P   Q   L   L   I   Y   G   I>

250          260          270          280          290
            *    *    *    *    *    *    *    *    *    *
           TCC AAC AGA TTT TCT GGG GTG CCA GAC AGG TTC AGT GGC AGT GGT TCA
            S   N   R   F   S   G   V   P   D   R   F   S   G   S   G   S>

300          310          320          330
       *    *    *    *    *    *    *    *    *
      GGG ACA GAT TTC ACA CTC AAG ATC AGC ACA ATA AAG CCT GAG GAC TTG
       G   T   D   F   T   L   K   I   S   T   I   K   P   E   D   L>
                                                         JK2 (joining
340          350          360          370          380
  *    *    *    *    *    *    *    *   |*    *
 GGA ATG TAT TAC TGC TTA CAA GGT ACA CAT CAG CCG TAC ACG TTC GGA
  G   M   Y   Y   C   L   Q   G   T   H   Q   P   Y   T   F   G>

390     region)  400          410   →C_L    420       Kas I    430
  *    *    *    *    *    *|   *    *  | G  *  G |   *    *
 GGG GGG ACC AAG CTG GAA ATA AAA CGG GCT GAT GCT GCA CCA ACT GTA
  G   G   T   K   L   E   I   K   R   A   D   A   A   P   T   V>

3' primer region
   440          450          460           470          480          490
  |*    *    *    *    *    *|   *    *    *    *    *
 TCCAT CTTCCCACCA TCCAGTAAGC TTGGGAATCC ATATGACTAG TAGATCCTCT 500          510          520          530
           *    *    *    *    *    *    *    *    *
      AGAGTCGACC TGCAGGCATG CAAGCTTCCC TATAGTGAGT CGTAT
```

FIG. 3

Percent similarity: 82.143    Percent Identity: 71.429

```
Act-1.vl   1  DVVVTQTPLSLPVSFGDQVSISC [ RSSQSLAKSYGNTYLS ] WYLHKPGQSPQ   50
                 ••  ••••                  ••        ••         ••••
GM607'CL   1  DIVMTQSPLSLPVTPGEPASISC [ RSSQSLLHSNGYNYLD ] WYLQKPGQSPQ   50
                                        [     CDR 1        ]

Act-1.vl  51  LLIY [ GISNRFS ] GVPDRFSGSGSGTDFTLKISTIKPEDLGMYYC [ LQGTHQP  100
                    [          ••]                ••••  ••••          ••••
GM607'CL  51  LLIY [ LGSNRAS ] GVPDRFSGSGSGTDFTLKISRVEAEDVGVYYC [ MQALQTP  100
                    [  CDR 2  ]                                 [  CDR 3

Act-1.vl 101  YT ] FGGGTKLEIK   112
                   ••   ••
GM607'CL 101  QT ] FGQGTKVEIK   112
             ]
```

FIG. 5

Percent Similarity: 82.353     Percent Identity: 68.067

```
Act-1.vh    1   QVQLQQPGAELVKPGTSVKLSCKGYGYTFT [ SYWMH ] WVKQRPGQGLEWIG [ E    50
                 ••     ••        ••••                ••••
21/28'CL    1   QVQLVQSGAEVKKKPGASVKVSCKASGYTFT [ SYAMH ] WVRQAPGQRLEWMG [ W    50
                                                   [ CDR 1 ]

Act-1.vh   51   IDPSESNTNYNQKFKG ] KATLTVDISSSTAYMQLSSLTSEDSAVYYCAR [ GG   100
                ••••••••••  ••         ••     ••••
21/28'CL   51   INAGNGNTKYSQKFQG ] RVTITRDTSASTAYMELSSLRSEDTAVYYCAR [ GG   100
                     [ CDR 2 ]

Act-1.vh  101   YDGWDYAIDY ] WGQGTSVTVSS                              121
                   ••••••
21/28'CL  101   Y..YGSGSNY ] WGQGTLVTVSS                              119
                  [ CDR 3 ]
```

FIG. 6

```
    ATGAAGTTGCCTGTTAGGCTGTTGGTGCTTCTGTTGTTCTGGATTCCTGTTTCCGGAGGT
1   ------------------------------------------------------------  60
    TACTTCAACGGACAATCCGACAACCACGAAGACAACAAGACCTAAGGACAAAGGCCTCCA
    [M  K  L  P  V  R  L  L  V  L  L  L  F  W  I  P  V  S  G  G]

Signal Peptide

GATGTTGTGGTGACTCAAACTCCACTCTCCCTGCCTGTCAGCTTTGGAGATCAAGTTTCT
61  ------------------------------------------------------------ 120
    CTACAACACCACTGAGTTTGAGGTGAGAGGGACGGACAGTCGAAACCTCTAGTTCAAAGA
    [D  V  V  V  T  Q  T  P  L  S  L  P  V  S  F  G  D  Q  V  S

Framework 1

ATCTCTTGCAGGTCTAGTCAGAGTCTTGCAAAGAGTTATGGGAACACCTATTTGTCTTGG
121   ------------------------------------------------------------ 180
      TAGAGAACGTCCAGATCAGTCTCAGAACGTTTCTCAATACCCTTGTGGATAAACAGAACC
       I  S  C][R  S  S  Q  S  L  A  K  S  Y  G  N  T  Y  L  S][W

CDR 1

TACCTGCACAAGCCTGGCCAGTCTCCACAGCTCCTCATCTATGGGATTTCCAACAGATTT
181   ------------------------------------------------------------ 240
      ATGGACGTGTTCGGACCGGTCAGAGGTGTCGAGGAGTAGATACCCTAAAGGTTGTCTAAA
       Y  L  H  K  P  G  Q  S  P  Q  L  L  I  Y][G  I  S  N  R  F

Framework 2                                    CDR 2

TCTGGGGTGCCAGACAGGTTCAGTGGCAGTGGTTCAGGGACAGATTTCACACTCAAGATC
241   ------------------------------------------------------------ 300
      AGACCCCACGGTCTGTCCAAGTCACCGTCACCAAGTCCCTGTCTAAAGTGTGAGTTCTAG
       S][G  V  P  D  R  F  S  G  S  G  S  G  T  D  F  T  L  K  I

Framework 3

AGCACAATAAAGCCTGAGGACTTGGGAATGTATTACTGCTTACAAGGTACACATCAGCCG
301   ------------------------------------------------------------ 360
      TCGTGTTATTTCGGACTCCTGAACCCTTACATAATGACGAATGTTCCATGTGTAGTCGGC
       S  T  I  K  P  E  D  L  G  M  Y  Y  C][L  Q  G  T  H  Q  P

CDR 3

TACACGTTCGGAGGGGGGACCAAGCTGGAAATAAAA
361   ------------------------------------ 396
      ATGTGCAAGCCTCCCCCCTGGTTCGACCTTTATTTT
       Y  T][F  G  G  G  T  K  L  E  I  K]

Framework 4
```

FIG. 7

```
    GATATTGTGATGACTCAGTCTCCACTCTCCCTGCCCGTCACCCCTGGAGAGCCGGCCTCC
1   ------------------------------------------------------------  60
    CTATAACACTACTGAGTCAGAGGTGAGAGGGACGGGCAGTGGGGACCTCTCGGCCGGAGG
   [D   I   V   M   T   Q   S   P   L   S   L   P   V   T   P   G   E   P   A   S

Framework 1

ATCTCCTGCAGGTCTAGTCAGAGCCTCCTCCATAGTAATGGATCAAACTATTTGGATTGG
61  ------------------------------------------------------------  120
    TAGAGGACGTCCAGATCAGTCTCGGAGGAGGTATCATTACCTAGTTTGATAAACCTAACC
    I   S   C] [R   S   S   Q   S   L   L   H   S   N   G   Y   N   Y   L   D] [W

CDR 1

TACCTGCAGAAGCCAGGGCAGTCTCCACAGCTCCTGATCTATTTGGGTTCTAATCGGGCC
121 ------------------------------------------------------------  180
    ATGGACGTCTTCGGTCCCGTCAGAGGTGTCGAGGACTAGATAAACCCAAGATTAGCCCGG
    Y   L   Q   K   P   G   Q   S   P   Q   L   L   I   Y] [L   G   S   N   R   A

Framework 2                              CDR 2

TCCGGGGTCCCTGACAGGTTCAGTGGCAGTGGATCAGGCACAGATTTTACACTGAAAATC
181 ------------------------------------------------------------  240
    AGGCCCCAGGGACTGTCCAAGTCACCGTCACCTAGTCCGTGTCTAAAATGTGTCTTTTAG
    S] [G   V   P   D   R   F   S   G   S   G   S   G   T   D   F   T   L   K   I

Framework 3

241 AGCAGAGTGGAGGCTGAGGATGTTGGGGTTTATTACTGCATGCAAGCTCTACCAACTCCT
    ------------------------------------------------------------  300
    TCGTCTCACCTCCGACTCCTACAACCCCAAATAATGACGTACGTTCGAGATGGTTGAGGA
     S   R   V   E   A   E   D   V   G   V   Y   Y   C] [M   Q   A   L   Q   T   P

CDR 3

301 CAGACGTTCGGCCAAGGGACCAAGGTGGAAATCAAA
    ------------------------------------  336
    GTCTGCAAGCCGGTTCCCTGGTTCCACCTTTAGTTT
     Q   T] [F   G   Q   G   T   K   V   E   I   K

Framework 4
```

FIG. 8

```
      ATGGGATGGAGCTGTATCATCCTCTTCTTGGTATCAACAGCTACAAGTGTCCACTCCCAG
  1   ------------------------------------------------------------  60
      TACCCTACCTCGACATAGTAGGAGAAGAACCATAGTTGTCGATGTTCACAGGTGAGGGTC
       M  G  W  S  C  I  I  L  F  L  V  S  T  A  T  S  V  H  S][Q

Signal Peptide

GTCCAACTGCAGCAGCCTGGGGCTGAGCTTGTGAAGCCTGGGACTTCAGTGAAGCTGTCC
 61   ------------------------------------------------------------ 120
      CAGGTTGACGTCGTCGGACCCCGACTCGAACACTTCGGACCCTGAAGTCACTTCGACAGG
       V  Q  L  Q  Q  P  G  A  E  L  V  K  P  G  T  S  V  K  L  S

Framework 1

TGCAAGGGTTATGGCTACACCTTCACCAGCTACTGGATGCACTGGGTGAAGCAGAGGCCT
121   ------------------------------------------------------------ 180
      ACGTTCCCAATACCGATGTGGAAGTGGTCGATGACCTACGTGACCCACTTCGTCTCCGGA
       C  K  G  Y  G  Y  T  F  T][S  Y  W  M  H][W  V  K  Q  R  P

CDR 1

GGACAAGGCCTTGAGTGGATCGGAGAGATTGATCCTTCTGAGAGTAATACTAACTACAAT
181   ------------------------------------------------------------ 240
      CCTGTTCCGGAACTCACCTAGCCTCTCTAACTAGGAAGACTCTCATTATGATTGATGTTA
       G  Q  G  L  E  W  I  G][E  I  D  P  S  E  S  N  T  N  Y  N

Framework 2                         CDR 2

CAAAAATTCAAGGGCAAGGCCACATTGACTGTAGACATTTCCTCCAGCACAGCCTACATG
241   ------------------------------------------------------------ 300
      GTTTTTAAGTTCCCGTTCCGGTGTAACTGACATCTGTAAAGGAGGTCGTGTCGGATGTAC
       Q  K  F  K  G][K  A  T  L  T  V  D  I  S  S  S  T  A  Y  M

Framework 3

CAGCTCAGCAGCCTGACATCTGAGGACTCTGCGGTCTACTATTGTGCAAGAGGGGGTTAC
301   ------------------------------------------------------------ 360
      GTCGAGTCGTCGGACTGTAGACTCCTGAGACGCCAGATGATAACACGTTCTCCCCCAATG
       Q  L  S  S  L  T  S  E  D  S  A  V  Y  Y  C  A  R][G  G  Y

GACGGATGGGACTATGCTATTGACTACTGGGGTCAAGGCACCTCAGTCACCGTCTCCTCA
361   ------------------------------------------------------------ 420
      CTGCCTACCCTGATACGATAACTGATGACCCCAGTTCCGTGGAGTCAGTGGCAGAGGAGT
       D  G  W  D  Y  A  I  D  Y][W  G  Q  G  T  S  V  T  V  S  S]

CDR 3                           Framework 4
```

FIG. 9

```
      ATGGAGTTTGGGCTGAGCTGGCTTTTTCTTGTGGCTATTTTAAAAGGTGTCCAGTGTCAG
  1   ------------------------------------------------------------  60
      TACCTCAAACCCGACTCGACCGAAAAAGAACACCGATAAAATTTTCCACAGGTCACAGTC
      [M   E   F   G   L   S   W   L   F   L   V   A   I   L   K   G   V   Q   C][Q
                                    Signal peptide GTGCAGCTTGTGCAGTCTGGGGCTGAGGTGAAGAAGCCTGGGGCCTCAGTGAAGGTTTCC
 61   ------------------------------------------------------------ 120
      CACGTCGAACACGTCAGACCCCGACTCCACTTCTTCGGACCCCGGAGTCACTTCCAAAGG
       V   Q   L   V   Q   S   G   A   E   V   K   K   P   G   A   S   V   K   V   S
                                    Framework 1

TGCAAGGCTTCTGGATACACCTTCACTAGCTATGCTATGCATTGGGTGCGCCAGGCCCCC
121   ------------------------------------------------------------ 180
      ACGTTCCGAAGACCTATGTGGAAGTGATCGATACGATACGTAACCCACGCGGTCCGGGGG
       C   K   A   S   G   Y   T   F   T][S   Y   A   M   H][W   V   R   Q   A   P
                                              CDR 1

GGACAAAGGCTTGAGTGGATGGGATGGATCAACGCTGGCAATGGTAACACAAAATATTCA
181   ------------------------------------------------------------ 240
      CCTGTTTCCGAACTCACCTACCCTACCTAGTTGCGACCGTTACCATTGTGTTTTATAAGT
       G   Q   R   L   E   W   M   G][W   I   N   A   G   N   G   N   T   K   Y   S
            Framework 2                          CDR 2

CAGAAGTTCCAGGGCAGAGTCACCATTACCAGGGACACATCCGCGAGCACAGCCTACATG
241   ------------------------------------------------------------ 300
      GTCTTCAAGGTCCCGTCTCAGTGGTAATGGTCCCTGTGTAGGCGCTCGTGTCGGATGTAC
       Q   K   F   Q   G][R   V   T   I   T   R   D   T   S   A   S   T   A   Y   M

GAGCTGAGCAGCCTGAGATCTGAAGACACGGCTGTGTATTACTGTGCGAGAGGAGGTTAC
301   ------------------------------------------------------------ 360
      CTCGACTCGTCGGACTCTAGACTTCTGTGCCGACACATAATGACACGCTCTCCTCCAATG
       E   L   S   S   L   R   S   E   D   T   A   V   Y   Y   C   A   R][G   G   Y
                                    Framework 3

TATGGTTCGGGGAGCAACTACTGGGGCCAGGGAACCCTGGTCACCGTCTCCTCA
361   ----------------------------------------------------- 414
      ATACCAAGCCCCTCGTTGATGACCCCGGTCCCTTGGGACCAGTGGCAGAGGAGT
       Y   G   S   G   S   N   Y][W   G   Q   G   T   L   V   T   V   S   S]
              CDR 3                         Framework 4
```

FIG. 10

```
           10           20           30           40
    *.     *    *       *    *       *    *       *    *
ATG AAA TGC ACC TGG GTC ATT CTC TTC TTG GTA TCA ACA GCT ACA AGT
 M   K   C   T   W   V   I   L   F   L   V   S   T   A   T   S>
                 ┌─Single peptide cleavage site
50           60           70           80           90
 *    *    * │   *    *│Spe I*   *    *    *    *    *    *
GTC CAC TCC↓CAG GTC CAA CTA GTG CAG TCT GGG GCT GAG GTT AAG AAG
 V   H   S   Q   V   Q│  L   V   Q   S   G   A   E   V   K   K>
                      └─────────
  100          110          120          130          140
 *    *    *    *    *    *    *    *    *    *    *    *
CCT GGG GCT TCA GTG AAG GTG TCC TGC AAG GGT TCT GGC TAC ACC TTC
 P   G   A   S   V   K   V   S   C   K   G   S   G   Y   T   F>
                                                          Xba I
  150          160          170          180          190
 *    *    *    *    *    *    *    *    *    *    │*
ACC AGC TAC TGG ATG CAT TGG GTG AGG CAG GCG CCT GGC CAA CGT CTA
 T   S   Y   W   M   H   W   V   R   Q   A   P   G   Q   R│ L>
     200          210          220          230          240
  *    *    *    *    *    *    *    *    *    *    *    *
GAG TGG ATC GGA GAG ATT GAT CCT TCT GAG AGT AAT ACT AAC TAC AAT
 E   W   I   G   E   I   D   P   S   E   S   N   T   N   Y   N>
          250          260          270          280       Nhe I
  *    *    *    *    *    *    *    *    *    *    *
CAA AAA TTC AAG GGA CGC GTC ACA TTG ACT GTA GAC ATT TCC GCT AGC
 Q   K   F   K   G   R   V   T   L   T   V   D   I   S│  A   S>
  290          300          310          320          330
 *    *    *    *    *    *    *    *    *    *    *    *
ACA GCC TAC ATG GAG CTC AGC AGC CTG AGA TCT GAG GAC ACT GCG GTC
 T   A   Y   M   E   L   S   S   L   R   S   E   D   T   A   V>
  340          350          360          370          380
 *    *    *    *    *    *    *    *    *    *    *
TAC TAT TGT GCA AGA GGG GGT TAC GAC GGA TGG GAC TAT GCT ATT GAC
 Y   Y   C   A   R   G   G   Y   D   G   W   D   Y   A   I   D>
  390          400 BstE II 410           420   constant430
 *    *    *    *    *    *           *    *│    *region *
TAC TGG GGT CAA GGC ACC CTG GTC ACC GTC TCC TCA GCC TCC ACC AAG
 Y   W   G   Q   G   T   L│  V   T│  V   S   S   A   S   T   K>
      440          450          460          470          480
  *    *    *    *    *    *    *    *    *    *    *    *
GGC CCA TCG GTC TTC CCC CTG GCA CCC TCC TCC AAG AGC ACC TCT GGG
 G   P   S   V   F   P   L   A   P   S   S   K   S   T   S   G>
      490          500          510          520
  *    *    *    *    *    *    *    *    *    *    *Age I
GGC ACA GCG GCC CTG GGC TGC CTG GTC AAG GAC TAC TTC CCC GAA CCG
 G   T   A   A   L   G   C   L   V   K   D   Y   F   P   E│  P>
530          540
 *│   *    *
GTG ACG GTG TCG
 V│  T   V   S>
```

FIG. 11

```
              10               20                30              40
         *         *         *         *         *         *         *
ATG AAG TTG CCT GTT AGG CTG TTG GTG CTG CTG TTG TTC TGG ATT CCT
 M   K   L   P   V   R   L   L   V   L   L   L   F   W   I   P>
                         signal peptide cleavage site
  50   BspE I   60                70              80              90
   *    *    *    *    *    *    *    *    *    *    *    *    *
GTT TCC GGA GGT GAT GTT GTG ATG ACT CAA AGT CCA CTC TCC CTG CCT
 V   S   G   G   D   V   V   M   T   Q   S   P   L   S   L   P>

100             110             120             130             140
    *         *         *         *         *         *         *         *
GTC ACC CCT GGA GAA CCA GCT TCT ATC TCT TGC AGG TCT AGT CAG AGT
 V   T   P   G   E   P   A   S   I   S   C   R   S   S   Q   S>

150             160             170         180 Asp 718    190
    *         *         *         *         *         *         *         *
CTT GCA AAG AGT TAT GGG AAC ACC TAT TTG TCT TGG TAC CTG CAG AAG
 L   A   K   S   Y   G   N   T   Y   L   S   W   Y   L   Q   K>

200             210             220             230             240
   *Msc I  *         *         *         *         *         *         *         *
CCT GGC CAG TCT CCA CAG CTC CTC ATC TAT GGG ATT TCC AAC AGA TTT
 P   G   Q   S   P   Q   L   L   I   Y   G   I   S   N   R   F>

250             260             270             280
    *         *         *         *         *         *         *         *
TCT GGG GTG CCA GAC AGG TTC AGT GGC AGT GGT TCA GGG ACA GAT TTC
 S   G   V   P   D   R   F   S   G   S   G   S   G   T   D   F>

290         300 NruI       310             320             330
    *         *         *         *         *         *         *         *
ACA CTC AAG ATC TCG CGA GTA GAG GCT GAG GAC GTG GGA GTG TAT TAC
 T   L   K   I   S   R   V   E   A   E   D   V   G   V   Y   Y>

340             350             360             370             380
    *         *         *         *         *         *         *         *
TGC TTA CAA GGT ACA CAT CAG CCG TAC ACG TTC GGA CAG GGG ACC AAG
 C   L   Q   G   T   H   Q   P   Y   T   F   G   Q   G   T   K>

390             400             410 Kas I
    *         *         *         *         *         *
GTG GAA ATA AAA CGG GCT GAT GCG GCG CC
 V   E   I   K   R   A   D   A   A   P>
```

FIG. 12

LIGHT CHAIN OLIGOS:  DOUBLE STRAND FRAGMENTS

L1  5'- TTT CCG GAG GTG ATG TTG TGA TGA CTC AAA GTC CAC TCT CCC
        TGC CTG TCA CCC CTG GAG AAC CAG CTT CTA TCT CTT GCA
        GGT CTA GTC AGA G
                                                            LA
L2  5'- ACT GGC CAG GCT TCT GCA GGT ACC AAG ACA AAT AGG TGT TCC
        CAT AAC TCT TTG CAA GAC TCT GAC TAG ACC TGC AAG AGA
        TAG AAG CTG GTT C

L3  5'- CCT GGC CAG TCT CCA CAG CTC CTC ATC TAT GGG ATT TCC AAC
        AGA TTT TCT GGG GTG CCA GAC AGG TTC AGT GGC AGT GGT
        TC
                                                            LB
L4  5'- ACT CGC GAG ATC TTG AGT GTG AAA TCT GTC CCT GAA CCA CTG
        CCA CTG AAC CTG TCT GGC ACC CCA GAA AAT CTG TTG GAA
        ATC

L5  5'- TCT CGC GAG TAG AGG CTG AGG ACG TGG GAG TGT ATT ACT GCT
        TAC AAG GTA CAC ATC AGC CGT ACA C
                                                            LC
L6  5'- ATG GCG CCG CAT CAG CCC GTT TTA TTT CCA CCT TGG TCC CCT
        GTC CGA ACG TGT ACG GCT GAT GTG TAC CTT GTA AGC AGT
        AAT AC

HEAVY CHAIN OLIGOS  DOUBLE STRAND FRAGMENT

H1  5'- ATA AGC TTC GCC ATG AAA TGC ACC TGG GTC ATT CTC TTC TTG
        GTA TCA ACA GCT ACA AGT GTC CAC TCC CAG GTC CAA CTA
        GTG CAC CGG TTA
                                                            HA
H2  5'- TAA CCG GTG CAC TAG TTG GAC CTG GGA GTG GAC ACT TGT AGC
        TGT TGA TAC CAA GAA GAG AAT GAC CCA GGT GCA TTT CAT
        GGC GAA GCT TAT

H3  5'- CAA CTA GTG CAG TCT GGG GCT GAG GTT AAG AAG CCT GGG GCT
        TCA GTG AAG GTG TCC TGC AAG GGT TCT GGC TAC ACC TTC
        ACC AGC
                                                            HB
H4  5'- TAA CCG GTA CTC TAG ACG TTG GCC AGG CGC CTG CCT CAC CCA
        ATG CAT CCA GTA GCT GGT GAA GGT GTA GCC AGA ACC CTT
        GCA GGA C

H5  5'- CGT CTA GAG TGG ATC GGA GAG ATT GAT CCT TCT GAG AGT AAT
        ACT AAC TAC AAT CAA AAA TTC AAG GGA CGC GTC A
                                                            HC
H6  5'- TAA CCG GTG TGC TAG CGG AAA TGT CTA CAG TCA ATG TGA CGC
        GTC CCT TGA ATT TTT GAT TGT AGT TAG TAT TAC T

H7  5'- CCG CTA GCA CAG CCT ACA TGG AGC TCA GCA GCC TGA GAT CTG
        AGG ACA CTG CGG TCT ACT ATT GTG CAA GAG GGG TTA CG
        ACG GAT G
                                                            HD
H8  5'- TCA CCG GTG CGG TGA CCA GGG TGC CTT GAC CCC AGT AGT CAA
        TAG CAT AGT CCC ATC CGT CGT AAC CCC CTC TTG CAC AAT
        AGT AGA C

H9  5'- CTG GTC ACC GTC TCC TCA GCC TCC ACC AAG GGC CCA TCG GTC
        TTC CCC CTG GCA CCC TCC TCC AAG AGC ACC TCT GGG GGC
        ACA G
                                                            HE
H10 5'- TCA CCG GTT CGG GGA AGT AGT CCT TGA CCA GGC AGC CCA
        GGG CCG CTG TGC CCC AGG TGC TCT TGG AGG AGG TG
        CCA GGG G

FIG. 13

HUMANIZED IMMUNOGLOBULIN REACTIVE WITH α4β7 INTEGRIN

RELATED APPLICATION

This application is a divisional of U.S. application Ser. No. 08/700,737, filed Aug. 15, 1996, now U.S. Patent No. 7,147,851. The entire teachings of the above application are incorporated herein by reference.

BACKGROUND OF THE INVENTION

Integrin receptors are important for regulating both lymphocyte recirculation and recruitment to sites of inflammation (Carlos, T. M. and Harlan, J. M., *Blood*, 84:2068-2101 (1994)). The human α4β7 integrin has several ligands, one of which is the mucosal vascular addressin MAdCAM-1 (Berlin, C., et al., *Cell* 74:185-195 (1993); Erle, D. J., et al., *J. Immunol.* 153:517-528 (1994)) expressed on high endothelial venules in mesenteric lymph nodes and Peyer's patches (Streeter, P. R., et al., *Nature* 331:41-46 (1988)). As such, the α4β7 integrin acts as a homing receptor that mediates lymphocyte migration to intestinal mucosal lymphoid tissue (Schweighoffer, T., et al., *J. Immunol.* 151:717-729 (1993)). In addition, the α4β7 integrin interacts with fibronectin and vascular cell adhesion molecule-1 (VCAM-1).

Inflammatory bowel disease (IBD), such as ulcerative colitis and Crohn's disease, for example, can be a debilitating and progressive disease involving inflammation of the gastrointestinal tract. Affecting an estimated two million people in the United States alone, symptoms include abdominal pain, cramping, diarrhea and rectal bleeding. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *New Engl. J. Med.*, 325:928-937 (1991) and Podolsky, *New Engl. J. Med.*, 325: 1008-1016 (1991).

Antibodies against human α4β7 integrin, such as murine monoclonal antibody (mAb Act-1), interfere with α4β7 integrin binding to mucosal addressin cell adhesion molecule-1 (MAdCAM-1) present on high endothelial venules in mucosal lymph nodes. Act-1 was originally isolated by Lazarovits, A. I., et al., *J. Immunol.* 133:1857-1862 (1984), from mice immunized with human tetanus toxoid-specific T lymphocytes and was reported to be a mouse IgG1/κ antibody. More recent analysis of the antibody by Schweighoffer, T., et al., *J. Immunol.* 151:717-729 (1993) demonstrated that it can bind to a subset of human memory CD4+ T lymphocytes which selectively express the α4β7 integrin. However, a serious problem with using murine antibodies for therapeutic applications in humans is that they are highly immunogenic in humans and quickly induce a human anti-murine antibody response (HAMA), which reduces the efficacy of the mouse antibody in patients and can prevent continued administration. The HAMA response results in rapid clearance of the mouse antibody, severely limiting any therapeutic benefit.

Thus, a need exists for improved therapeutic approaches to inflammatory bowel diseases.

SUMMARY OF THE INVENTION

The present invention relates to a humanized immunoglobulin having binding specificity for α4β7 integrin, said immunoglobulin comprising an antigen binding region of nonhuman origin (e.g., rodent) and at least a portion of an immunoglobulin of human origin (e.g., a human framework region, a human constant region of the gamma type). In one embodiment, the humanized immunoglobulin described herein can compete with murine Act-1 or LDP-02 (see, e.g., Example 4) for binding to α4β7 integrin. In a preferred embodiment, the antigen binding region of the humanized immunoglobulin is derived from Act-1 monoclonal antibody (e.g., LDP-02, an immunoglobulin comprising the variable regions of the light and heavy chains shown in FIG. 11 (SEQ ID NO:19) and FIG. 12 (SEQ ID NO:21), respectively).

For example, the humanized immunoglobulin can comprise an antigen binding region comprising a complementarity determining region (CDR) of nonhuman origin, and a framework region (FR) derived from a human framework region. In one aspect, the humanized immunoglobulin having binding specificity for α4β7 integrin, comprises a light chain comprising a CDR derived from an antibody of nonhuman origin which binds α4β7 and a FR derived from a light chain of human origin (e.g., GM607'CL), and a heavy chain comprising a CDR derived from an antibody of nonhuman origin which binds α4β7 and a FR derived from a heavy chain of human origin (e.g., 21/28'CL). In another aspect, the light chain comprises three CDRs derived from the light chain of the Act-1 antibody, and the heavy chain comprises three CDRs derived from the heavy chain of the Act-1 antibody.

The present invention also relates to humanized immunoglobulin light chains (e.g., comprising CDR1, CDR2 and CDR3 of the light chain of the Act-1 antibody, and a human light chain FR), and to humanized immunoglobulin heavy chains (e.g., comprising CDR1, CDR2 and CDR3 of the heavy chain of the Act-1 antibody, and a human heavy chain FR). In a preferred embodiment, the invention relates to humanized heavy and light chains described herein (e.g., a humanized light chain comprising the variable region of the light chain shown in FIG. 7 (SEQ ID NO:12), a humanized heavy chain comprising the variable region of the heavy chain shown in FIG. 9 (SEQ ID NO:15), a humanized light chain comprising the variable region of the light chain shown in FIG. 12 (SEQ ID NO:21), a humanized heavy chain comprising the variable region of the heavy chain shown in FIG. 11 (SEQ ID NO:19)). Also encompassed are humanized immunoglobulins comprising one or more humanized light and/or heavy chains.

The invention further relates to isolated nucleic acids comprising a sequence which encodes a humanized immunoglobulin of the present invention (e.g., a single chain antibody), as well as to isolated nucleic acids comprising a sequence which encodes a humanized immunoglobulin light chain (e.g., SEQ ID NO:20) or heavy chain (e.g., SEQ ID NO:18) of the present invention. For example, the present invention provides a fused gene encoding a humanized immunoglobulin light or heavy chain comprising a first nucleic acid sequence encoding an antigen binding region derived from murine Act-1 monoclonal antibody; and a second nucleic acid sequence encoding at least a portion of a constant region of an immunoglobulin of human origin.

The present invention further relates to a construct comprising a nucleic acid encoding a humanized immunoglobulin having binding specificity for α4β7 integrin or a chain of such an immunoglobulin. For example, an expression vector comprising a fused gene encoding a humanized immunoglobulin light chain, comprising a nucleotide sequence encoding a CDR derived from a light chain of a nonhuman antibody having binding specificity for α4β7 integrin, and a framework region derived from a light chain of human origin, is provided. An expression vector comprising a fused gene encoding a humanized immunoglobulin heavy chain, comprising a nucleotide sequence encoding a CDR derived from a heavy chain of a nonhuman antibody having binding specificity for α4β7 integrin, and a framework region derived from a heavy chain of human origin is another example of such a construct.

The present invention also relates to a host cell comprising a nucleic acid of the present invention, including one or more constructs comprising a nucleic acid of the present invention. In one embodiment, the invention relates to a host cell comprising a first recombinant nucleic acid encoding a humanized immunoglobulin light chain, and a second recombinant nucleic acid encoding a humanized immunoglobulin heavy chain, said first nucleic acid comprising a nucleotide sequence encoding a CDR derived from the light chain of murine Act-1 antibody and a framework region derived from a light chain of human origin; and said second nucleic acid comprising a nucleotide sequence encoding a CDR derived from the heavy chain of murine Act-1 antibody and a framework region derived from a heavy chain of human origin.

The present invention also provides a method of preparing a humanized immunoglobulin comprising maintaining a host cell of the present invention under conditions appropriate for expression of a humanized immunoglobulin, whereby a humanized immunoglobulin chain(s) is expressed and a humanized immunoglobulin is produced. The method can further comprise the step of isolating the humanized immunoglobulin.

The humanized immunoglobulins of the present invention can be less immunogenic than their murine or other nonhuman counterparts. Thus, the humanized immunoglobulins described herein can be used as therapeutic agents in humans, for example to control lymphocyte homing to mucosal lymphoid tissue, thereby, reducing inflammatory responses in the gut.

BRIEF DESCRIPTION OF THE DRAWINGS

FIG. 1 is an illustration of a consensus DNA sequence (SEQ ID NO:1) and deduced amino acid sequence (SEQ ID NO:2) comprising the variable region determined from several independent mouse heavy chain variable region clones.

FIG. 2 is an illustration of a nucleotide sequence (SEQ ID NO:3) and deduced amino acid sequence (SEQ ID NO:4) comprising a portion of the variable region sequence determined from an independent mouse heavy chain variable region clone designated H2B#34.

FIG. 3 is an illustration of a nucleotide sequence (SEQ ID NO: 5) and deduced amino acid sequence (SEQ ID NO:6) comprising the variable region of several independent mouse light chain variable region clones. The position of two mutations made to introduce a KasI site for cloning are indicated.

FIG. 5 is an alignment of the amino acid sequences of the mouse Act-1 light chain variable region ("Act-1.vl") (SEQ ID NO:7) and of the human GM 607'CL light chain variable region (SEQ ID NO:8). Identical amino acids are indicated by a vertical line and similar amino acids are indicated by four or two dots, depending on the degree of similarity. CDRs are bracketed and labelled, and residues are numbered sequentially.

FIG. 6 is an alignment of the amino acid sequences of the mouse Act-1 heavy chain variable region ("Act-1.vh") (SEQ ID NO:9) and of the human 21/28'CL heavy chain variable region (SEQ ID NO:10). Identical amino acids are indicated by a vertical line and similar amino acids are indicated by four or two dots, depending on the degree of similarity. CDRs are bracketed and labelled, and residues are numbered sequentially.

FIG. 7 is an illustration of the nucleotide sequence of a double stranded nucleic acid (coding strand, SEQ ID NO:11; non-coding strand, SEQ ID NO:64) encoding the mouse Act-1 light chain variable region joined to the mouse Act-1 light chain signal peptide sequence, and the deduced amino acid sequence of the Act-1 light chain variable region joined to the mouse Act-1 light chain signal peptide sequence (SEQ ID NO:12).

FIG. 8 is an illustration of the nucleotide sequence of a double stranded nucleic acid (coding strand, SEQ ID NO:13; non-coding strand, SEQ ID NO:65) encoding the mature human GM607'CL antibody kappa light chain variable region, and the deduced amino acid sequence of the mature human GM607'CL antibody kappa light chain variable region (SEQ ID NO:8).

FIG. 9 is an illustration of the nucleotide sequence of a double stranded nucleic acid (coding strand SEQ ID NO:14; non-coding strand, SEQ ID NO: 66) encoding the mouse Act-1 antibody heavy chain and signal peptide, and the deduced amino acid sequence of the mouse Act-1 antibody heavy chain variable region and heavy chain signal peptide (SEQ ID NO:15). The nucleotide sequence of the variable region is joined to a nucleotide sequence which encodes a deduced mouse Act-1 heavy chain signal peptide sequence, to yield a composite sequence. (The identity of the primer which amplified the heavy chain region was deduced from the degenerate sequence, and an amino acid sequence for the signal peptide was derived from the primer, downsteam sequence and sequences of other signal peptides. The signal peptide shown may not be identical to that of the Act-1 hybridoma.)

FIG. 10 is an illustration of the nucleotide sequence of a double stranded nucleic acid (coding strand SEQ ID NO:16; non-coding strand, SEQ ID NO: 67) encoding the human 21/28'CL antibody heavy chain and signal peptide, and the deduced amino acid sequence of the human 21/28'CL antibody heavy chain variable region and heavy chain signal peptide (SEQ ID NO:17). The nucleotide sequence encoding the variable region is joined to a nucleotide sequence which encodes a signal peptide sequence derived from the $V_H$ of human antibody HG3'CL (Rechavi, G., et al., *Proc. Natl. Acad. Sci., USA* 80:855-859 (1983)), to yield a composite sequence.

FIG. 11 is an illustration of the nucleotide sequence (SEQ ID NO:18) and amino acid sequence (SEQ ID NO:19) of a portion of the heavy chain of a humanized Act-1 antibody (LDP-02) with a heavy chain signal peptide.

FIG. 12 is an illustration of the nucleotide sequence (SEQ ID NO:20) and amino acid sequence (SEQ ID NO:21) of a portion of the light chain of a humanized Act-1 antibody (LDP-02) with a light chain signal peptide.

FIG. 13 is an illustration of the nucleotide sequences of overlapping, complementary oligonucleotides designated L1-L6 (SEQ ID NOS:22-27), which were used to make the light chain of a humanized Act-1 immunoglobulin (LDP-02), and the nucleotide sequences of overlapping, complementary oligonucleotides designated H1-H10 (SEQ ID NOS:28-37), which were used to make the heavy chain of the humanized Act-1 immunoglobulin.

DETAILED DESCRIPTION OF THE INVENTION

Figure 4A:
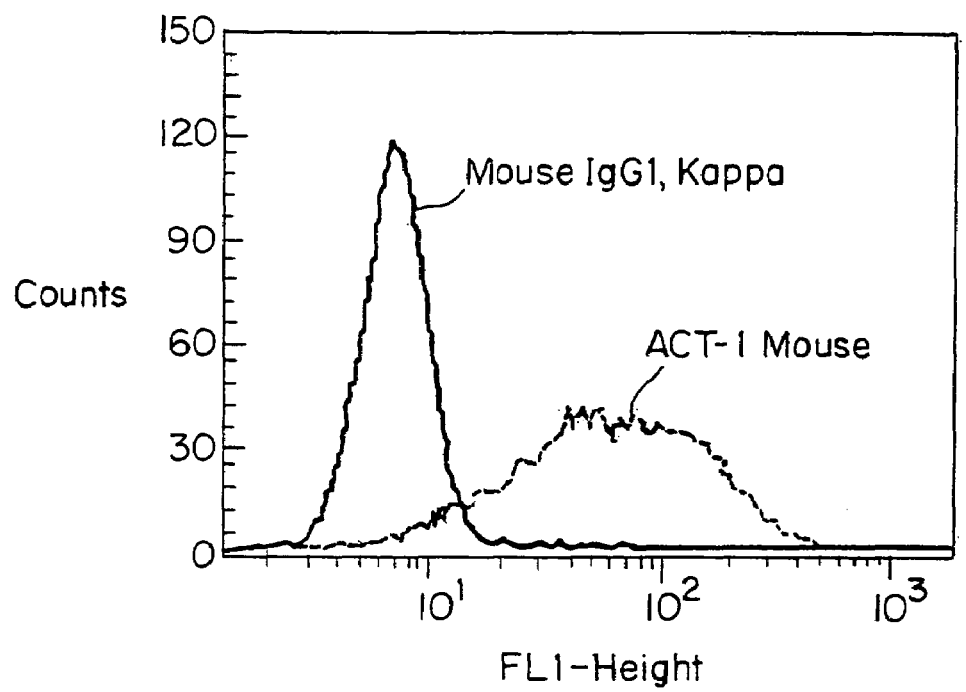
FIG. 4A is a fluorescence plot illustrating the ability of the murine Act-1 mAb and a mouse isotype-matched irrelevant control antibody (MOPC 21; IgG1, kappa) to stain HuT 78 cells which express α4β7 integrin.

The present invention relates to a humanized immunoglobulin having binding specificity for α4β7 integrin, comprising an antigen binding region of nonhuman origin and at least a portion of an immunoglobulin of human origin. Preferably, the humanized immunoglobulins can bind α4β7 integrin with an affinity of at least about $10^7$ M$^{-1}$, preferably at least about $10^8$ M$^{-1}$, and more preferably at least about $10^9$ M$^{-1}$. In one embodiment, the humanized immunoglobulin includes an antigen binding region of nonhuman origin which binds α4β7 integrin and a constant region derived from a human constant region. In another embodiment, the humanized immunoglobulin which binds α4β7 integrin comprises a complementarity determining region of nonhuman origin and a variable framework region of human origin, and optionally, a constant region of human origin. For example, the humanized immunoglobulin can comprise a heavy chain and a light chain, wherein the light chain comprises a complementarity determining region derived from an antibody of nonhuman origin which binds α4β7 integrin and a framework region derived from a light chain of human origin, and the heavy chain comprises a complementarity determining region derived from an antibody of nonhuman origin which binds α4β7 integrin and a framework region derived from a heavy chain of human origin.

The present invention also relates to a humanized immunoglobulin light chain or a humanized immunoglobulin heavy chain. In one embodiment, the invention relates to a humanized light chain comprising a light chain CDR (i.e., one or more CDRs) of nonhuman origin and a human light chain framework region. In another embodiment, the present invention relates to a humanized immunoglobulin heavy chain comprising a heavy chain CDR (i.e., one or more CDRs) of nonhuman origin and a human heavy chain framework region. The CDRs can be derived from a nonhuman immunoglobulin.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by Kabat et al. (Kabat, E. A. et al., *Sequences of proteins of Immunological Interest*, Fifth Edition, U.S. Department of Health and Human Services, U.S. Government Printing Office (1991); see also Tables 3 and 4).

Human immunoglobulins can be divided into classes and subclasses, depending on the isotype of the heavy chain. The classes include IgG, IgM, IgA, IgD and IgE, in which the heavy chains are of the gamma (γ), mu (µ), alpha (α), delta (δ) or epsilon (ε) type, respectively. Subclasses include IgG1, IgG2, IgG3, IgG4, IgA1 and IgA2, in which the heavy chains are of the γ1, γ2, γ3, γ4, α1 and α2 type, respectively. Human immunoglobulin molecules of a selected class or subclass may contain either a kappa (κ) or lambda (λ) light chain. See e.g., *Cellular and Molecular Immunology*, Wonsiewicz, M. J., Ed., Chapter 45, pp. 41-50, W. B. Saunders Co, Philadelphia, Pa. (1991); Nisonoff, A., *Introduction to Molecular Immunology*, 2nd Ed., Chapter 4, pp. 45-65, Sinauer Associates, Inc., Sunderland, Mass. (1984).

The term "immunoglobulin" as used herein includes whole antibodies and biologically functional fragments thereof. Such biologically functional fragments retain at least one antigen binding function of a corresponding full-length antibody (e.g., specificity for α4β7 of Act-1 antibody), and preferably, retain the ability to inhibit the interaction of α4β7 with one or more of its ligands (e.g., MAdCAM-1, fibronectin). In a particularly preferred embodiment, biologically functional fragments can inhibit binding of α4β7 to the mucosal addressin (MAdCAM-1). Examples of biologically functional antibody fragments which can be used include fragments capable of binding to an α4β7 integrin, such as single chain antibodies, Fv, Fab, Fab' and F(ab')$_2$ fragments. Such fragments can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a chimeric gene encoding the heavy chain of an F(ab')$_2$ fragment can be designed to include DNA sequences encoding the CH$_1$ domain and hinge region of the heavy chain.

The term "humanized immunoglobulin" as used herein refers to an immunoglobulin comprising portions of immunoglobulins of different origin, wherein at least one portion is of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

The antigen binding region of the humanized immunoglobulin (the nonhuman portion) can be derived from an immunoglobulin of nonhuman origin (referred to as a donor immunoglobulin) having binding specificity for α4β7 integrin. For example, a suitable antigen binding region can be derived from the murine Act-1 monoclonal antibody (Lazarovits, A. I. et al., J. Immunol., 133(4): 1857-1862 (1984)); see e.g., Examples 1-3). Other sources include α4β7 integrin-specific antibodies obtained from nonhuman sources, such as rodent (e.g., mouse, rat), rabbit, pig goat or non-human primate (e.g., monkey). Other polyclonal or monoclonal antibodies, such as antibodies which bind to the same or similar epitope as the Act-1 antibody, can be made (e.g., Kohler et al., Nature, 256:495-497 (1975); Harlow et al., 1988, Antibodies: A Laboratory Manual, (Cold Spring Harbor, N.Y.); and Current Protocols in Molecular Biology, Vol. 2 (Supplement 27, Summer '94), Ausubel et al., Eds. (John Wiley & Sons: New York, N.Y.), Chapter 11 (1991)).

For example, antibodies can be raised against an appropriate immunogen in a suitable mammal (e.g., a mouse, rat, rabbit or sheep). Cells bearing α4β7, membrane fractions containing α4β7, immunogenic fragments α4β7, β7 peptide conjugated to a suitable carrier are examples of suitable immunogens. Antibody-producing cells (e.g., a lymphocyte) can be isolated from, for example, the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay (e.g., ELISA). Immunoglobulins of nonhuman origin having binding specificity for α4β7 integrin can also be obtained from antibody libraries (e.g., a phage library comprising nonhuman Fab molecules).

In one embodiment, the antigen binding region of the humanized immunoglobulin comprises a CDR of nonhuman origin. In this embodiment, the humanized immunoglobulin having binding specificity for α4β7 integrin comprises at least one CDR of nonhuman origin. For example, CDRs can be derived from the light and heavy chain variable regions of immunoglobulins of nonhuman origin, such that a humanized immunoglobulin includes substantially heavy chain CDR1, CDR2 and/or CDR3, and/or light chain CDR1, CDR2 and/or CDR3, from one or more immunoglobulins of nonhuman origin, and the resulting humanized immunoglobulin has binding specificity for α4β7 integrin. Preferably, all three CDRs of a selected chain are substantially the same as the CDRs of the corresponding chain of a donor, and more preferably, all three CDRs of the light and heavy chains are substantially the same as the CDRs of the corresponding donor chain.

The portion of the humanized immunoglobulin or immunoglobulin chain which is of human origin (the human portion) can be derived from any suitable human immunoglobulin or immunoglobulin chain. For example, a human constant region or portion thereof, if present, can be derived from the κ or λ light chains, and/or the g (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, an mutated constant region (variant) can be incorporated into a fusion protein to minimize binding to Fc receptors and/or ability to fix complement (see e.g., Example 3; see also, Winter et al., GB 2,209,757 B; Morrison et al., WO 89/07142; Morgan et al., WO 94/29351, Dec. 22, 1994).

If present, human framework regions (e.g., of the light chain variable region) are preferably derived from a human antibody variable region having sequence similarity to the analogous or equivalent region (e.g., light chain variable region) of the antigen binding region donor. Other sources of framework regions for portions of human origin of a humanized immunoglobulin include human variable consensus sequences (see e.g., Example 2; see also, Kettleborough, C. A. et al., Protein Engineering 4:773-783 (1991); Carter et al., WO 94/04679, published Mar. 3, 1994)). For example, the sequence of the antibody or variable region used to obtain the nonhuman portion can be compared to human sequences as described in Kabat, E. A., et al., Sequences of Proteins of Immunological Interest, Fifth Edition, U.S. Department of Health and Human Services, U.S. Government Printing Office (1991). In a particularly preferred embodiment, the framework regions of a humanized immunoglobulin chain are derived from a human variable region having at least about 65% overall sequence identity, and preferably at least about 70% overall sequence identity, with the variable region of the nonhuman donor (e.g., mouse Act-1 antibody). A human portion can also be derived from a human antibody having at least about 65% sequence identity, and preferably at least about 70% sequence identity, within the particular portion (e.g., FR) being used, when compared to the equivalent portion (e.g., FR) of the nonhuman donor. For example, as described in Example 2, the overall sequence identity between the mouse Act-1 and human GM607'CL light chain variable regions was 71.4%, and the overall sequence identity between the mouse Act-1 and human 21/28'CL heavy chain variable regions was 68.1%.

In one embodiment, the humanized immunoglobulin comprises at least one of the framework regions (FR) derived from one or more chains of an antibody of human origin. Thus, the FR can include a FR1 and/or FR2 and/or FR3 and/or FR4 derived from one or more antibodies of human origin. Preferably, the human portion of a selected humanized chain includes FR1, FR2, FR3 and FR4 derived from a variable region of human origin (e.g., from a human immunoglobulin chain, from a human consensus sequence).

The immunoglobulin portions of nonhuman and human origin for use in the present invention have sequences identical to immunoglobulins or immunoglobulin portions from which they are derived or to variants thereof. Such variants include mutants differing by the addition, deletion, or substitution of one or more residues. As indicated above, the CDRs which are of nonhuman origin are substantially the same as in the nonhuman donor, and preferably are identical to the CDRs of the nonhuman donor. As described in Example 2, changes in the framework region, such as those which substitute a residue of the framework region of human origin with a residue from the corresponding position of the donor, can be made. One or more mutations in the framework region can be made, including deletions, insertions and substitutions of one or more amino acids. Several such substitutions are described in the design of a humanized Act-1 antibody in Example 2. For a selected humanized antibody or chain, framework mutations can be designed as described herein. Preferably, the humanized immunoglobulins can bind $\alpha 4\beta 7$ integrin with an affinity similar to or better than that of the nonhuman donor. Variants can be produced by a variety of suitable methods, including mutagenesis of nonhuman donor or acceptor human chains.

The humanized immunoglobulins of the present invention have binding specificity for human $\alpha 4\beta 7$ integrin, and include humanized immunoglobulins (including fragments) which can bind determinants of the ($\alpha 4$ and/or $\beta 7$ chains of the heterodimer. In a preferred embodiment, the humanized immunoglobulin of the present invention has at least one function characteristic of murine Act-1 antibody, such as binding function (e.g., having specificity for $\alpha 4\beta 7$ integrin, having the same or similar epitopic specificity), and/or inhibitory function (e.g., the ability to inhibit $\alpha 4\beta 7$-dependent adhesion in vitro and/or in vivo, such as the ability to inhibit $\alpha 4\beta 7$ integrin binding to MAdCAM-1 in vitro and/or in vivo, or the ability to inhibit the binding of a cell bearing $\alpha 4\beta 7$ integrin to a ligand thereof (e.g., a cell bearing MAdCAM-1)). Thus, preferred humanized immunoglobulins can have the binding specificity of the murine Act-1 antibody, the epitopic specificity murine Act-1 antibody (e.g., can compete with murine Act-1, a chimeric Act-1 antibody (see e.g., Example 1), or humanized Act-1 (e.g., LDP-02) for binding to $\alpha 4\beta 7$ (e.g., on a cell bearing $\alpha 4\beta 7$ integrin)), and/or inhibitory function.

The binding function of a humanized immunoglobulin having binding specificity for $\alpha 4\beta 7$ integrin can be detected by standard immunological methods, for example using assays which monitor formation of a complex between humanized immunoglobulin and $\alpha 4\beta 7$ integrin (e.g., a membrane fraction comprising $\alpha 4\beta 7$ integrin, on a cell bearing $\alpha 4\beta 7$ integrin, such as a human lymphocyte (e.g., a lymphocyte of the CD4+$\alpha 4^{hi}$,$\beta 1^{lo}$ subset), human lymphocyte cell line or recombinant host cell comprising nucleic acid encoding $\alpha 4$ and/or $\beta 7$ which expresses $\alpha 4\beta 7$ integrin).

Binding and/or adhesion assays or other suitable methods can also be used in procedures for the identification and/or isolation of humanized immunoglobulins (e.g., from a library) with the requisite specificity (e.g., an assay which monitors adhesion between a cell bearing an $\alpha 4\beta 7$ integrin and a ligand thereof (e.g., a second cell expressing MAdCAM, a MAdCAM-Ig chimera (see e.g., Example 4), or other suitable methods.

The immunoglobulin portions of nonhuman and human origin for use in the present invention include light chains, heavy chains and portions of light and heavy chains. These immunoglobulin portions can be obtained or derived from immunoglobulins (e.g., by de novo synthesis of a portion), or nucleic acids encoding an immunoglobulin or chain thereof having the desired property (e.g., binds $\alpha 4\beta 7$ integrin, sequence similarity) can be produced and expressed. Humanized immunoglobulins comprising the desired portions (e.g., antigen binding region, CDR, FR, C region) of human and nonhuman origin can be produced using synthetic and/or recombinant nucleic acids to prepare genes (e.g., cDNA) encoding the desired humanized chain. To prepare a portion of a chain, one or more stop codons can be introduced at the desired position. For example, nucleic acid (e.g., DNA) sequences coding for newly designed humanized variable regions can be constructed using PCR mutagenesis methods to alter existing DNA sequences (see e.g., Kamman, M., et al., *Nucl. Acids Res.* 17:5404 (1989)). PCR primers coding for the new CDRs can be hybridized to a DNA template of a previously humanized variable region which is based on the same, or a very similar, human variable region (Sato, K., et al., *Cancer Research* 53:851-856 (1993)). If a similar DNA sequence is not available for use as a template, a nucleic acid comprising a sequence encoding a variable region sequence can be constructed from synthetic oligonucleotides (see e.g., Kolbinger, F., *Protein Engineering* 8:971-980 (1993)). A sequence encoding a signal peptide can also be incorporated into the nucleic acid (e.g., on synthesis, upon insertion into a vector). If the natural signal peptide sequence is unavailable, a signal peptide sequence from another antibody can be used (see, e.g., Kettleborough, C. A., *Protein Engineering* 4:773-783 (1991)). Using these methods, methods described herein or other suitable methods, variants can be readily produced (see e.g., Example 5). In one embodiment, cloned variable regions (e.g., of LDP-02) can be mutagenized, and sequences encoding variants with the desired specificity can be selected (e.g., from a phage library; see e.g., Krebber et al., U.S. Pat. No. 5,514,548; Hoogengoom et al., WO 93/06213, published Apr. 1, 1993)).

Nucleic Acids and Constructs Comprising Same

The present invention also relates to isolated and/or recombinant (including, e.g., essentially pure) nucleic acids comprising sequences which encode a humanized immunoglobulin or humanized immunoglobulin light or heavy chain of the present invention.

Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.*, 19(9). 2471-2476 (1991); Lewis, A. P. and J. S. Crowe, *Gene,* 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

The present invention also relates more specifically to isolated and/or recombinant nucleic acids comprising a nucleotide sequence which encodes a humanized Act-1 immunoglobulin (i.e., a humanized immunoglobulin of the present invention in which the nonhuman portion is derived from the murine Act-1 monoclonal antibody) or chain thereof. In one embodiment, the light chain comprises three complementarity determining regions derived from the light chain of the Act-1 antibody, and the heavy chain comprises three complementarity determining regions derived from the heavy chain of the Act-1 antibody. Such nucleic acids include, for example, (a) a nucleic acid comprising a sequence which encodes a polypeptide comprising the amino acid sequence of the heavy chain variable region of a humanized Act-1 immunoglobulin (e.g., heavy chain variable region of FIG. 11 (SEQ ID NO:19), heavy chain variable region of FIG. 9 (SEQ ID NO:15)), (b) a nucleic acid comprising a sequence which encodes a polypeptide comprising the amino acid sequence of the light chain variable region of a humanized Act-1 immunoglobulin (e.g., light chain variable region of FIG. 12 (SEQ ID NO:21), light chain variable region of FIG. 7 (SEQ ID NO:12)), (c) a nucleic acid comprising a sequence which encodes at least a functional portion of the light or heavy chain variable region of a humanized Act-1 immunoglobulin (e.g., a portion sufficient for antigen binding of a humanized immunoglobulin which comprises said chain). Due to the degeneracy of the genetic code, a variety of nucleic acids can be made which encode a selected polypeptide. In one embodiment, the nucleic acid comprises the nucleotide sequence of the variable region as set forth or substantially as set forth in FIG. 11 (SEQ ID NO:18), or as set forth or substantially as set forth in FIG. 12 (SEQ ID NO:20), including double or single-stranded polynucleotides. (Although various figures may illustrate polypeptides which are larger than the variable region (i.e., include a signal peptide coding sequence or a portion of a constant region coding sequence), reference to the variable region of a particular figure is meant to include the variable region portion of the sequence shown.) Isolated and/or recombinant nucleic acids meeting these criteria can comprise nucleic acids encoding sequences identical to sequences of humanized Act-1 antibody or variants thereof as discussed above.

Nucleic acids of the present invention can be used in the production of humanized immunoglobulins having binding specificity for α4β7 integrin. For example, a nucleic acid (e.g., DNA) encoding a humanized immunoglobulin of the present invention can be incorporated into a suitable construct (e.g., a vector) for further manipulation of sequences or for production of the encoded polypeptide in suitable host cells.

Method of Producing Humanized Immunoglobulins Having Specificity for α4β7 Integrin Another aspect of the invention relates to a method of preparing a humanized immunoglobulin which has binding specificity for α4β7 integrin. The humanized immunoglobulin can be obtained, for example, by the expression of one or more recombinant nucleic acids encoding a humanized immunoglobulin having binding specificity for α4β7 integrin in a suitable host cell, for example.

Constructs or expression vectors suitable for the expression of a humanized immunoglobulin having binding specificity for α4β7 integrin are also provided. The constructs can be introduced into a suitable host cell, and cells which express a humanized immunoglobulin of the present invention, can be produced and maintained in culture. Suitable host cells can be procaryotic, including bacterial cells such as *E. coli*, *B. subtilis* and or other suitable bacteria, or eucaryotic, such as fungal or yeast cells (e.g., *Pichia pastoris*, *Aspergillus species*, *Saccharomyces cerevisiae*, *Schizosaccharomyces pombe*, *Neurospora crassa*), or other lower eucaryotic cells, and cells of higher eucaryotes such as those from insects (e.g., Sf9 insect cells (WO 94/26087, O'Connor, published Nov. 24, 1994)) or mammals (e.g., COS cells, NSO cells, SP2/0, Chinese hamster ovary cells (CHO), HuT 78 cells, 293 cells). (See, e.g., Ausubel, F. M. et al., eds. *Current Protocols in Molecular Biology*, Greene Publishing Associates and John Wiley & Sons Inc., (1993)).

Host cells which produce a humanized immunoglobulin having binding specificity for α4β7 integrin can be produced as follows. For example, a nucleic acid encoding all or part of the coding sequence for the desired humanized immunoglobulin can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion. In a construct, a signal sequence can be provided by the vector or other source. For example, the transcriptional and/or translational signals of an immunoglobulin can be used to direct expression.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid (i.e., one or more nucleic acids) encoding the heavy and light chains of a humanized immunoglobulin having binding specificity for α4β7 integrin, or a construct (i.e., one or more constructs) comprising such nucleic acid(s), can be introduced into a suitable host cell by a method appropriate to the host cell selected (e.g., transformation, transfection, electroporation, infection), such that the nucleic acid(s) are operably linked to one or more expression control elements (e.g., in a vector, in a construct created by processes in the cell, integrated into the host cell genome).

Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded protein (e.g., humanized Act-1 antibody) can be isolated from (e.g., the host cells, medium, milk). This process encompasses expression in a host cell of a transgenic animal (see e.g., WO 92/03918, GenPharm International, published Mar. 19, 1992).

Fusion proteins can be produced in which a humanized immunoglobulin or immunoglobulin chain is linked to a non-immunoglobulin moiety (i.e., a moiety which does not occur in immunoglobulins as found in nature) in an N-terminal location, C-terminal location or internal to the fusion protein. For example, some embodiments can be produced by the insertion of a nucleic acid encoding immunoglobulin sequences into a suitable expression vector, such as a pET vector (e.g., pET-15b, Novagen), a phage vector (e.g., pCANTAB 5 E, Pharmacia), or other vector (e.g., pRIT2T Protein A fusion vector, Pharmacia). The resulting construct can be introduced into a suitable host cell for expression. Upon expression, some fusion proteins can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1-16.7.8 (1991)).

Therapeutic Methods and Compositions

The present invention provides humanized immunoglobulins which (1) can bind $\alpha 4\beta 7$ integrin in vitro and/or in vivo; and/or (2) can modulate an activity or function of an $\alpha 4\beta 7$ integrin, such as (a) binding function (e.g., the ability of $\alpha 4\beta 7$ integrin to bind to MAdCAM-1, fibronectin and/or VCAM-1) and/or (b) leukocyte infiltration function, including recruitment and/or accumulation of leukocytes in tissues (e.g., the ability to inhibit lymphocyte migration to intestinal mucosal tissue). Preferably the humanized immunoglobulins are capable of selectively binding $\alpha 4\beta 7$ in vitro and/or in vivo, and inhibiting $\alpha 4\beta 7$-mediated interactions. In one embodiment, a humanized immunoglobulin can bind an $\alpha 4\beta 7$ integrin, and can inhibit binding of the $\alpha 4\beta 7$ integrin to one or more of its ligands (e.g., MAdCAM-1, VCAM-1, fibronectin), thereby inhibiting leukocyte infiltration of tissues (including recruitment and/or accumulation of leukocytes in tissues), preferably selectively. Such humanized immunoglobulins can inhibit cellular adhesion of cells bearing an $\alpha 4\beta 7$ integrin to vascular endothelial cells in mucosal tissues, including gut-associated tissues, lymphoid organs or leukocytes (especially lymphocytes such as T or B cells) in vitro and/or in vivo. In a particularly preferred embodiment, a humanized immunoglobulin (e.g., Act-1) can inhibit the interaction of $\alpha 4\beta 7$ with MAdCAM-1 and/or fibronectin.

The humanized immunoglobulins of the present invention are useful in a variety of processes with applications in research, diagnosis and therapy. For instance, they can be used to detect, isolate, and/or purify $\alpha 4\beta 7$ integrin or variants thereof (e.g., by affinity purification or other suitable methods), and to study $\alpha 4\beta 7$ integrin structure (e.g., conformation) and function.

The humanized immunoglobulins of the present invention can also be used in diagnostic applications (e.g., in vitro, ex vivo) or to modulate $\alpha 4\beta 7$ integrin function in therapeutic (including prophylactic) applications.

For example, the humanized immunoglobulins of the present invention can be used to detect and/or measure the level of an $\alpha 4\beta 7$ integrin in a sample (e.g., tissues or body fluids, such as an inflammatory exudate, blood, serum, bowel fluid, on cells bearing an $\alpha 4\beta 7$ integrin). For example, a sample (e.g., tissue and/or body fluid) can be obtained from an individual and a suitable immunological method can be used to detect and/or measure $\alpha 4\beta 7$ integrin expression, including methods such as enzyme-linked immunosorbent assays (ELISA), including chemiluminescence assays, radio-immunoassay, and immunohistology. In one embodiment, a method of detecting a selected $\alpha 4\beta 7$ integrin in a sample is provided, comprising contacting a sample with a humanized immunoglobulin of the present invention under conditions suitable for specific binding of the humanized immunoglobulin to the $\alpha 4\beta 7$ integrin and detecting antibody-$\alpha 4\beta 7$ integrin complexes which are formed. In an application of the method, humanized immunoglobulins can be used to analyze normal versus inflamed tissues (e.g., from a human) for $\alpha 4\beta 7$ integrin reactivity and/or expression (e.g., immunohistologically)) to detect associations between IBD or other conditions and increased expression of $\alpha 4\beta 7$ (e.g., in affected tissues). The humanized immunoglobulins of the present invention permit immunological methods of assessment of the presence of $\alpha 4\beta 7$ integrin in normal versus inflamed tissues, through which the presence of disease, disease progress and/or the efficacy of anti-$\alpha 4\beta 7$ integrin therapy in inflammatory disease can be assessed.

The humanized immunoglobulins of the present invention can also be used to modulate (e.g., inhibit (reduce or prevent)) binding function and/or leukocyte (e.g., lymphocyte, monocyte) infiltration function of $\alpha 4\beta 7$ integrin. For example, humanized immunoglobulins which inhibit the binding of $\alpha 4\beta 7$ integrin to a ligand (i.e., one or more ligands) can be administered according to the method in the treatment of diseases associated with leukocyte (e.g., lymphocyte, monocyte) infiltration of tissues (including recruitment and/or accumulation of leukocytes in tissues), particularly of tissues which express the molecule MAdCAM. An effective amount of a humanized immunoglobulin of the present invention (i.e., one or more) is administered to an individual (e.g., a mammal, such as a human or other primate) in order to treat such a disease. For example, inflammatory diseases, including diseases which are associated with leukocyte infiltration of the gastrointestinal tract (including gut-associated endothelium), other mucosal tissues, or tissues expressing the molecule MAdCAM-1 (e.g., gut-associated tissues, such as venules of the lamina propria of the small and large intestine; and mammary gland (e.g., lactating mammary gland)), can be treated according to the present method. Similarly, an individual having a disease associated with leukocyte infiltration of tissues as a result of binding of leukocytes to cells (e.g., endothelial cells) expressing MAdCAM-1 can be treated according to the present invention.

In a particularly preferred embodiment, diseases which can be treated accordingly include inflammatory bowel disease (IBD), such as ulcerative colitis, Crohn's disease, ileitis, Celiac disease, nontropical Sprue, enteropathy associated with seronegative arthropathies, microscopic or collagenous colitis, eosinophilic gastroenteritis, or pouchitis resulting after proctocolectomy, and ileoanal anastomosis.

Pancreatitis and insulin-dependent diabetes mellitus are other diseases which can be treated using the present method. It has been reported that MAdCAM-1 is expressed by some vessels in the exocrine pancreas from NOD (nonobese diabetic) mice, as well as from BALB/c and SJL mice. Expression of MAdCAM-1 was reportedly induced on endothelium in inflamed islets of the pancreas of the NOD mouse, and MAdCAM-1 was the predominant addressin expressed by NOD islet endothelium at early stages of insulitis (Hanninen, A., et al., *J. Clin. Invest.*, 92: 2509-2515 (1993)). Further, accumulation of lymphocytes expressing α4β7 within islets was observed, and MAdCAM-1 was implicated in the binding of lymphoma cells via α4β7 to vessels from inflamed islets (Hanninen, A., et al., *J. Clin. Invest.*, 92: 2509-2515 (1993)).

Examples of inflammatory diseases associated with mucosal tissues which can be treated according to the present method include mastitis (mammary gland), cholecystitis, cholangitis or pericholangitis (bile duct and surrounding tissue of the liver), chronic bronchitis, chronic sinusitis, asthma, and graft versus host disease (e.g., in the gastrointestinal tract). As seen in Crohn's disease, inflammation often extends beyond the mucosal surface, accordingly chronic inflammatory diseases of the lung which result in interstitial fibrosis, such as hypersensitivity pneumonitis, collagen diseases, sarcoidosis, and other idiopathic conditions can be amenable to treatment.

The humanized immunoglobulin is administered in an effective amount which inhibits binding α4β7 integrin to a ligand thereof. For therapy, an effective amount will be sufficient to achieve the desired therapeutic (including prophylactic) effect (such as an amount sufficient to reduce or prevent α4β7 integrin-mediated binding and/or signalling, thereby inhibiting leukocyte adhesion and infiltration and/or associated cellular responses). The humanized immunoglobulin can be administered in a single dose or multiple doses. The dosage can be determined by methods known in the art and can be dependent, for example, upon the individual's age, sensitivity, tolerance and overall well-being. Suitable dosages for antibodies can be from about 0.1 mg/kg body weight to about 10.0 mg/kg body weight per treatment.

According to the method, the humanized immunoglobulin can be administered to an individual (e.g., a human) alone or in conjunction with another agent. A humanized immunoglobulin can be administered before, along with or subsequent to administration of the additional agent. In one embodiment, more than one humanized immunoglobulin which inhibits the binding of α4β7 integrin to its ligands is administered. In another embodiment, a monoclonal antibody, such as an anti-MAdCAM-1, anti-VCAM-1, or anti-ICAM-1 antibody, which inhibits the binding of leukocytes to an endothelial ligand is administered in addition to a humanized immunoglobulin of the present invention. In yet another embodiment, an additional pharmacologically active ingredient (e.g., an antiinflammatory compound, such as sulfasalazine, another non-steroidal antiinflammatory compound, or a steroidal antiinflammatory compound) can be administered in conjunction with a humanized immunoglobulin of the present invention.

A variety of routes of administration are possible, including, but not necessarily limited to, parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation will vary according to the route of administration selected (e.g., solution, emulsion). An appropriate composition comprising the humanized antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Sciences*, 17th Edition, Mack Publishing Co., PA, 1985). For inhalation, the compound can be solubilized and loaded into a suitable dispenser for administration (e.g., an atomizer, nebulizer or pressurized aerosol dispenser).

Exemplification

The present invention will now be illustrated by the following Examples, which are not intended to be limiting in any way.

As described in Example 1, murine Act-1 antibody was purified and sequence analysis of the antibody was performed. cDNAs encoding the light and heavy chain variable regions of mouse Act-1 antibody were PCR-cloned and sequenced. The amino acid sequence of the kappa light chain variable region ($V_L$) of Act-1 was also determined by protein sequencing and found to match exactly the amino acid sequence derived from the DNA sequence of the $V_L$ gene. Most of the amino acid sequence of the heavy chain variable region ($V_H$) has been determined by protein sequence, and this sequence also matches the amino acid sequence deduced from the DNA sequence of the $V_H$ gene. These results indicate that the correct mouse Act-1 variable regions were cloned from the hybridoma cell line. Functional chimeric Act-1 antibodies were produced which confirmed that the correct sequences have been cloned. In particular, the DNAs encoding mouse Act-1 light and heavy chain variable regions were joined to DNAs encoding human kappa light chain and human gamma-1 or gamma-4 heavy chain constant regions, respectively. The chimeric antibody was also used in a comparative analysis with a humanized Act-1 mAb (reshaped Act-1 mAb LDP-02).

To create a humanized Act-1 antibody that binds well to α4β7 integrin, reshaped human variable regions were designed (Example 2). In order to assist in the design process, a molecular model of the mouse Act-1 variable regions was built. The regions of the murine Act-1 antibody directly involved in binding to antigen, the complementarity determining region or CDRs, were grafted into selected human variable regions. A few amino acid changes at positions within the framework regions (FRs) of the human variable regions were made. The reshaped human Act-1 variable regions, included a single amino acid change in the FRs of the selected human light chain variable region and five amino acid changes in the FRs of the selected human heavy chain variable region, each changing the original human residue to the corresponding murine residue.

As described in Example 3, DNA sequences encoding these reshaped human Act-1 variable regions were constructed and joined to DNA sequences encoding human constant regions, and the resulting nucleic acids were used to produce humanized Act-1 immunoglobulin. Humanized Act-1 antibody was expressed in mammalian cells (Example 3), and was tested for binding to human α4β7 integrin in comparison with mouse Act-1 antibody (Example 4). As shown in Table 5, the humanized Act-1 antibody retained specificity for the epitope recognized by murine Act-1, and displayed unexpectedly improved binding affinity as compared with the native murine antibody.

Several variants of the humanized Act-1 antibody were identified in the design process (Examples 2 and 5). For example, additional changes at one or more of the following positions can be made: light chain mutant M4V (Met→Val mutation at position 4), heavy chain mutant R38K (Arg→Lys mutation at position 38), heavy chain mutant A40R (Ala→Arg mutation at position 40). In addition, a heavy chain mutant 173T (Ile→Thr back-mutation at position 73), restoring position 73 to the human threonine residue found at this position in the human framework region. Introduction of one or more of these changes in a single chain or various combinations of these changes in more than one chain can be made.

Murine Act-1 Hybridoma cell line, which produces the murine Act-1 monoclonal antibody, was deposited under the provisions of the Budapest Treaty on Aug. 22, 2001, on behalf Millennium Pharmaceuticals, Inc., 75 Sidney Street, Cambridge, Mass. 02139, U.S.A., at the American Type Culture Collection, 10801 University Boulevard, Manassas, Va. 20110, U.S.A., under Accession No. PTA-3663.

EXAMPLE 1

Cloning of Act-1 $V_H$ and $V_L$ Regions, and Construction and Expression of a Murine-human Act-1 Chimeric Immunoglobulin Cloning of Act-1 $V_H$ and $V_L$ Regions RNA was obtained from hybridoma cells which produce Act-1 monoclonal antibody (Lazarovits, A. I. et al., *J. Immunol.*, 133(4): 1857-1862 (1984); provided by A. I. Lazarovits and R. B. Colvin)) using TRIzol Reagent (Gibco/BRL) following the manufacturer's suggested protocol.

Transcribed heavy and light chain variable regions were amplified by polymerase chain reaction (PCR) using an Ig-Prime kit (Novagen) according to the maufacturer's suggested protocol. Briefly, 1.5 µg of total RNA was reverse transcribed to cDNA in a reaction containing 2.0 µl 5×MMLV Buffer (5×=250 mM Tris-HCl, pH 8.3 at 25° C., 375 mM KCl, 15 mM $MgCl_2$), 1.0 µl 100 mM DTT (dithiothreitol), 0.5 µl 10 µM dNTP mix (10 mM each dATP, dCTP, dTTP, dGTP), 0.5 µl oligo dT (1 mg/ml), 0.25 µl acetylated BSA (4 mg/ml), 1.0 µl of appropriate Ig-3' primer (10 pmol/µl), 0.5 µl MMLV Reverse Transcriptase (200 units/µl) and RNase-free water added to a total volume of 10 µl. The mixture was incubated for 5 minutes at 37° C., 30 minutes at 42° C., and 5 minutes at 99° C. Each Ig-3' primer was used in a separate reaction.

Variable regions were amplified from the reverse transcribed material according to the manufacturer's protocol. Briefly, 8 µl of the reverse transcribed material was mixed with 4 µl of 2.5 mM dNTPs, 5 µl 10×reaction buffer (10×=100 mM Tris-HCl, pH 8.8 at 25° C., 500 mM KCl, 15 mM $MgCl_2$, 1% Triton X-100), 2.5 µl Ig-5' lead primer (10 pmol/µl) (each Ig-5' leader primer was used in a separate PCR reaction), 0.25 µl (1.25 units) AmpliTaq® DNA polymerase (Perkin-Elmer), and water to a total volume of 50 µl.

For amplifications with 5' primers $MuIgV_H5'$-A, $MuIgV_H5'$-B, $MuIg\kappa V_L5'$-A, and $MuIg\kappa V_L5'$-B, the cycle parameters were 35 cycles of 1 minute, 94° C.; 1 minute, 50° C.; 2 minutes, 72° C.; followed by a final 6 minute extension at 72° C. The same reaction conditions were used for all other 5' primers, except that the annealing temperature was raised to 60° C.

The heavy chain variable region was successfully amplified using either $MuIgGV_H3'$-2 or $MuIgMV_H3'$-1 as the 3' primer, and either $MuIgV_H5'$-B or $MuIgV_H5'$-E as the 5' primers. The light chain variable region was successfully amplifed using $MuIg\kappa V_L3'$-1 as the 3' primer and $MuIg\kappa V_L5'$-G as the 5' primer.

The sequences of these primers were as follows:

```
MuIgGV_H3'-2 (SEQ ID NO:56):
5'-CCC AAG CTT CCA GGG RCC ARK GGA TAR ACI GRT GG

MuIgMV_H3'-1 (SEQ ID NO:57):
5'-CCC AAG CTT ACG AGG GGG AAG ACA TTT GGG AA

MuIgV_H5'-B (SEQ ID NO:58):
5'-GGG AAT TCA TGR AAT GSA SCT GGG TYW TYC TCT T

MuIgV_H5'-E (SEQ ID NO:59):
5'-ACT AGT CGA CAT GAA GWT GTG GBT RAA CTG GRT

MuIgκV_L3'-1 (SEQ ID NO:60):
5'-CCC AAG CTT ACT GGA TGG TGG GAA GAT GGA

MuIgκV_L5'-G (SEQ ID NO:61):
5'-ACT AGT CGA CAT GGA TTT WCA RGT GCA GAT TWT CAG
CTT
```

Amplified fragments were agarose gel purified and ligated into the pT7Blue T vector (Novagen) supplied with the Ig-Prime kit, and the ligation mixture was used to transform NovaBlue competent cells provided with the kit, according to the manufacturer's protocol.

White colonies containing inserts of the appropriate size were sequenced using T7 promoter primer and U-19mer primer which anneal on opposite sides of the insert just outside of the polycloning site of pT7Blue vector. Sequencing was performed on miniprep DNA using a Sequenase T7 DNA polymerase kit (USB/Amersham Life Science) according to manufacturer's recommended protocol.

The consensus DNA sequence (SEQ ID NO:1) from several independent heavy chain variable region clones and deduced amino acid sequence (SEQ ID NO:2) is shown in FIG. 1. Degenerate primers led to some degeneracy in sequence. The initiation codon is the Met encoded by nucleotides 13-15, the predicted leader peptidase cleavage site is between the Ser encoded by nucleotides 67-69 and the Gln encoded by nucleotides 70-72 (nucleotides 13-69 encoding the leader peptide). A portion of the murine constant region, beginning with the alanine encoded by residues 433-435, is shown.

The DNA sequence (SEQ ID NO:5) and amino acid sequence (SEQ ID NO:6) of several independent light chain variable region clones is shown in FIG. 3. Unlike the heavy chain variable region, the amplified sequences were not degenerate, probably because the primers used were not very degenerate and the variable region was amplified from only a single primer pair.

Construction of a Chimeric Heavy Chain Gene

A gene encoding a chimeric mouse-human heavy chain gene was produced. The source of the human heavy chain constant region was a clone containing a wild type human gamma one (γ1) constant region (obtained from Dr. Herman Waldmann (University of Oxford); a construct designated 3818 comprising a humanized anti-CD18 heavy chain gene in a pEE6 expression vector (Celltech). The constant region corresponds to that of the humanized CD18 heavy chain gene cloned into pEE6.hCMV as described in Sims, M. J. et al., *J. Immunol.*, 151 (4): 2296-2308 (1993) and WO 93/02191, published Feb. 4, 1993, the teachings of which are each incorporated herein by reference in their entirety. The sequences encoding the heavy chain variable and constant region (wild-type gamma one) of the humanized anti-CD18 antibody were released from the expression vector by digestion with HindIII and EcoRI. The 1,421 bp fragment containing the heavy chain gene was recovered and subcloned into the HindIII and EcoRI sites of pCR-Script™ (Stratagene) to yield a plasmid designated pCR-CD18H. An Spe I restriction site is located at the junction between the variable region and constant region in the anti-CD18 heavy chain gene. pCR-CD18H was restriction digested with HindIII and Spe I to release the heavy chain variable region. This variable region was replaced with the mouse Act-1 variable region generated as follows.

Two primers were synthesized to incorporate new restriction sites. These primers were:

```
5'-primer (SEQ ID NO:41):
Hind III
5'-T[AA GCT T]CC GCC ATG GGA TGG AGC

3'-primer (SEQ ID NO:42):
    Spe I
5'-GGT GAC [ACT AGT] GCC TTG ACC CCA G
```

Boldface type indicates a nucleotides in the primers which differ from the template sequence. An independent mouse Act-1 heavy chain clone designated H2B#34, with the nucleotide sequence (SEQ ID NO:3) and amino acid sequence (SEQ ID NO:4) presented in FIG. 2, was used as a template with the 5' and 3' primers above to amplify a mouse variable region concomitantly introducing a HindIII site 5' of the initiation codon and a Spe I site just 3' of the J region. The PCR fragment was directly subcloned into pCR-Script™ giving rise to plasmid pCR-mACT1HV, and the correct sequence was confirmed. The fragment was then released from pCR-mACT1HV by digestion with HindIII and Spe I, and inserted into the HindIII and Spe I sites of pCR-CD18H in place of the anti-CD18 variable region to yield pCR-mhACT1Hchi. The chimeric heavy chain (mouse Act-1 variable plus human gamma one constant) gene was then released from pCR-mhACT1Hchi with HindIII and EcoRI and cloned back into the pEE6hCMV-B vector, containing the hCMV promoter, to yield a construct designated pEE6mhACT1Hchi.

Construction of a Chimeric Light Chain Gene

A chimeric mouse-human light chain gene was constructed in a similar fashion as for the heavy chain. However, in the case of the chimeric light chain, a new restriction site, Kas I, was engineered into the construct by PCR amplification of a variable region fragment using one of the mouse Act-1 light chain variable region clones designated KG#87 as a template, and by PCR amplification of a kappa light chain constant region using a construct containing a humanized anti-CD18 kappa light chain gene as template (obtained from Dr. Herman Waldmann (University of Oxford); construct designated 3819 containing a humanized anti-CD18 light chain in the pEE12 expression vector). The constant region corresponds to that of the humanized CD18 light chain gene cloned into pEE12 as described in Sims, M. J. et al., *J. Immunol.*, 151 (4): 2296-2308 (1993) and WO 93/02191, published Feb. 4, 1993.

The primers for the variable region were:

```
5'-primer (SEQ ID NO:43):
HindIII
5'-T[AA GCT T]CC GCC ATG AAG TTG CCT

3'-primer (SEQ ID NO:44):
    Kas I
5'-[GGC GCC] GCA TCA GCC CGT TTT
```

Boldface type indicates nucleotides in the primer which differ from those in the template. The two nucleotide changes within the coding region, T→G at position 423 and A→G at position 426 in FIG. 3 to create the Kas I site are silent, and do not change the amino acid sequence.

The primers for the kappa constant region were:

```
5'-primer (SEQ ID NO:45):
Kas I
5'-C[GG CGC C]AT CTG TCT TCA TC

3'-primer (SEQ ID NO:46):
HindIII
    5'-[AAG CTT] CTA ACA CTC TCC
```

The light chain variable and constant regions were amplified separately with respective templates and primers, and the PCR products were individually subcloned into pCR-Script™ to confirm the sequence. Each fragment was then released from the vector by digestion with HindIII and KasI, gel purified and triple ligated into the HindIII site of the 3819 pEE12 expression vector from which the humanized anti-CD18 light chain gene had been removed by HindIII digestion. The resulting construct is designated pEE12mhACT1Lchi.

Expression of a Chimeric Immunoglobulin

For construction of an expression vector containing both chimeric heavy and light chain genes, the entire heavy chain gene plus CMV promoter was released from the pEE6 expression vector (pEE6mhACT1Hchi) by digestion with BglII and BamHI. This fragment was then ligated into the BamHI site of the pEE12 light chain gene expression vector (pEE12mhACT1Lchi) giving rise to a single plasmid designated pEE12mhLHchi, which contains both the chimeric light chain gene and chimeric heavy chain gene each under the transcription control of a separate CMV promoter.

The pEE6hCMV-B and pEE12 expression vectors and the Celltech glutamine synthetase gene amplification system have been described previously (see e.g., WO 86/05807 (Celltech), WO 87/04462 (Celltech), WO 89/01036 (Celltech), EP 0 323 997 B1 (Celltech), and WO 89/10404 (Celltech), the teachings of which are each incorporated herein by reference in their entirety).

For transient expression of the chimeric antibody, 20 µg of pEE12mhLHchi was transfected into COS-7 cells (American Type Culture Collection, 10801 University Boulevard, Manassas, Va. 20110-2209) by electroporation as follows. COS-7 cells growing in log phase were harvested from tissue culture flasks by treatment with trypsin-EDTA. The cells were washed once in Phosphate Buffered Saline (PBS), once with Hank's Balanced Salts Solution (HBSS), and resuspended at a concentration of $1.5 \times 10^7$ cells per ml of HBSS. $1.2 \times 10^7$ cells in 0.8 ml HBSS was mixed with 20 µg of the plasmid DNA and incubated for 10 minutes at room temperature. The DNA/cell mixture was then transferred to a 0.4 cm electroporation cuvette and current applied at 250 V, 960 µF with a Bio-Rad GenePulser. After a 10 minute post-electroporation incubation at room temperature, the cells were transferred to 20 mls of culture medium (Dulbecco's Modified Eagle's Medium (DMEM) plus 10% FCS) and cultured in a 162 cm² tissue culture flask (Costar). After 5 days, the cell culture supernatant was harvested and tested for the ability to stain HuT 78 cells which express the α4β7 integrin. HuT 78 cells (a human T cell lymphoma line) are available from the American Type Culture Collection, 10801 University Boulevard, Manassas, Va. 20110-2209, Accession No. ATCC TIB 161.

Figure 4B:
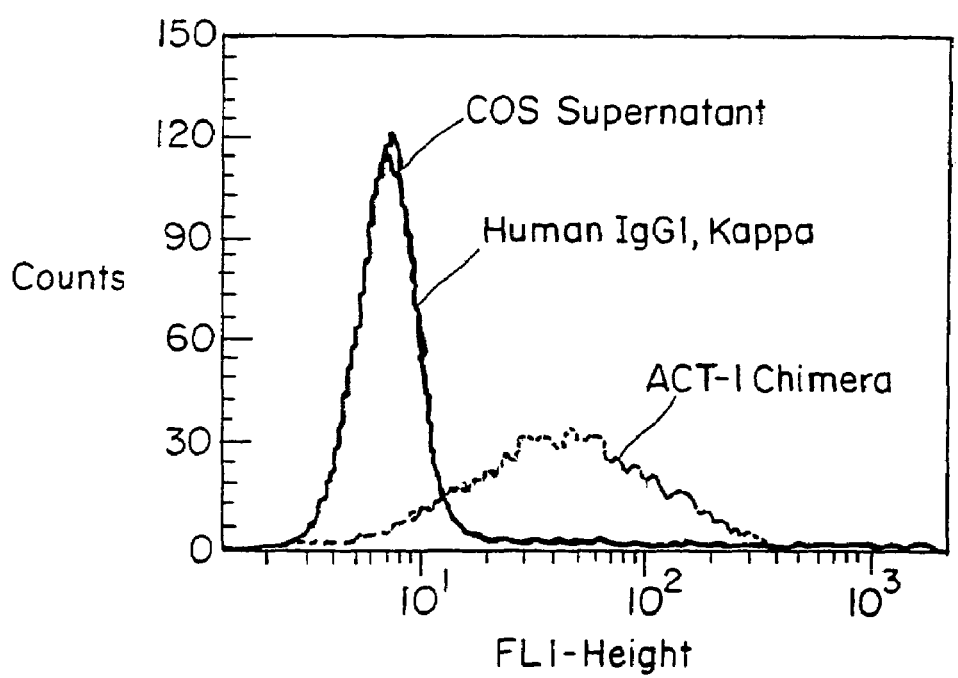
FIG. 4B is a fluorescence plot illustrating the ability of (i) chimeric Act-1 antibody, (ii) a human isotype-matched irrelevant control antibody (IgG1, kappa), and (iii) a COS-7 cell supernatant, to stain HuT 78 cells which express α4β7 integrin.

100 µl of transiently transfected COS-7 cell culture supernatant, mock transfected COS-7 cell supernatant, purified murine Act-1 antibody (10 µg/ml), or the respective purified irrelevant isotype-matched control antibodies for mouse (mouse IgG1, Kappa (MOPC21), 10 µg/ml from Sigma) and for human (human IgG1, Kappa, 10 µg/ml from Sigma) were incubated with 1×10$^5$ HuT 78 cells on ice for 30 minutes. The cells were washed twice with ice cold buffer consisting of PBS containing 2% fetal calf serum (FCS) and 0.01% sodium azide (FACS buffer). The cells were then incubated for 30 minutes on ice with the appropriate fluorescent secondary antibody (either fluorescein (FITC)-conjugated AffiniPure F(ab')$_2$ fragment goat anti-mouse IgG(H+L) (Jackson ImmunoResearch) or fluorescein (FITC)-conjugated AffiniPure F(ab')$_2$ fragment goat anti-human IgG(H+L) (Jackson ImmunoResearch)). After 30 minutes on ice, the cells were washed twice with FACS buffer, resuspended in 300 ml of the same buffer, and analyzed by flow cytometry on a Becton Dickinson FACscan. FIG. 4A shows staining of the murine Act-1 mAb compared to a mouse isotype matched irrelevant control antibody, MOPC 21 (IgG1, kappa). FIG. 4B shows chimeric Act-1 antibody staining of HuT 78 cells compared to a human isotype matched irrelevant control antibody (IgG1, kappa), and mock transfected COS-7 cell supernatant. Thus, compared to the stain produced by the murine Act-1 antibody, the chimeric antibody stained HuT 78 cells similarly. Collectively, these date demonstrate that the appropriate sequences for mouse Act-1 variable regions were successfully cloned and expressed.

Amino Acid Sequence Analysis

Amino acid sequence analysis was performed on purified murine Act-1 heavy and light chains to confirm the identities of the cDNAs for the light and heavy chain variable regions isolated from the hybridoma. This was accomplished for the light chain as follows:

Murine Act-1 (5 mg/ml) was reduced with 2 mM DTT for 2 hours at 37° C. in 0.3 M sodium borate, 0.15 M sodium chloride under nitrogen. The solution was then made 10 mM in iodoacetamide and incubated for 4 hr at room temperature. SDS-PAGE analysis under non-denaturing conditions confirmed that the proteins were reduced quantitatively. The protein solution was then extensively dialyzed in PBS and an aliquot applied to a Superdex 75 column (16/60, Pharmacia) (run 1). Heavy and light chain coeluted from this column with an elution volume corresponding to that of the exclusion volume indicating that the two chains were still held together. Another aliquot was then made 8M urea and ran on a superdex 75 column under denaturing conditions (6M urea) (run 2). Both chains again coeluted in the void volume probably due to unfolding. SDS-PAGE analysis confirmed the presence of both chains in the two samples eluted from the 2 gel filtration runs. These samples were subjected to N-terminal sequence analysis (Commonwealth Biotechnologies, Inc.) with the following result:

```
Sample 2: DVVVTQTPLSLPVSFDGQV    (SEQ ID NO:47)

Sample 1: DVVVTQTPLSL            (SEQ ID NO:48)
```

The sequence that was obtained corresponds to the N-terminus of the mature light chain as deduced from the DNA sequence. This and other attempts to obtain sequence of the heavy chain indicated that its N-terminus was likely blocked. Therefore, amino acid sequence analysis of internal peptide fragments was performed on the heavy chain.

To simplify internal amino acid sequencing F(ab)'2 fragments from the antibody were produced by cleaving with pepsin. Murine Act-1 was cleaved with pepsin at a ratio of antibody:pepsin of 1:200 for 2 hr at 37° C. in 0.1 M sodium citrate, pH 3.0. The reaction was complete as assessed by SDS-PAGE analysis. The protein was then purified through protein G and protein A columns. The sample was then reduced and alkylated as described above, and the heavy chain fragment was separated from the light chain by preparative SDS-PAGE (15%). The heavy chain fragment was excised, and electroleuted in 1 ml of 0.1% SDS with running buffer for 2 hours. This sample was cleaved with 2 ng of Asp-N endoproteinase for 30 minutes and the fragments were separated by SDS-PAGE (17.5%). The digestion products were passively eluted in 0.1 M Hepes pH 8.0, 0.1% SDS overnight and subjected to N-terminal sequence analysis (Commonwealth Biotechnologies, Inc.).

The sequence obtained from a 17 Kda fragment was DYAIDYWG (SEQ ID NO:49), which was present in the clone for the heavy chain (FIG. 1; the sequence AIDY corresponds to the beginning of the JH4 region).

EXAMPLE 2

Molecular Modelling of the Mouse Act-1 Variable Regions

In order to assist in the design of the CDR-grafted variable regions, a molecular model of the mouse Act-1 variable regions was produced. Modeling the structures of well-characterized protein families with immunoglobulins was done using the established methods for modeling by homology. Molecular modeling was carried out using a Silicon Graphics IRIS 4D workstation running under the UNIX operating system, the molecular modelling package QUANTA (Polygen Corp., Waltham, Mass.), and the Brookhaven crystallographic database of solved protein structures. As a first step, the framework regions (FRs) of the new variable regions were modeled on FRs from similar, structurally-solved immunoglobulin variable regions. While identical amino acid side chains were kept in their original orientation, mutated side chains were substituted using the maximum overlap procedure to maintain chi angles as in the original mouse Act-1 antibody. Most of the CDRs of the new variable regions were modeled based on the canonical structures for CDRs (Chothia, C., and A. M. Lesk, *J. Mol. Biol.* 196:901-917 (1987); Chothia, C., et al., *Nature* 342:877-883 (1989); Tramontano, A., et al., *J. Mol. Biol.* 215:175-182 (1990); Chothia, C., et al., *J. Mol. Biol.* 227:799-817 (1992)). In cases such as CDR3 of the heavy chain variable region, where there are no known canonical structures, the CDR loop was modelled based on a similar loop structure present in any structurally-solved protein. Finally, in order to relieve unfavourable atomic contacts and to optimize Van der Waals and electrostatic interactions, the model was subjected to energy minimization using the CHARMm potential (Brooks, B. R., *J. Comp. Chem.* 4:187-217 (1983)) as implemented in QUANTA.

For the mouse Act-1 variable regions, the FRs from the light chain variable region were modeled on the FRs from the Fab fragment of mouse monoclonal antibody 4-4-20 (Herron, J. N., et al., *Proteins. Structure, Function and Genetics* 5:271-280 (1989)). The FRs from the heavy chain variable region were modeled on the FRs from the Fab fragment of mouse monoclonal antibody D11.15 (Chitarra, V., et al., *Proc. Natl. Acad. Sci., USA* 90:7711-7715 (1993)). Those amino acid side chains which differed between the mouse Act-1 antibody and the variable regions upon which the model was based were substituted. The light chain of Fab 4-4-20 antibody was then superimposed onto the light chain of D11.15 by aligning in space residues 35-39, 43-47, 84-88 and 98-102 (as defined by Kabat, E. A., et al., *Sequences of Proteins of Immunological Interest*, Fifth Edition, U.S. Department of Health and Human Services, U.S. Government Printing Office (1991)), in order to place the two heterologous variable regions (i.e. the 4-4-20-based kappa light chain variable region and the D11.15-based heavy variable region) into the correct orientation with respect to each other.

CDR1 (L1) of the light chain variable region of mAb Act-1 fitted into the L1 canonical subgroup 4, as proposed by Chothia, C., et al., *Nature* 342:877-883 (1989). The L1 loop of mouse Fab 4-4-20 (see above) was identical in amino acid length, similar in amino acid sequence, and also matched canonical subgroup 4. Consequently the L1 loop was modeled on the L1 loop of Fab 4-4-20. Similarly, CDR2 (L2) and CDR3 (L3) of the light chain variable region of mAb Act-1 matched both their respective canonical subgroup 1 loop structures and the corresponding CDRs of Fab 4-4-20. Accordingly, the L2 and L3 loops of the Act-1 kappa light chain variable region were modeled on CDRs L2 and L3 of Fab 4-4-20.

CDR1 (H1) of the heavy chain variable region of mAb Act-1 fitted the H1 canonical subgroup 1, defined by Chothia, C., et al., *Nature* 342:877-883 (1989), as did the corresponding H1 loop of mouse mAb D 11.15 (see above). Moreover, mAb D11.15 CDR1 loop was identical in length and very similar in amino acid sequence to H1 of mAb Act-1. Consequently, as with the light chain, this loop was modeled on the CDR1 loop of the heavy variable region upon which the model was based. CDR2 of the heavy chain variable region (H2) was more difficult to define, but appeared to correspond to H2 canonical subgroup 2. Again, the H2 loop of the D11.15 antibody also matched the same canonical subgroup and was very similar in amino acid sequence, and so the H2 loop of mAb Act-1 was modeled on the H2 loop of D11.15.

As discussed above, CDR3s of heavy chain variable regions are highly variable and cannot be divided into identifiable structural groups. For modelling H3 loops, loops of identical length and similar amino acid sequence—preferably from another antibody—are identified and used as a basis for the modeled loop. There were three loops, all H3 loops from three antibodies, which matched the Act-1 CDR3 for loop size. After testing all three loop structures for steric clashes on the model, the H3 loop from the human antibody Pot (Fan, Z. C., et al., *J. Mol. Biol.* 228:188-207 (1992)) was chosen to model the H3 loop of mAb Act-1. After adjusting the whole of the model for obvious steric clashes it was subjected to energy minimization as implemented in QUANTA.

Designing the CDR-grafted Variable Regions

The first step in designing CDR-grafted variable regions is the selection of the human light and heavy chain variable regions that will serve as the basis of the humanized variable regions. Two approaches for selecting the human variable regions were tested and compared. In one approach, the human variable regions were selected from the consensus sequences for the different subgroups of human variable regions (Kabat, E. A., et al., *Sequences of Proteins of Immunological Interest*, Fifth Edition, U.S. Department of Health and Human Services, U.S. Government Printing Office (1991)). The rodent light and heavy chain variable regions were compared to the human consensus sequences and the most similar human light and heavy chain consensus sequences were selected from among the six subgroups of human lambda light chain variable regions, the four subgroups of human kappa light chain variable regions, and the three subgroups of human heavy chain variable regions (see Kettleborough, C. A., *Protein Engineering* 4:773-783 (1991)). In another approach, the human variable regions were selected from all published sequences for human variable regions (Kabat, E. A., et al., *Sequences of Proteins of Immunological Interest*, Fifth Edition, U.S. Department of Health and Human Services, U.S. Government Printing Office (1991)). The amino acid sequences of rodent light and heavy chain variable regions were compared to human sequences, and human variable regions with a high degree of similarity to the rodent variable regions were selected. Human light and heavy chain variable regions from the same human antibody can be used in order to ensure that the two variable regions will assemble properly (Queen, C., et al., *Proc. Natl. Acad. Sci., USA* 86:10029-10033 (1989)). However, as described herein, the human light and heavy chain variable regions selected as the templates were derived from two different human antibodies. In this way, it was possible to select for human variable regions with a higher degree of similarity to the rodent variable regions. There are many successful examples of CDR-grafted antibodies based on variable regions derived from two different human antibodies. One of the best studied examples is reshaped human CAMPATH-1 antibody (Riechmann, L., et al., *Nature* 332: 323-327 (1988)).

To design reshaped human ACT-1 variable regions, the mouse ACT-1 variable regions were compared to the consensus sequences for all subgroups of mouse and human variable regions (Kabat, E. A., et al., *Sequences of Proteins of Immunological Interest*, Fifth Edition, U.S. Department of Health and Human Services, U.S. Government Printing Office (1991)). The results are summarized in Tables 1 and 2.

The mouse Act-1 light chain variable region was most similar to the consensus sequence for mouse kappa light chain subgroup II with a 83.9% identity overall and a 87.5% identity within the FRs only (Table 1). With respect to human antibody sequences, the mouse Act-1 light chain variable region was most similar to the consensus sequence for human kappa light chain subgroup II with a 72.3% identity overall and a 78.8% identity within the FRs only (Table 1).

TABLE 1

Comparison of mouse Act-1 kappa light chain variable region to the consensus sequences for the subgroups of mouse and human kappa light chain variable regions. The amino acid sequence of the mouse Act-1 kappa light chain variable region was compared, with and without the sequences of the CDRs, to the consensus sequences of the different subgroups of mouse and human kappa light chain variable regions, with and without the sequences of the CDRs. The percents similarity and identity to the most similar mouse and human subgroups are listed.

| Mouse or Human Variable Region | Kabat Subgroup | Complete Variable Region or FRs only | Percent Similarity | Percent Identity |
|---|---|---|---|---|
| Mouse | II | Complete | 91.07 | 83.93 |
|  |  | FRs only | 95.00 | 87.50 |
| Human | II | Complete | 83.93 | 72.32 |
|  |  | FRs only | 90.00 | 78.75 |

The mouse Act-1 heavy chain variable region was most similar to the consensus sequence for mouse heavy chain subgroup IIB with a 83.5% identity overall and a 94.3% identity within the FRs only (Table 2). With respect to human antibody sequences, the mouse Act-1 heavy chain variable region was most similar to the consensus sequence for human heavy chain subgroup I with a 68.6% identity overall, and a 75.9% identity within the FRs only (Table 2). These results confirm that the mouse Act-1 variable regions appear to be typical of mouse variable regions. The results also indicate subgroups of human variable regions which can serve as good sources for human variable region templates or acceptors for CDR-grafting.

TABLE 2

Comparison of mouse Act-1 heavy chain variable region to the consensus sequences for the subgroups of mouse and human heavy chain variable regions. The amino acid sequence of the mouse Act-1 heavy chain variable region was compared, with and without the sequences of the CDRs, to the consensus sequences of the different subgroups of mouse and human heavy chain variable regions, with and without the sequences of the CDRs. The percents similarity and identity to the most similar mouse and human subgroups are listed.

| Mouse or Human Variable Region | Kabat Subgroup | Complete Variable Region or FRS only | Percent Similarity | Percent Identity |
|---|---|---|---|---|
| Mouse | IIB | Complete | 89.26 | 83.47 |
|  |  | FRs only | 95.40 | 94.25 |
| Human | I | Complete | 81.82 | 68.60 |
|  |  | FRs only | 85.06 | 75.86 |

The mouse Act-1 variable regions were also compared to the individual sequences of all recorded examples of mouse and human variable regions (Kabat, E. A., et al., *Sequences of Proteins of Immunological Interest*, Fifth Edition, U.S. Department of Health and Human Services, U.S. Government Printing Office (1991); UW GCG package (Univeriority of Wisconsin)). With respect to human antibody sequences, the mouse Act-1 light chain variable region was very similar to the sequence for the human kappa light chain variable region from human antibody GM607'CL (Klobeck, H.-G., et al., *Nature* 309:73-76 (1984)). FIG. 5 shows an alignment of the amino acid sequences of the mouse Act-1 light chain variable region (SEQ ID NO:7) and of the human GM607'CL light chain variable region (SEQ ID NO:8). As expected, the light chain variable region of human GM607'CL is a member of subgroup II of human kappa light chain variable regions. The overall sequence identity between the mouse Act-1 and human GM607'CL light chain variable regions was calculated to be 71.4%. The mouse Act-1 heavy chain variable region was very similar to the sequence for the human heavy chain variable region from human antibody 21/28'CL (Dersimonian, H., et al., *J. Immunol.* 139:2496-2501 (1987)). FIG. 6 shows an alignment of the amino acid sequences of the mouse Act-1 heavy chain variable region (SEQ ID NO:9) and of the human 21/28'CL heavy chain variable region (SEQ ID NO:10). As expected, the heavy chain variable region of human 21/28'CL is a member of subgroup I of human heavy chain variable regions. The overall sequence identity between the mouse Act-1 and human 21/28'CL heavy chain variable regions was calculated to be 68.1%. Based on these comparisons, human GM607'CL light chain variable region was selected as the human template for the design of reshaped human Act-1 light chain variable region, and human 21/28'CL heavy chain variable region was selected as the human template for the design of reshaped human Act-1 heavy chain variable region.

The second step in the design process was to insert the rodent CDRs into the selected human light and heavy chain variable regions. The entire rodent CDRs, as defined by Kabat, E. A., et al., *Sequences of Proteins of Immunological Interest*, Fifth Edition, U.S. Department of Health and Human Services, U.S. Government Printing Office (1991)), were joined to the human FRs to create a simple CDR-graft. In some cases, a rodent antibody that is humanized in a simple CDR graft will show little or no binding to antigen. It is important to study the amino acid sequences of the human FRs to determine if any of these amino acid residues are likely to adversely influence binding to antigen, either directly through interactions with antigen, or indirectly by altering the positioning of the CDR loops.

In the third step, decisions were made as to which amino acid residues in the human FRs should be altered in order to achieve good binding to antigen. At this stage, the model of the rodent variable regions becomes most useful in the design process. Also useful are the canonical structures for the CDRs as defined by Chothia, C., et al., *Nature* 342:877-883 (1989). It is important to conserve in the humanized variable regions any of the rodent amino acid residues that are part of the canonical structures. It is helpful to compare the sequence of the rodent antibody to be humanized to similar sequences from other rodent antibodies to determine if the amino acids at certain positions are unusual or rare. This might indicate that the rodent amino acid at that position has an important role in antigen binding. By studying the model of the rodent variable regions, it is possible to predict whether amino acids at particular positions could or could not influence antigen binding. When human variable regions from individual human antibodies are being used as the basis of the design, then it is advisable to compare the individual human sequence to the consensus sequence for that subgroup of human variable regions. Any amino acids that are particularly unusual should be noted. In most cases, a few amino acids in the human FRs are identified that should be changed from the amino acid present at that position in the human variable region to the amino acid present at that position in the rodent variable region.

Tables 3 and 4 summarize how the reshaped human Act-1 variable regions were designed. Table 3 is an alignment of amino acid sequences used in the design of reshaped human mAb Act-1 $V_L$ regions, and lists the amino acid sequence of the mouse Act-1 light chain variable region to be humanized (SEQ ID NO:7) in column 4, the consensus sequence for the subgroup of mouse variable regions to which the mouse Act-1 variable region belongs (SEQ ID NO:50) in column 5 (Mouse κ-II), the consensus sequence for the subroup of human variable regions to which the mouse Act-1 variable is most similar (SEQ ID NO:51) in column 6 (Human κ-II), the amino acid sequence of the human variable region that is serving as a template (i.e., GM607'CL) (SEQ ID NO:8) in column 7, and the amino acid sequence of the reshaped human Act-1 variable region (SEQ ID NO:52) as designed in column 8 (Act-1 $RHV_H$). Table 4 an the alignment of amino acid sequences used in the design of reshaped human mAb Act-1 $V_H$ regions and lists the amino acid sequence of the mouse Act-1 heavy chain variable region to be humanized (SEQ ID NO:9) in column 4, the consensus sequence for the subgroup of mouse variable regions to which the mouse Act-1 variable region belongs (SEQ ID NO:53) in column 5 (Mouse IIB), the consensus sequence for the subgroup of human variable regions to which the mouse Act-1 is most similar (SEQ ID NO:54) in column 6 (Human I), the amino acid sequence of the human variable region that is serving as a template (i.e., 21/28'CL) (SEQ ID NO:10) in column 7, and the amino acid sequence of the reshaped Act-1 variable region (SEQ ID NO:55) as designed in column 8 (Act-1 $RHV_H$). The penultimate column in Tables 3 and 4 indicates the position (surface or buried) of residues in the FRs that differ between the mouse Act-1 and the selected human FRs. The final column in Tables 3 and 4 lists comments relevant to that position in the variable region.

In Table 3, the following symbols are used: (*) invariant residues as defined either by the Kabat consensus sequences i.e. 95% or greater occurrence within Kabat subgroup (Kabat, E. A., et al., *Sequences of Proteins of Immunological Interest*, Fifth Edition, U.S. Department of Health and Human Services, U.S. Government Printing Office (1991)) (in the case of columns 5 and 6) or as part of the canonical structure for the CDR loops (in the case of columns 5 and 6) or as part of the canonical structure for the CDR loops (in the case of column 8) as defined by Chothia, C., et al., *Nature* 342:877-883 (1989); (BOLD) positions in FRs and CDRs where the human amino acid residue was replaced by the corresponding mouse residue; (UNDERLINE) positions in FRs where the human residue differs from the analogous mouse residue number; (ε) numbering of changes in the human FRs; (mouse Ab Act-1) amino acid sequence of the $V_L$ region from mouse Act-1 antibody; (mouse κ-II) consensus sequence of mouse kappa $V_L$ regions from subgroup II (Kabat, E. A., et al., supra); (human κ-II) consensus sequence of human $V_L$ regions from subgroup II (Kabat, E. A., et al., supra); (GM607'CL) amino acid sequence from human GM607'CL antibody (Klobeck, H.-G., et al., *Nature* 309:73-76 (1984)); (Surface or Buried) position of amino acid in relation to the rest of the residues in both chains of the antibody variable regions; (Act-1 RH $V_K$) amino acid sequence of the reshaped human mAb Act-1 $V_L$ region.

TABLE 3

Alignment of amino acid sequences used in the design of reshaped human mAb Act-1 $V_L$ regions.

| Kabat | # | FR or CDR | Mouse Act-1 (SEQ ID NO: 7) | Mouse κ-II (SEQ ID NO: 50) | Human κ-II (SEQ ID NO: 51) | GM 607 CL (SEQ ID NO: 8) | Act-1 or RH Vκ (SEQ ID NO: 52) | Surface or Buried | Comment |
|---|---|---|---|---|---|---|---|---|---|
| 1 | 1 | FR1 | D | D* | D* | D | D | | |
| 2 | 2 | | I | V | I* | I | V | buried | Canonical AA for L1 loop (Δ1). |
| 3 | 3 | | I | V | V* | V | V | | |
| 4 | 4 | | I | V | M | M | M | buried | Buried between L1 and L2. V = 9/245, M = 202/245 in mouse κ-II. M = 42/45, V not seen in human κ-II. If binding is poor, consider changing this to Val in second version. |
| 5 | 5 | | I | T | T* | T* | T | T | |
| 6 | 6 | | I | Q | Q* | Q* | Q | Q | |
| 7 | 7 | | I | T | T | S | S | S | surface | Distal to binding site (BS). T = 164/245 in mouse κ-II. T = 10/37, S = 27/37 in human κ-II. |
| 8 | 8 | | I | P | P | P* | P | P | |
| 9 | 9 | | I | L | L | L* | L | L | |
| 10 | 10 | | I | S | S | S* | S | S | |
| 11 | 11 | | I | L | L | L* | L | L | |
| 12 | 12 | | I | P | P | P | P | P | |
| 13 | 13 | | I | V | V* | V* | V | V | |
| 14 | 14 | | I | S | S | T* | T | T | surface | Distal to BS. S = 151/248 in mouse κ-II. T alone (30/30) seen in human κ-II. |
| 15 | 15 | | I | F | L | P | P | P | surface | Distal to BS. F = 9/253 in mouse κ-II, F not seen in human κ-II. P = 29/31 in human κ-II. |
| 16 | 16 | | I | G | G* | G* | G | G | |
| 17 | 17 | | I | D | D | E | E | E | surface | Distal to BS. E = 18/30, D not seen in human κ-II. |
| 18 | 18 | | I | Q | Q | P* | P | P | surface | Distal to BS and on a turn. P alone (31/31) seen in human κ-II. |
| 19 | 19 | | I | V | A | A* | A | A | buried | Pointing into core, but standard mouse to human change. V = 66/253, A = 187/253 in mouse κ-II. A alone (30/30) seen in human κ-II. |
| 20 | 20 | | I | S | S* | S* | S | S | |
| 21 | 21 | | I | I | I* | I* | I | I | |
| 22 | 22 | | I | S | S* | S* | S | S | |
| 23 | 23 | FR1 | C | C* | C* | C | C | |
| 24 | 24 | CDR1 | R | R | R | R | R | |
| 25 | 25 | | I | S | S* | S* | S | S | Canonical AA for L1 loop. |
| 26 | 26 | | I | S | S* | S* | S | S | Canonical AA for L1 loop. |
| 27 | 27 | | I | Q | Q | Q | Q | Q | Canonical AA for L1 loop. |
| 27A | 28 | | I | S | S | S | S | S | Canonical AA for L1 loop. |
| 27B | 29 | | I | L | L | L* | L | L | Canonical AA for L1 loop. |
| 27C | 30 | | I | A | V | L | L | A | Canonical AA for L1 loop. |
| 27D | 31 | | I | K | H | H | H | K | Canonical AA for L1 loop. |
| 27E | 32 | | I | S | S | S | S | S | Canonical AA for L1 loop. |
| 27F | | | I | — | — | X | — | — | |
| 28 | 33 | | I | Y | N | D | N | Y | Canonical AA for L1 loop. |

TABLE 3-continued

Alignment of amino acid sequences used in the design of reshaped human mAb Act-1 V_L regions.

| Kabat | # | FR or CDR | Mouse Act-1 (SEQ ID NO: 7) | Mouse κ-II (SEQ ID NO: 50) | Human κ-II (SEQ ID NO: 51) | GM 607 CL (SEQ ID NO: 8) | Act-1 or RH Vκ (SEQ ID NO: 52) | Surface or Buried | Comment |
|---|---|---|---|---|---|---|---|---|---|
| 29 | 34 | I | G | G* | G | G | G | | Canonical AA for L1 loop. |
| 30 | 35 | I | N | N | N | Y | N | | Canonical AA for L1 loop. |
| 31 | 36 | I | T | T* | N | N | T | | Canonical AA for L1 loop. |
| 32 | 37 | I | Y | Y* | Y* | Y | Y | | Canonical AA for L1 loop. |
| 33 | 38 | I | L | L* | L* | L | L | | Canonical SS for L1 loop. |
| 34 | 39 | CDR1 | S | E | N | D | S | | Packing AA. Unusual (117/1365). A, H and N most commonly seen here. |
| 35 | 40 | FR2 | W | W* | W* | W | W | | |
| 36 | 41 | I | Y | Y | Y | Y | Y | | Packing AA. Most common AA. |
| 37 | 42 | I | L | L* | L | L | L | | |
| 38 | 3 | I | H | Q* | Q | Q | Q | buried | Packing AA. H is unusual (31/1312). Q is most common AA (1158/1312). H = 6/225, Q = 219/225 in mouse κ-II. Q = 15/17, H not seen in human κ-II. |
| 39 | 44 | I | K | K | K | K | K | | |
| 40 | 45 | I | P | P* | P | P | P | | |
| 41 | 46 | I | G | G* | G* | G | G | | |
| 42 | 47 | I | Q | Q* | Q | Q | Q | | |
| 43 | 48 | I | S | S* | S | S | S | | |
| 44 | 49 | I | P | P* | P* | P | P | | Packing AA. Most common AA. |
| 45 | 50 | I | Q | K | Q | Q | Q | | |
| 46 | 51 | I | L | L | L | L | L | | Packing AA. Most common AA. |
| 47 | 52 | I | L | L* | L | L | L | | |
| 48 | 53 | I | I | I* | I* | I | I | | Canonical AA for L2 loop. |
| 49 | 54 | FR2 | Y | Y | Y* | Y | Y | | |
| 50 | 55 | CDR2 | G | K | L | L | G | | Canonical AA for L2 loop. |
| 51 | 56 | I | I | V | V | G | I | | Canonical AA for L2 loop. |
| 52 | 57 | I | S | S* | S* | S | S | | Canonical AA for L2 loop. |
| 53 | 58 | I | N | N | N | N | N | | |
| 54 | 59 | I | R | R | R* | R | R | | |
| 55 | 60 | I | F | F | A | A | F | | |
| 56 | 61 | CDR2 | S | S* | S* | S | S | | |
| 57 | 62 | FR3 | G | G* | G* | G | G | | |
| 58 | 63 | I | V | V* | V* | V | V | | |
| 59 | 64 | I | P | P | P* | P | P | | |
| 60 | 65 | I | D | D* | D | D | D | | |
| 61 | 66 | I | R | R* | R | R | R | | |
| 62 | 67 | I | F | F* | F* | F | F | | |
| 63 | 68 | I | S | S | S* | S | S | | |
| 64 | 69 | I | G | G* | G | G | G | | Canonical AA for L2 loop. |
| 65 | 70 | I | S | S* | S* | S | S | | |
| 66 | 71 | I | G | G* | G* | G | G | | |
| 67 | 72 | I | S | S* | S | S | S | | |
| 68 | 73 | I | G | G* | G | G | G | | |
| 69 | 74 | I | T | T* | T* | T | T | | |
| 70 | 75 | I | D | D | D | D | D | | |
| 71 | 76 | I | F | F* | F* | F | F | | Canonical AA for L1 loop. |
| 72 | 77 | I | T | T* | T* | T | T | | |
| 73 | 78 | I | L | L* | L* | L | L | | |
| 74 | 79 | I | K | K | K | K | K | | |
| 75 | 80 | I | I | I* | I* | I | I | | |
| 76 | 81 | I | S | S | S | S | S | | |
| 77 | 82 | I | T | R* | R | R | R | surface | Distal to BS. T = 6/221, R = 211/221 in mouse k-II. R = 11/12, T not seen in human κ-II. |
| 78 | 83 | I | I | V | V* | V | V | buried | Pointing into core, but standard mouse to human change. I = 6/213, V = 195/213 in mouse κ-II. V alone (12/12) seen in human κ-II. |

TABLE 3-continued

Alignment of amino acid sequences used in the design of reshaped human mAb Act-1 V$_L$ regions.

| Kabat | # | FR or CDR | Mouse Act-1 (SEQ ID NO: 7) | Mouse κ-II (SEQ ID NO: 50) | Human κ-II (SEQ ID NO: 51) | GM 607 CL (SEQ ID NO: 8) | Act-1 or RH Vκ (SEQ ID NO: 52) | Surface or Buried | Comment |
|---|---|---|---|---|---|---|---|---|---|
| 79 | 84 | I | K | E | E | E | E | surface | Distal to BS. K = 20/215, E = 191/215 in mouse κ-II. E = 9/12, K not seen in human κ-II. |
| 80 | 85 | I | P | A* | A | A | A | surface | Distal to BS. P = 6/183, A = 175/183 in mouse κ-II. P = 1/12, A = 11/12 in human κ-II. |
| 81 | 86 | I | E | E* | E | E | E | | |
| 82 | 87 | I | D | D* | D | D | D | | |
| 83 | 88 | I | L | L | V* | V | V | half buried | Distal to BS. V alone (12/12) seen in human κ-II. |
| 84 | 89 | I | G | G* | G* | G | G | | |
| 85 | 90 | I | M | V | V* | V | V | half buried | Distal to BS. M = 6/212, V = 196/212 in mouse κ-II. V alone (12/12) seen in human κ-II. |
| 86 | 91 | I | Y | Y* | Y* | Y | Y | | |
| 87 | 92 | I | Y | Y | Y* | Y | Y | | Packing AA. Most common AA. |
| 88 | 93 | FR3 | C | C* | C* | C | C | | |
| 89 | 94 | CDR3 | L | F | M* | M | L | | Packing AA. L is unusual (93/1238). Q is most common AA (654/1238). |
| 90 | 95 | I | Q | Q* | Q | Q | Q | | Canonical AA for L3 loop. |
| 91 | 96 | I | G | G | A | A | G | | Canonical for L3/Packing AA. 3$^{rd}$ most common AA. |
| 92 | 97 | I | T | T | L | L | T | | Canonical AA for L3 loop. |
| 93 | 98 | I | H | H | Q | Q | H | | Canonical AA for L3 loop. |
| 94 | 99 | I | Q | V | X | T | Q | | Canonical AA for L3 loop. |
| 95 | 100 | I | P | P* | P | P | P | | Canonical AA for L3 loop. |
| 95A | | I | — | P | R* | — | — | | |
| 95B | | I | — | — | — | — | — | | |
| 95C | | I | — | — | — | — | — | | |
| 95D | | I | — | — | — | — | — | | |
| 95E | | I | — | — | — | — | — | | |
| 95F | | I | — | — | — | — | — | | |
| 96 | 101 | I | Y | Y | X | Q | Y | | Packing AA. 2$^{nd}$ most common AA. |
| 97 | 102 | CDR3 | T | T* | T* | T | T | | Canonical for L3. |
| 98 | 103 | FR4 | F | F* | F* | F | F | | Packing AA. Most common AA. |
| 99 | 104 | I | G | G* | G* | G | G | | |
| 100 | 105 | I | G | G | Q | Q | Q | half buried | Distal to BS. Q = 12/13, G = 1/12 in human κ-II. |
| 101 | 106 | I | G | G* | G* | G | G | | |
| 102 | 107 | I | T | T* | T* | T | T | | |
| 103 | 108 | I | K | K* | K | K | K | | |
| 104 | 109 | I | L | L* | V | V | V | half buried | Distal to BS. L = 5/14, V = 9/14 in human κ-II. |
| 105 | 110 | I | E | E* | E | E | E | | |
| 106 | 111 | I | I | I | I* | I | I | | |
| 106A | | I | — | — | — | — | — | | |
| 107 | 112 | FR4 | K | K* | K | K | K | | |

In Table 4, the following symbols are used: (*) invariant residues as defined either by the Kabat consensus sequences i.e. 95% or greater occurrence within Kabat subgroup (Kabat, E. A., et al., *Sequences of Proteins of Immunological Interest*, Fifth Edition, U.S. Department of Health and Human Services, U.S. Government Printing Office (1991)) (in the case of columns 5 and 6) or as part of the canonical structure for the CDR loops (in the case of column 8) as defined by Chothia, C., et al., *Nature* 342:877-883 (1989); (BOLD) positions in FRs and CDRs where the human amino acid residue was replaced by the corresponding mouse residue; (UNDERLINE) positions in FRs where the human residue differs from the analogous mouse residue number; (D) numbering of changes in the human FRs; (mouse Ab Act-1) amino acid sequence of the V$_H$ region from mouse Act-1 antibody; (mouse IIB) consensus sequence of mouse V$_H$ regions from subgroup IIB (Kabat, E. A., et al., supra); (human I) consensus sequence of human V$_H$ regions from subgroup I (Kabat, E. A., et al., supra); (human 21/28'CL amino acid sequence from human antibody 21/28'CL (Dersimonian, H., et al., *J. Immunol.* 139:2496-2501 (1987)); (Surface or Buried) position of amino acid in relation to the rest of the residues in both chains of the antibody variable regions; (Act-1 RH V$_H$) amino acid sequence of the reshaped human mAb Act-1 V$_H$ region.

TABLE 4

Alignment of amino acid sequences used in the design of reshaped human mAb Act-1 V$_H$ regions.

| Kabat | # | FR or CDR | Mouse Act-1 (SEQ ID NO: 9) | Mouse IIB (SEQ ID NO: 53) | Human I (SEQ ID NO: 54) | human donor 21/28CL (SEQ ID NO: 10) | Act-1 RH V$_H$ (SEQ ID NO: 55) | Surface or Buried | Comment |
|---|---|---|---|---|---|---|---|---|---|
| 1 | 1 | FR1 | Q | Q | Q | Q | Q | | |
| 2 | 2 | | V | V* | V | V | V | | |
| 3 | 3 | | Q | Q* | Q* | Q | Q | | |
| 4 | 4 | | L | L* | L* | L | L | | |
| 5 | 5 | | Q | Q | V | V | V | surface | Distal to binding site (BS). Q = 135/143 in mouse IIB. V = 49/53, Q = 1/53 in human I. |
| 6 | 6 | | Q | Q | Q | Q | Q | | |
| 7 | 7 | | P | P | S* | S | S | half buried | Distal to BS. P = 102/150 in mouse IIB. P not seen in human I. |
| 8 | 8 | | G | G* | G* | G | G | | |
| 9 | 9 | | A | A | A | A | A | | |
| 10 | 10 | | E | E | E | E | E | | |
| 11 | 11 | | L | L* | V | V | V | surface | Distal to BS. V = 50/54, L = 4/54 in human I. |
| 12 | 12 | | V | V* | K | K | K | buried | Pointing into core, but standrd mouse to human change. K = 41/55, V = 3/55 in human I. |
| 13 | 13 | | K | K | K* | K | K | | |
| 14 | 14 | | P | P* | P* | P | P | | |
| 15 | 15 | | G | G* | G* | G | G | | |
| 16 | 16 | | T | A | A | A | A | surface | Distal to BS. T = 12/139, A = 117/139 in mouse IIB. T = 1/52, A = 23/52 in human I. |
| 17 | 17 | | S | S* | S* | S | S | | |
| 18 | 18 | | V | V* | V | V | V | | |
| 19 | 19 | | K | K | K | K | K | | |
| 20 | 20 | | L | L | V | V | V | buried | Pointing into core, but standrd mouse to human change. L = 138/179 in mouse IIB. V = 36/52, L = 1/52 in human I. |
| 21 | 21 | | S | S* | S | S | S | | |
| 22 | 22 | | C | C* | C* | C | C | | |
| 23 | 23 | | K | K* | K | K | K | | |
| 24 | 24 | | G | A* | A | A | G | buried | Canonical AA for H1 loop (Δ1). G not seen in mouse IIB. G = 12/51, A = 34/51 in human I. |
| 25 | 25 | | Y | S* | S* | S | S | surface | Pointing away from BS and so does not appear to bind antigen (Ag). Y = 1/185 in mouse IIB. S = 48/50, Y not seen in human I. |
| 26 | 26 | | G | G* | G* | G | G | | Canonical AA for H1 loop. |
| 27 | 27 | | Y | Y | Y | Y | Y | | Canonical AA for H1 loop. |
| 28 | 28 | | T | T | T | T | T | | Canonical AA for H1 loop. |
| 29 | 29 | | F | F* | F* | F | F | | Canonical AA for H1 loop. |
| 30 | 30 | FR1 | T | T | T | T | T | | Canonical AA for H1 loop. |
| 31 | 31 | CDR1 | S | S | S | S | S | | Canonical AA for H1 loop. |
| 32 | 32 | | Y | Y | Y | Y | Y | | Canonical AA for H1 loop. |
| 33 | 33 | | W | W | A | A | W | | |
| 34 | 34 | | M | M | I | M | M | | Canonical AA for H1 loop. |

TABLE 4-continued

Alignment of amino acid sequences used in the design of reshaped human mAb Act-1 $V_H$ regions.

| Kabat | # | FR or CDR | Mouse Act-1 (SEQ ID NO: 9) | Mouse IIB (SEQ ID NO: 53) | Human I (SEQ ID NO: 54) | human donor 21/28CL (SEQ ID NO: 10) | Act-1 RH $V_H$ (SEQ ID NO: 55) | Surface or Buried | Comment |
|---|---|---|---|---|---|---|---|---|---|
| 35 | 35 | I | H | H | S | H | H | | Packing AA. Most common AA. |
| 35A | | I | — | — | — | | | | |
| 35B | | CDR1 | — | — | — | | | | |
| 36 | 36 | FR2 | W | W* | W* | W | W | | |
| 37 | 37 | I | V | V | V | V | V | | Packing AA. Most common AA. |
| 38 | 38 | I | K | K | R* | R | R | buried | Pointing into core, but standard mouse to human change. K = 177/188 in mouse IIB. R = 48/49, K not seen in human I. However, Lys maybe packing H2 loop, therefore consider changing in second version, in conjunction with A40R, if binding poor. |
| 39 | 39 | I | Q | Q | Q* | Q | Q | | Packing AA. Most common AA. |
| 40 | 40 | I | R | R | A | A | A | buried | Pointing into core, but standard mouse to human change. R = 160/177 in mouse IIB. A = 37/49, R = 0/49 in human I. However, Arg maybe packing H2 loop, therefore consider changing in second version, in conjunction with A38K, if binding poor. |
| 41 | 41 | I | P | P | P | P | P | | |
| 42 | 42 | I | G | G | G | G | G | | |
| 43 | 43 | I | Q | Q | Q | Q | Q | | |
| 44 | 44 | I | G | G | G | R | R | buried | Pointing into core, but standard mouse to human change. G = 43/48, R = 5/48 in human I. |
| 45 | 45 | I | L | L* | L* | L | L | | Packing AA. Most common AA. |
| 46 | 46 | I | E | E* | E* | E | E | | |
| 47 | 47 | I | W | W* | W* | W | W | | Packing AA. Most common AA. |
| 48 | 48 | I | I | I* | M | M | I | buried | Ile Underneath and supporting H2 loop (Δ2). Met = 41/48, Ile = 1/48 in human I. |
| 49 | 49 | FR2 | G | G* | G | G | G | | |
| 50 | 50 | CDR2 | E | R | W | W | E | | |
| 51 | 51 | I | I | I | I | I | I | | |
| 52 | 52 | I | D | D | N | N | D | | |
| 52A | 53 | I | P | P* | P | A | P | | Canonical AA for H2 loop. |
| 52B | | I | — | — | Y | — | | | |
| 52C | | I | — | — | — | — | | | |
| 53 | 54 | I | S | N | G | G | S | | Canonical AA for H2 loop. |
| 54 | 55 | I | E | S | N | N | E | | Canonical AA for H2 loop. |
| 55 | 56 | I | S | G | G | G | S | | Canonical AA for H2 loop. |
| 56 | 57 | I | N | G | D | N | N | | |
| 57 | 58 | I | T | T | T | T | T | | |
| 58 | 59 | I | N | N | N | K | N | | |
| 59 | 60 | I | Y | Y | Y | Y | Y | | |
| 60 | 61 | I | N | N | A | S | N | | |

TABLE 4-continued

Alignment of amino acid sequences used in the design of reshaped human mAb Act-1 V$_H$ regions.

| Kabat | # | FR or CDR | Mouse Act-1 (SEQ ID NO: 9) | Mouse IIB (SEQ ID NO: 53) | Human I (SEQ ID NO: 54) | human donor 21/28CL (SEQ ID NO: 10) | Act-1 RH V$_H$ (SEQ ID NO: 55) | Surface or Buried | Comment |
|---|---|---|---|---|---|---|---|---|---|
| 61 | 62 | I | Q | E | Q | Q | Q | | |
| 62 | 63 | I | K | K* | K | K | K | | |
| 63 | 64 | I | F | F* | F | F | F | | |
| 64 | 65 | I | K | K | Q | Q | K | | |
| 65 | 66 | CDR2 | G | S | G | G | G | | |
| 66 | 67 | FR3 | K | K* | R | R | R | surface | Distal to BS. R = 39/49, K not seen in human I. |
| 67 | 68 | I | A | A* | V | V | V | half buried | Distal to BS. V = 45/48, A not seen in human I. |
| 68 | 69 | I | T | T* | T | T | T | | |
| 69 | 70 | I | L | L* | I | I | L | buried | Leu Underneath and supporting H2 loop (Δ3). Ile = 26/49, Leu = 1/49 in human I. |
| 70 | 71 | I | T | T* | T | T | T | | |
| 71 | 72 | I | V | V | A | R | V | buried | Canonical AA for H2 loop (Δ4). |
| 72 | 73 | I | D | D* | D | D | D | | |
| 73 | 74 | I | I | K | T | T | I | surface | Behind H2 loop and may play a direct part in Ag binding (Δ5). Ile not seen in mouse IIB or human I. T = 21/49 in human I. |
| 74 | 75 | I | S | S | S* | S | S | | |
| 75 | 76 | I | S | S* | T | A | A | surface | Distal to BS. T = 26/50, A = 4/50, S not seen in human I. |
| 76 | 77 | I | S | S | S | S | S | | |
| 77 | 78 | I | T | T* | T | T | T | | |
| 78 | 79 | I | A | A | A | A | A | | |
| 79 | 80 | I | Y | Y* | Y | Y | Y | | |
| 80 | 81 | I | M | M | M | M | M | | |
| 81 | 82 | I | Q | Q | E | E | E | half buried | Distal to BS. Q = 163/194 in mouse IIB. E = 35/50, Q = 11/50 in human I. |
| 82 | 83 | I | L | L* | L | L | L | | |
| 82A | 84 | I | S | S | S | S | S | | |
| 82B | 85 | I | S | S | S | S | S | | |
| 82C | 86 | I | L | L* | L* | L | L | | |
| 83 | 87 | I | T | T* | R | R | R | surface | Distal to BS. R = 33/51, T = 4/51 in human I. |
| 84 | 88 | I | S | S* | S | S | S | | |
| 85 | 89 | I | E | E | E | E | E | | |
| 86 | 90 | I | D | D* | D* | D | D | | |
| 87 | 91 | I | S | S* | T | T | T | surface | Distal to BS. T = 48/51, S = 2/51 in human I. |
| 88 | 92 | I | A | A* | A | A | A | | |
| 89 | 93 | I | V | V* | V | V | V | | |
| 90 | 94 | I | Y | Y* | Y* | Y | Y | | |
| 91 | 95 | I | Y | Y | Y | Y | Y | | Packing AA. Most common AA. |
| 92 | 96 | I | C | C* | C* | C | C | | |
| 93 | 97 | I | A | A | A* | A | A | | Packing AA. Most common AA. |
| 94 | 98 | FR3 | R | R | R | R | R | | Canonical AA for H1 loop. |
| 95 | 99 | CDR3 | G | Y | A | G | G | | Packing AA. 2$^{nd}$ most common residue seen at this point -OK. |
| 96 | 100 | I | G | Y | P | — | G | | |
| 97 | 101 | I | Y | Y | G | — | Y | | |
| 98 | 102 | I | D | G | Y | — | D | | |
| 99 | 103 | I | G | G | G | G | G | | |
| 100 | 104 | I | W | S | S | — | W | | |
| 100A | 105 | I | D | S | G | — | D | | |
| 100B | 106 | I | Y | X | G | — | Y | | |

TABLE 4-continued

Alignment of amino acid sequences used in the design of reshaped human mAb Act-1 V$_H$ regions.

| Kabat | # | FR or CDR | Mouse Act-1 (SEQ ID NO: 9) | Mouse IIB (SEQ ID NO: 53) | Human I (SEQ ID NO: 54) | human donor 21/28CL (SEQ ID NO: 10) | Act-1 RH V$_H$ (SEQ ID NO: 55) | Surface or Buried | Comment |
|---|---|---|---|---|---|---|---|---|---|
| 100C | 107 | | A | X | G | — | A | | |
| 100D | 108 | | I | V | C | — | I | | Packing AA. I = 26/1211. F and M are most commonly seen. |
| 100E | | | — | Y | Y | — | | | |
| 100F | | | — | X | R | Y | | | |
| 100G | | | — | — | G | Y | | | |
| 100H | | | — | Y* | D | G | | | |
| 100I | | | — | W | Y | S | | | |
| 100J | | | — | Y | X | G | | | |
| 100K | | | — | F | F | S | | | |
| 101 | 109 | | D | D | D | N | D | | |
| 102 | 110 | CDR3 | Y | Y | Y | Y | Y | | |
| 103 | 111 | FR4 | W | W* | W* | W | W | | Packing AA. Most common AA. |
| 104 | 112 | | G | G* | G | G | G | | |
| 105 | 113 | | Q | Q | Q | Q | Q | | |
| 106 | 114 | | G | G* | G* | G | G | | |
| 107 | 115 | | T | T* | T | T | T | | |
| 108 | 116 | | S | T | L | L | L | surface | Distal to BS. T = 88/149 in mouse IIB. L = 25/39, T = 7/39 in human I. |
| 109 | 117 | | V | V | V* | V | V | | |
| 110 | 118 | | T | T* | T | T | T | | |
| 111 | 119 | | V | V* | V | V | V | | |
| 112 | 120 | | S | S* | S* | S | S | | |
| 113 | 121 | FR4 | S | S | S* | S | S | | |

With respect to the design of reshaped human Act-1 light chain variable region (Table 3), one residue in the human FRs was changed from the amino acid present in the human FRs to the amino acid present in the original mouse FRs. This change was at position 2 in FR1 (as defined by Kabat, E. A., et al., *Sequences of Proteins of Immunological Interest*, Fifth Edition, U.S. Department of Health and Human Services, U.S. Government Printing Office (1991)). In particular, the isoleucine found in human GM607'CL light chain variable region was changed to valine as found in mouse Act-1 light chain variable region. This position in the kappa light chain variable region has been identified by Chothia, C., et al., *Nature* 342: 877-883 (1989) as one of the locations that is critical for the correct orientation and structure of the L1 loop and, as such, is known as one of the "canonical amino acids". Due to their important role in loop conformation, such mouse framework residues are generally always conserved in the reshaped variable region.

At position 4 in FR1, there is a valine in the mouse sequence and a methionine in the human sequence. A change from a valine to a methionine is not a drastic change in itself as both amino acids are non-polar, hydrophobic residues, so the methionine present in the human sequence was used in the reshaped human Act-1 variable region. However, the model indicates that the valine is buried between the L1 and L2 loops and the mean volume of valine when buried in proteins is 142 Å$^3$, whereas methionine occupies approximately 171 Å$^3$ of space. The larger methionine residue could cause a change in the conformation of either, or both, of the L1 and L2 loops. Antigen binding of the reshaped human Act-1 may be improved by an additional change at position 4 from methionine to a valine in the reshaped human Act-1 light chain variable region.

With respect to the design of reshaped human Act-1 heavy chain variable region (Table 4), there were five residues in the human FRs which were changed from the amino acids present in the human FRs to the amino acids present in the original mouse FRs. At positions 24 in FR1 and 71 in FR3 (as defined by Kabat, E. A., et al., *Sequences of Proteins of Immunological Interest*, Fifth Edition, U.S. Department of Health and Human Services, U.S. Government Printing Office (1991)), the amino acid residues as present in the mouse sequence were retained in the reshaped human Act-1 heavy chain variable region because these positions are part of the canonical structures for the H1 and H2 loops, respectively (Chothia, C., et al., *Nature* 342:877-883 (1989)). Since any amino acid changes at these positions could disrupt the packing and the final structures of the H1 and H2 loops, mouse residues at these critical locations are routinely conserved in the humanized heavy chain variable region.

At position 48 in FR2, the methionine in the human sequence was changed to an isoleucine as present in the mouse Act-1 sequence. The substitution of a methionine for an isoleucine is unusual. More importantly, the model shows that the isoleucine residue is buried underneath the H2 loop. As a result, changes at this buried position may have influenced the structure of the H2 loop and hence interfered with antigen binding.

At position 69 in FR3, the isoleucine in the human sequence was changed to a leucine as present in the mouse Act-1 sequence. Although the substitution of a leucine for an isoleucine is not unusual, the model shows that the leucine is buried under the H2 loop. Consequently, like the residue at position 48, changes at this location could influence the conformation of the H2 loop and thereby disrupt antigen binding.

Finally, at position 73 in FR3, the threonine in the human sequence was changed to an isoleucine as present in the mouse sequence. An isoleucine at this position in FR3 has never been seen previously in mouse subgroup IIB, or human subgroup I (as defined by Kabat, E. A., et al., Fifth Edition, U.S. Department of Health and Human Services, U.S. Government Printing Office (1991)), which suggests that the isoleucine at this location may have an important role in antigen binding.

In the model, the leucine at position 73 appears to be on the surface near the edge of the binding site and, depending on the size and orientation of the epitope on the α4β7 integrin, may possibly play a direct part in antigen binding. However, as a surface residue position, the antibody as a whole would have less immunogenic potential if the mouse amino acid was not present in the reshaped human antibody. The isoleucine could be replaced with the human threonine residue in derivatives of the reshaped antibody, and the new construct re-tested to determine whether the second version maintains a similar level of antigen binding.

In addition to the five changes in the human FRs made in the original design of the reshaped human Act-1 heavy chain variable region, there were two other changes that could be made which may improve antigen binding. The model suggests that residues 38 Lys and 40 Arg in the heavy variable region of mouse mAb Act-1 are positioned underneath the H2 loop and pack close to 63 Phe in CDR2 (numbering as in Table 4). However, these residues are also located in the core of the heavy chain variable region and may have other, possibly detrimental, effects if they were used to replace their corresponding human amino acids (38 Arg and 40 Ala, respectively). Therefore, the changes to positions 38 and 40 in FR2 were not incorporated into the reshaped human heavy variable region of mAb Act-1. However, either or both modifications of the reshaped heavy chain may be used in derivatives to improve antigen binding.

Conclusions

A model of the mouse Act-1 variable regions was built based mainly on the solved structures of other antibody variable regions. The model was used in the design of humanized Act-1 variable regions. Particular emphasis was put on retaining the structure of the antigen-binding site in the reshaped human variable regions.

A reshaped human Act-1 light chain variable region and a reshaped human Act-1 heavy chain variable regions were designed (Tables 3 and 4). The reshaped human Act-1 light chain variable region was based on the CDRs of mouse Act-1 light chain variable region and on the FRs from the light chain variable region of human GM607'CL antibody. One amino acid change was made in the human FRs at position 2. The reshaped human Act-1 heavy chain variable region was based on the CDRs of mouse Act-1 heavy chain variable region and on the FRs from the heavy chain variable region of human 21/28'CL antibody. Five amino acid changes were made in the human FRs at positions 24, 48, 69, 71 and 73.

In addition, a single site at position 4 in FR1 of the kappa light chain and two sites at positions 38 and 40 in FR2 of the heavy chain were noted that might be considered in the design of additional versions of reshaped human Act-1 variable regions. Also, a single residue at position 73 in FR3 of the heavy chain was also identified as a candidate for backmutation from the mouse to the human amino acid, in view of its location on the surface of the antibody.

EXAMPLE 3

Construction of Nucleic Acids Encoding Reshaped Variable Regions

After confirming that the correct heavy chain and light chain variable regions had been cloned biochemically (partial amino acid sequence) and functionally (chimeric antibody staining of HuT 78 cells), a reshaped amino acid sequence was designed as described above. Next, genes encoding the reshaped antibody chains were designed and prepared.

Design, Construction, and Expression of Humanized ACT-1

After determining the primary amino acid sequence of the humanized antibody as described in Example 2, the sequence was reverse-translated into a degenerate nucleic acid sequence and analyzed for potential restriction enzyme sites using MacVector (Kodak, Scientific Imaging Systems) version 4.5.3. A nucleic acid sequence was then selected which incorporated restriction enzyme cleavage sites but conserved the primary amino acid sequence. The heavy chain nucleic acid sequence (SEQ ID NO:18) and amino acid sequence (SEQ ID NO:19) are shown in FIG. 11, and the light chain nucleic sequence (SEQ ID NO:20) and amino acid sequence (SEQ ID NO:21) are shown in FIG. 12 with restriction enzyme sites noted which were used in subcloning.

The humanized Act-1 heavy and light chain variable region genes were constructed as follows. Overlapping, complementary oligonucleotides, designated L1-L6 (SEQ ID NOS: 22-27, respectively) for the light chain, and H1-H10 (SEQ ID NOS:28-37, respectively) for the heavy chain were synthesized using an Applied Biosystems DNA Synthesizer Model 392 (FIG. 13). After deprotection overnight at 55° C., oligos were dried in a Speed-Vac, resuspended in 100 ml of water and desalted over Bio-Spin 6 columns (Bio-Rad). The oligo concentration was determined by measuring absorbance at 260 nm, and the oligos were purified by denaturing polyacrylamide gel electrophoresis.

100 μg of each oligo was mixed with 2 volumes of loading dye (95% formamide, 20 mM EDTA, 0.05% bromophenol blue, 0.05% xylene cyanol FF), heated for 2 minutes at 65° C., and run in 1×TBE for approximately 3 hours at 250 V. The gel was stained with ethidium bromide and observed under ultraviolet light. Oligos of correct length were then cut out of the gel, placed in dialysis tubing with water and electroeluted. The oligos were twice extracted with equal volumes of phenol/chloroform/isoamylalcohol (25:24:1 v/v) (Gibco/BRL) and precipitated by adding 0.1 volumes of 3.0 M potassium acetate (pH 6) and 2 volumes of cold ethanol. After centrifugation, the pellets were washed once with 70% ethanol, vacuum dried, and resuspended in 50 μl water.

Complementary oligos were annealed by mixing equal molar quantities (approximately 100 μg in 50 μl water) of the purified oligo with an equal volume (100 μl) of 2×annealing buffer (2×=1M NaCl, 40 mM Tris-HCl at pH 7.5, 2 mM EDTA). Oligos were denatured by heating to 95° C. for 10 minutes followed by an 8 hour incubation at 65° C. Annealed oligos were then ethanol precipitated as described previously and resuspended in 40 μl water.

Extension of the annealed oligos was accomplished by adding 2 μl Large Fragment DNA Polymerase I (Klenow), 5 μl 2.5 mM dNTPs and 5 μl 10×Buffer (10×=10 mM Tris-HCl, 10 mM $MgCl_2$, 1 mM DTT, pH 7.9 at 25° C.) bringing the final volume up to 52 μl. The mixture was incubated for one hour at room temperature. An additional 1 μl of dNTPs and 1 μl of Klenow were added with a half hour incubation at 37° C. Note that heavy chain fragment A did not have to be extended.

Annealed and extended fragments were purified from single stranded, unannealed material by electrophoresis through a 12% native polyacrylamide gel. The gel was stained with ethidium bromide and observed under ultraviolet light. The correct length fragments were cut out and recovered by electroelution in dialysis tubing as described above. The fragments were washed twice with equal volumes of phenol/chloroform/isoamyl alcohol, ethanol precipitated and resuspended in 10 µl water.

The three light chain fragments (LA, LB & LC) and five heavy chain fragments (designated HA-HE) were independently ligated into pCR-Script™ and transformed, except as described below, into XL-1 Blue Supercompetent Cells using a pCR-Script kit (Stratagene) according to the manufacturer's recommended protocol. Fragments pCR-LA and pCR-LB were transformed into DM1 (Gibco/BRL) competent cells to avoid the Dcm methylase which would block digestion with restriction enzyme Msc I. White colonies were picked, and miniprep DNA was sequenced using Sequenase T7 DNA polyemerase kit according to the manufacturer's recommended protocol. T3 and T7 primers, which anneal on opposite sides of the insert, were used for sequencing.

Compilation subcloning of the humanized heavy chain variable region and light chain variable region fragments was accomplished using specific restriction sites incorporated into the sequence during synthesis. Heavy chain fragments HA-HD include an additional Age I restriction site at the end of each sequence allowing for sequential subcloning of the fragments as described below.

Miniprep DNA from pCR-HA and pCR-HB were digested with restriction enzymes Spe I and Age I. DNA was electrophoresed on a 1% agarose gel. The 141 bp fragment HB was recovered from the gel and ligated into pCR-HA at the Spe I and Age I sites giving rise to pCR-HAB. Next, 112 bp fragment HC was released from pCR-HC using Xba I and Age I and ligated into the Xba I and Age I sites in pCR-HAB resulting in the plasmid pCR-AC. Fragments HD (141 bp) and HC (130 bp) were ligated in the same sequential fashion using restriction sites Nhe I and Age I for Fragment HD, and BstE II and Age I for fragment E. The final plasmid containing all five heavy chain variable region fragments in pCR-script was designated pCR-HAE. All digests were performed using miniprep DNA with incubations at 37° C. for at least two hours except for those using BstE II, which has an optimal incubation temperature of 65° C. Ligations were done overnight at 16° C. using T4 DNA ligase with a 1:10 vector to insert ratio and transformed the following day into DH5α subcloning efficiency competent cells (Gibco/BRL) following the manufacturer's recommended protocol.

The Act-1 humanized heavy chain variable region in pCR-Script™ was released by digestion of pCR-HAE with HindIII and Age I. This 411 bp fragment was used to replace the mouse variable region sequences of pEE6mhACT1Hchi (Example 1) which had been digested with HindIII and Age I generating the humanized ACT-1 heavy chain gene in pEE6hCMV-B. The resulting plasmid is designated pEE6hACT1H. Correct DNA sequence was determined by sequencing.

Light chain fragment A in pCR-Script™ was digested with BspE I and MscI. This 153 bp fragment was then used to replace the mouse portion from BspE I to MscI of the mouse variable light chain in pCR-script™. This plasmid is designated pCR-LhAmBC. Light chain fragment B, digested with Msc I and Nru I, and light chain fragment C, digested with Nru I and Kas I, were triple ligated into the MscI and Kas I sites of pCR-LhAmBC replacing the remaining mouse sequence. Digestions, ligations and transformations used the same procedures as previously stated except DM1 competent cells were used in all except the final transformation.

The humanized light chain variable region in pCR-Script™ and the plasmid pEE12mhACT1Lchi (Example 1) were digested with Hind III and Kas I. The 360 bp light chain variable region fragment and the 315 bp light chain constant region were gel purified and triple ligated into the Hind III restriction site of pEE12 to yield pEE12hACT1L. Sequencing was performed to confirm correct orientation and nucleic acid sequence.

An expression vector containing both the humanized heavy and light chain genes was constructed using the same method as described for the chimeric antibody (see Example 1, Expression of a Chimeric Immunoglobulin) with the following exception. Due to an additional Bgl II restriction site in the humanized variable heavy chain region, a partial digest was used when cutting with Bgl II to obtain the correct fragment. The vector containing both humanized heavy and light chain genes is designated pEE12hACT1LH.

Figure 14:
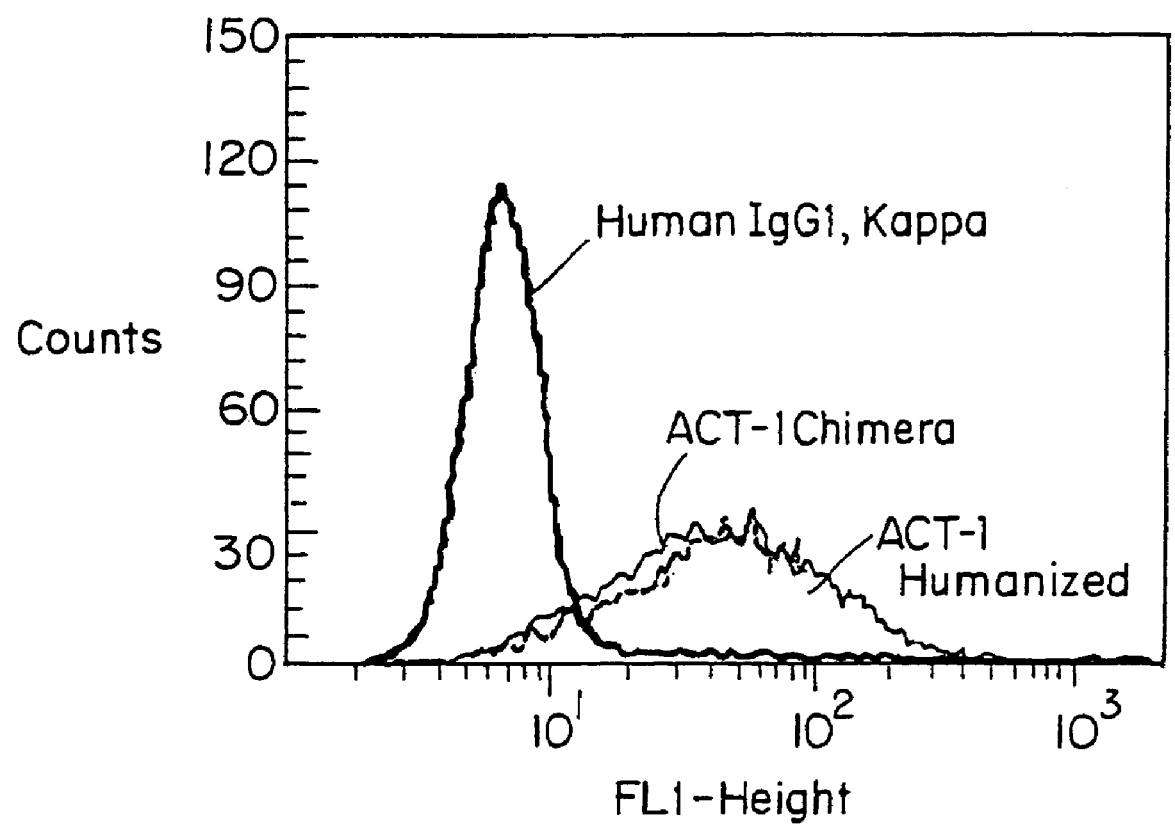
FIG. 14 is a fluorescence plot illustrating the staining of HuT 78 cells using a mouse-human Act-1 chimeric immunoglobulin, a humanized Act-1 immunoglobulin or an irrelevant, human isotype-matched control antibody (IgG1, kappa).

Transient expression of all humanized antibody constructs and cell staining was performed using the same protocols as those used for the chimeric antibody (see Example 1, Expression of a Chimeric Immunoglobulin). FIG. 14 shows the results of HuT 78 staining using the mouse-human chimeric Act-1 antibody or humanized Act-1 antibody compared to an irrelevant isotype-matched control antibody (IgG1, kappa).

Stable transfectants of NSO cells, a myeloma cell line (*Methods in Enzymol.* 73 (*B*):3-46 (1981); European Collection of Animal Cell Cultures, PHLS CAMR, Porton Down, Salisbury, Wiltshire SP4 OJG, U.K., ECACC No. 85110503) were obtained by electroporation of NSO cells with pEE12hACT1LH.

Stable Expression in NSO Cells

40 µg of pEE12hACT1LH for stable transfection was linearized by digestion with SalI restriction enzyme, which cuts within the bacterial plasmid portion of the construct. The linearized DNA was precipitated from solution using two volumes ethanol plus 1/10 volume sodium acetate, washed in 70% ethanol, dried and resuspended in sterile water.

Exponentially growing NSO cells were maintained in Non-Selective Medium (Dulbecco's Modified Eagles' Medium (high glucose), with 2 mM L-glutamine, without sodium pyruvate, with 4500 mg/L glucose, and with 25 mM HEPES buffer (GIBCO/BRL, Catalog No. 12430-021), plus 10% Fetal Bovine Serum (Gibco/BRL, Catalog No. 16000-044)). NSO cells were centrifuged, washed and resuspended in cold PBS, such that after the addition of the DNA the cells would be at a concentration of $10^7$ cells/ml. The linearized plasmid DNA (40 µg) was added to $10^7$ cells in an electroporation cuvette on ice. The cells and DNA were mixed gently so as to avoid generating bubbles and the mixture was left on ice for 10 minutes. The outside of the cuvette was wiped dry and two consecutive pulses at 1500V, 3 µF were delivered using a Gene Pulser (Bio-Rad). The cuvette was returned to ice for 10 minutes.

Transfected cells were transferred to 96 well plates at densities of $3 \times 10^5$, $7.5 \times 10^4$ and $1.5 \times 10^4$ cells/ml in 50 µl of non-selective medium and incubated at 37° C. for 24 hours. Subsequently 150 µl of Selective Medium (Glutamine Free Dulbecco's Modified Eagle's Medium, with 4500 mg/L glucose, with 4 mg/L pyridoxine HCl, with 110 mg/L sodium pyruvate, without ferric nitrate, without L-glutamine (JRH BioSciences, Catalog No. 51435-78P), plus 1×GS Supplement (50×GS Supplement obtained from JRH Bioscience, Catalog No. 58672-77P), plus 10% Dialyzed Fetal Bovine Serum (Gibco/BRL, Catalog No. 26300-061)) was added to all wells. The plates were returned to the incubator until substantial cell death had occurred and discrete surviving colonies had appeared. Once colonies of glutamine-independent transfectants could be seen, wells with single colonies were selected and spent tissue culture supernatants were collected and assayed for human IgG secretion by ELISA as described below. An antibody-producing clone designated 3A9, which was used in subsequent studies, was obtained in this manner. A second transfection was performed as described above, except that selection was conducted in the presence of L-methionine sulphoximine (MSX, a glutamine synthetase inhibitor).

Positive colonies were screened by ELISA for human IgG secretion as follows. ELISA plates (NUNC Maxisorp) were coated overnight at 4° C. with 100 µl of AffiniPure F(ab')$_2$ fragment donkey anti-human IgG (H+L) (Jackson ImmunoResearch Laboratories) at 2.5 µg/ml in carbonate buffer pH 9.5. Plates were washed four times with PBS Tween 20 and blocked for 2 hrs at 37° C. with 200 µl PBS, 1% BSA. Plates were washed and incubated 15 min at 37° C. with 100 µl stable transfected NSO supernatant. Human IgG1 kappa at 1 mg/ml in PBS 1% BSA was used as a standard. Fresh NSO media (DME+GS supplement) was used as a negative control. Plates were washed and incubated 15 min at 37° C. with 100 µl peroxidase-conjugated AffiniPure F(ab')$_2$ fragment donkey anti-human IgG (H+L) (Jackson ImmunoResearch Laboratories) at 0.05 µg/ml in PBS (no $Ca^{2+}/Mg^{2+}$). One 5 mg O-phenylenediamine dihydrochloride (OPD) tablet (Sigma) was dissolved in 12 ml citrate buffer (0.1M, pH 5.0), and 12 µl 30% hydrogen peroxide was added after the tablet was dissolved. After washing to remove the secondary antibody, 100 µl of dissolved OPD substrate was added. The reaction was stopped with 12.5% sulfuric acid and plates were read on a Dynatech Plate Reader at 490 nm. Positive wells were cloned by limiting dilution at 2, 1, and 0.5 cells per well. When all wells from a single cloning tested positive for antibody production by ELISA, the line was considered cloned.

Purification of humanized ACT-1 antibody from cell culture supernatants of transient or stable cell transfectant cultures were carried out by Protein A affinity chromatography (Poros A/M 4.6/100 mm, 5 mL/min using a Bio-Cad workstation (Perseptive Biosystems, Inc.). The column was equilibrated with PBS followed by the application of the cell culture supernatant which had previously been filtered through 0.2 micron filters. The volume of cell culture supernatant applied per run varied according to the concentration of antibody. Normally no more than 15 mg of antibody were applied to the column in one given run. Flow rate was 5 ml/min throughout the purification procedure. After binding, the column was washed first extensively with PBS until $OD_{280}$ nm=0. The column was then further washed with a minimum of 50 column volumes. The column was then subsequently washed with 0.1 M sodium acetate, pH 5.0. Elution was accomplished by washing with 0.1 M NaCitrate, pH 3.5. The eluate was collected in 5 ml fractions and the pH neutralized by addition of 200 µls of 1.5 M $Na_2CO_3$ pH 12. Antibody containing fractions were then pooled and concentrated to the desired concentration by ultrafiltration (centricon, 30,000 KDa cut off, Amicon).

Construction of an Fc-mutated Variant

A non-Fc binding (Fc-mutated) version of the humanized Act-1 antibody was also constructed. This antibody has the same variable regions as the humanized Act-1 antibody (FIG. 11 and FIG. 12), and an identical human IgG1 constant region, with the exception of two amino acid substitutions in the IgG1 heavy chain constant region designed to abrogate FcR$_{\gamma}$ recognition and eliminate Fc binding (i.e., a Leu$^{234}$→Ala$^{234}$ substitution and a Gly$^{237}$→Ala$^{237}$ substitution). The nucleic acid encoding the heavy chain of the Fc-mutated derivative was constructed as follows. A construct designated 3678 (obtained from Dr. Herman Waldmann, University of Oxford), which encodes the light chain and heavy chain of a humanized anti-CD18 antibody (WO 93/02191 (published Feb. 4, 1993); Sims, M. J., et al., *J. Immunol.* 151(4): 2296-2308 (1993)) in a pEE12 expression vector, but in which two amino acid substitutions were introduced into the IgG1 heavy chain constant region by site-directed mutagenesis (Leu$^{234}$→Ala$^{234}$ and Gly$^{237}$→Ala$^{237}$), was digested with Age I and EcoRI to release a 900 bp fragment containing the gamma constant region mutant. This fragment was then used to replace the heavy chain wild type gamma one constant region at the AgeI/EcoRI sites in pEE6hACT1H giving rise to pEE6hACT1H/FCmut. In a manner analagous to that described above for other constructs comprising both chains, a single construct (pEE12hACT1LH/FCmut) which contains the reshaped light chain gene and the Fc-mutated reshaped heavy chain gene was prepared.

EXAMPLE 4

Characterization of LDP-02, a Humanized ACT-1 Antibody

Initial characterization studies were performed using antibody produced from COS-7 cells transiently transfected with pEE12hACT1LH/FCmut. This antibody preparation was produced and purified as described above, and is referred to below as "1°HUM ACT-1" followed by the appropriate lot number.

Additional assays were performed using antibody produced from a stable transfectant of murine cell line NSO as described above (transfected with linearized pEE12hACT1LH/FCmut). This antibody preparation is referred to below as "LDP-02/3A9/Lot 1".

"LDP-02/3A9/Lot #1" antibody was used in the following studies described below: SDS-PAGE, Western Blot Analysis, Isoelectric Focusing, Amino Acid Composition Analysis, Species Cross-reactivity, Titration, Complement Mediated Lysis Assays, ADCC Assays, and Binding Inhibition Assays. "1°HUM ACT-1 Lot #7 was used in Affinity Assays #1-2, 1°HUM ACT-1 Lot #8/9 was used in Affinity Assays #3-5, and 1° HUM ACT-1 Lot #8/9 was used in C1q Binding Assays.

A. Physico-chemical Properties

1. SDS-PAGE

In order to assist in establishing identity, characterize the first preparation, and assess purity LDP-02/3A9/Lot#1 was subjected to sodium dodecyl sulfate polyacrylamide gel electrophoresis (SDS-PAGE) under non-reducing and reducing conditions and stained with Colloidal Coomassie Blue.

80 µl of LDP-02/3A9/Lot#1 at a nominal concentration of 0.82 mg/ml was added to a microconcentrator. The citrate buffer, in which the antibody was dissolved, was exchanged three times with 160 µl of Tris buffer (0.5 mM, pH 8.8). The final volume of the sample after buffer exchange was 135 µl, yielding a protein concentration of 0.486 mg/ml. This solution was diluted two-fold with both non-reducing and reducing buffers to obtain a concentration of 0.243 mg/ml. A 13 µl aliquot of the 0.243 mg/ml solution, containing 3.16 µg of protein, was loaded onto the designated sample lanes of the SDS gel. SDS-PAGE was performed, and control articles included Mark 12 Molecular Weight Standards (Novex, #LC5677).

Under non-reducing conditions, a major band with an apparent molecular weight of slightly lower than 200,000 Daltons was present in LDP-02/3A9/Lot#1. Several minor components were observed between 116,300 and 200,000 Daltons. Three additional minor components with approximate molecular weights of 97,400 Daltons, slightly greater than 55,400 Daltons, and less than 31,000 Daltons were also observed. Scanning the gel using a laser densitometry allowed for the quantitative analysis of the stained polypeptide bands and then calculation of percent area associated with each visible band (Table 5). The obtained data from the quantitative analysis indicates that the major component observed at approximately 200,000 Daltons represented 84.4% of the total stained bands in the test sample lane. This major band represented the intact antibody, while the other bands at 55,000 and 31,000 Daltons represented single heavy and light chains respectively.

Under reducing conditions, two major components were observed on the electrophoresis gel. The molecular weight of one of the components was approximately 55,400 Daltons and represented 68.6% of the total stained bands visualized in the gel lane, while the second component corresponding to slightly less than 31,000 Daltons, represented 30.5% of the total stained bands (Table 5). The molecular weights of these two components agree well with the expected molecular weights of the heavy and light chains of an immunoglobulin G. These data indicate that approximately 99% of the preparation consisted of either intact antibody or single heavy or light chain immunoglobulin chains. Besides the two major components, one minor component at slightly less than 66,300 Daltons was also observed.

From this analyses, a high molecular weight species consistent with that for intact immunoglobulin G is present as the major band in LDP-02/3A9/Lot#1. Several minor bands are also present in LDP-02/3A9/Lot#1. Following reduction, two major bands were observed which show electrophoretic migrations consistent with those for the heavy and light chains of an immunoglobulin G molecule.

TABLE 5

| PURITY DATA SUMMARY COLLOIDAL COOMASSIE BLUE, NON-REDUCING CONDITIONS | | |
| --- | --- | --- |
| Sample | Lane | Area Percent (Main Component) |
| LDP-02/3A9/Lot #1 | 5 | 84.4% |

| PURITY DATA SUMMARY COLLOIDAL COOMASSIE BLUE, REDUCING CONDITIONS | | | |
| --- | --- | --- | --- |
| Sample | Lane | Low M.W. Area Percent | Low M.W. Area Percent |
| LDP-02/3A9/Lot #1 | 9 | 68.6% | 30.5% |

2. Western Blot Analysis

Samples and standards were analyzed by SDS-PAGE as described above. Briefly, nonreduced and reduced samples were analyzed on a 4-20% Tris-Glycine gel. Novex Mark 12 Molecular Weight Standards were also run on the gel. Volumes of 2.1 µl and 4.5 µl aliquots of the 0.2143 mg/ml solution, yielding 0.51 and 1.09 µg of protein, respectively, were loaded onto the designated sample lanes of the SDS gel.

Following SDS-PAGE, sample protein were transferred from the gel to nitrocellulose as per Novex Western Transfer Apparatus instructions. The transfer buffer used was 1×Tris-Glycine buffer in 20% Methanol. After approximately 2 hours, the nitrocellulose blot was removed from the transfer apparatus and rinsed with DDI water. The nitrocellulose blot was then blocked at 37° C. for 35 minutes in Tris buffer (20 mM), containing 3% gelatin and 0.1% Tween 20. The blot was removed from the blocking solution and washed twice with Tris buffer. Goat anti-mouse IgG solution, which was prepared by diluting anti-mouse IgG antibody stock solution by 1000-fold with 20 mM Tris-3% BSA solution, was added to the blot and incubated at 2-8° C. overnight. Following incubation, the blot was washed with four changes of Tris buffer for 5 minutes each. Anti-goat IgG alkaline-phosphatase conjugate solution, prepared by diluting anti-goat IgG alkaline-phosphatase conjugate 5000-fold with 20 mM Tris-3% BSA solution, was added to the blot and incubated at room temperature for 2 hours. Following incubation, the blot was washed with four changes of Tris buffer for 5 minutes each. BCIP/NBT (5-Bromo-4-Chloro-3'-Indolyl Phosphate p-Toluidine salt/Nitro-Blue Tetrazolium Chloride) substrate was added 10 ml at a time to the blot. Blot was developed at room temperature with agitation. Reaction was stopped by rinsing blot with Tris buffer. The above procedure was then repeated using goat anti-human IgG instead of goat anti-mouse IgG.

Under both non-reducing and reducing conditions using the anti-mouse IgG reagent, the 0.51 µg and the 1.09 µg IgG samples were clearly detected on the nitrocellulose blot. The intensity of the bands increased with increasing concentration. Under non-reducing conditions a major band, migrating slightly faster than 200,000 Daltons marker, was detected. Several fainter bands were also detected. Two of these bands migrated slower than the major band and approximately three other bands migrated faster. Under reducing conditions, two bands, characteristic of the heavy and light chains of immunoglobulin G, were detected.

Using the anti-human IgG reagent under both non-reducing and reducing conditions, the 0.51 µg and the 1.09 µg IgG samples were clearly detected on the nitrocellulose blot. The intensity of the bands increased with increasing concentration. Under non-reducing conditions a major band, corresponding to a species with an apparent molecular weight marker slightly lower than 200,000 Daltons, was detected. The fainter bands observed in the blot, detected with anti-mouse IgG, were also detected. The intensity of the immunostaining was greater for all bands when detected with anti-human IgG. Several additional bands, not observed in the other blot, were detected. It is likely that these bands correspond to IgG fragments lacking epitopes which are recognized by the anti-mouse IgG. Under reducing conditions a band characteristic of the heavy chain of an immunoglobulin G was detected. Because the antibody was specific for the Fc portion of human IgG, the light chain was not detected. Several minor bands, not seen in the blot developed with anti-mouse IgG, were observed when detection was performed with the anti-human IgG. This difference between the two blots may be the result of the presence of IgG fragments which lack epitopes for anti-mouse IgG binding.

3. Isoelectric Focusing

LDP-02/3A9/Lot#1 was subjected to Isoelectric Focusing (IEF) and stained with Colloidal Coomassie blue. The results obtained for LDP-02/3A9/Lot#1 were compared to IEF standards which were focused on the same gel.

80 µl of LDP-02/3A9/Lot#1 at a nominal concentration of 0.82 mg/ml was added to a microconcentrator. The citrate buffer that the antibody was in, was exchanged three times with 160 µl of Tris buffer (0.5 mM, pH 8.8). The final volume of the sample was 135 µl. The final concentration was calculated to be 0.486 mg/ml. This solution was diluted two-fold with 2×IEF sample buffer to obtain a concentration of 0.243 mg/ml. A 13 µl aliquot to the 0.243 mg/ml solution, yielding 3.16 µg of protein, was loaded onto the designated sample of the IEF gel. Control articles included IEF Standards pI 3.6-9.3 (Sigma, Cat #I-3018).

A standard plot was generated by graphing the average of relative distance migration of eight IEF Standards versus the known PI for each of these standard proteins. The linear regression fit of these data yielded a negative slope of 0.03459 and an intercept of 8.91857. The $R^2$ of the fit equaled 0.99206.

Table 6 contains the average distances migrated by the six IEF standards and by LDP-02/3A9/Lot#1. The calculated µIs for LDP-02/3A9/Lot#1 are also shown in this table.

Using the linear regression parameters from the standard plot, the approximate pIs of the five bands for LDP-02/3A9/Lot#1 were calculated to be 7.88, 7.95, 8.09, 8.26, and 8.43, with the predominant peak represented by a pI of 8.09 (Table 6). The pI of this major peak compares favorably with a predicted pI of 7.91 based upon the primary amino acid sequence.

TABLE 6

| Standard | Distance Migrated* | pI[1] |
|---|---|---|
| Lectin | 3.3 mm | 8.8 |
| Lectin | 9.5 mm | 8.6 |
| Lectin | 17.88 mm | 8.2 |
| Myoglobin | 59.3 mm | 6.8 |
| Carbonic Anhydrase I | 74.0 mm | 6.6 |
| Carbonic Anhydrase II | 92.5 mm | 5.9 |
| β-Lactoglobulin A | 105.8 mm | 5.1 |
| Trypsin Inhibitor | 122.0 mm | 4.6 |

| Sample | Distance Migrated | pI[1] |
|---|---|---|
| LDP-02/3A9/Lot #1 (Band 1) | 14.0 mm | 8.43 |
| LDP-02/3A9/Lot #1 (Band 2) | 19.0 mm | 8.26 |
| LDP-02/3A9/Lot #1 (Band 3) | 24.0 mm | 8.09 |
| LDP-02/3A9/Lot #1 (Band 4) | 28.0 mm | 7.95 |
| LDP-02/3A9/Lot #1 (Band 5) | 30.0 mm | 7.88 |

*Average
[1]Based on standard curve (pI vs. Migration distance) where: Sample pI = Intercept − Slope (Sample migration distance).

4. Amino Acid Composition Analysis

Amino acid composition analysis was performed to determine the protein content and amino acid composition of LDP-02/3A9/Lot#1 and confirm identity.

Triplicate 45 µl aliquots were first removed for hydrolysis. Hydrolysis was performed at 165° C. for 60 minutes using 6N HCl vapors. As a control, the hydrolysis vessel contained a standard protein which was hydrolyzed simultaneously with the LDP-02/3A9/Lot#1. Amino acid standards were also chromatographed before and after LDP-02/3A9/Lot#1 analysis. Control articles included Bovine Serum Albumin (Tektagen Solution Control:310:197A) as the standard protein and Amino Acid Hydrolysate Mixture (Tektagen Solution Control:310:199A) as the amino acid standard.

The test method employed analysis of resuspended protein hydrolysate or free amino acid solution by ion exchange HPLC with post-column ninhydrin reaction and absorbance monitoring at two wavelengths. Absorbance at both wavelengths was quantified by comparison to a calibration table obtained by analyzing amino acid standards in triplicate.

Amino acid composition is presented in Table 7. The protein concentration of LDP-02/3A9/Lot#1 was determined to be 0.709 mg/mL. Upon correction for lack of quantitation of W and C, the protein concentration was revised to 0.740 mg/mL. The data and pertinent calculations are summarized in Table 8.

For LDP-02/3A9/Lot#1, a single hydrolysis time point (60 min) was performed at 165° C. using 6N HCl vapors. Correction factors, which have been derived from the standard protein (BSA), were applied to the determinations of protein content (Table 8).

Under conditions of this method, the mole percent values obtained for proline (Table 7) may be slightly elevated, due to the presence of a coeluting cysteine peak. Consequently, the accuracy of proline quantitation is sample dependent, based upon the amount of cysteine present in the sample hydrolysates. For this analysis, the proline content has been corrected using a BSA derived correction factor (Table 8). The accuracy of this correction is sample dependent, based on the relative amounts of cysteine in the BSA (6.0%) and in the sample.

The predicted amino acid composition of LDP-02 as relative percent (frequency or mole percent) based upon the nucleotide sequence of the heavy and light chains (Predicted %), and the actual results of the amino acid analysis (Actual %) are presented in Table 9. Comparison of predicted versus actual values shows good correlation except for proline, which as previously described, is likely artifactually high due to a coeluting cysteine peak.

TABLE 7

| | Sample: | | |
|---|---|---|---|
| AA | LDP-02/3A9/LOT #1 Without correction % mole | LDP-02/3A9/LOT #1 With correction factors derived from BSA % mole | LDP-02/3A9/LOT #1 With correction for W/C[1] and BSA derived factors % mole |
| N/D | 9.1 | 9.0 | 8.6 |
| T | 6.5 | 7.5 | 7.2 |
| S | 9.2 | 13.3 | 12.7 |
| Q/E | 11.4 | 11.3 | 10.8 |
| P | 8.2 | 9.8 | 9.4 |
| G | 7.8 | 7.4 | 7.1 |
| A | 5.9 | 5.8 | 5.6 |
| V | 10.2 | 9.5 | 9.1 |
| M | 0.3 | 0.7 | 0.7 |
| I | 2.5 | 2.6 | 2.5 |
| L | 8.2 | 7.9 | 7.6 |
| Y | 5.2 | 5.0 | 4.8 |
| F | 3.4 | 3.4 | 3.3 |
| H | 2.2 | 2.2 | 2.1 |
| K | 7.0 | 6.9 | 6.6 |
| R | 2.9 | 2.9 | 2.8 |
| TOTAL | 100 | | |

[1]Correlation factor is 0.958, which is based on the W and C content of 1.8% and 2.4%, respectively.

TABLE 8

Protein Content Determination

| AA | Mean nmols | [2]Correction Factor | Corrected nmoles | Residue MW | Quantity found (ng) |
|---|---|---|---|---|---|
| N/D | 5.954 | 0.991 | 5.900 | 115.1 | 679 |
| T | 4.243 | 1.156 | 4.905 | 101.1 | 496 |
| S | 6.054 | 1.448 | 8.766 | 87.1 | 764 |
| Q/E | 7.436 | 0.991 | 7.369 | 128.1 | 944 |
| P | 5.365 | 0.830 | 4.453 | 97.1 | 432 |
| G | 5.080 | 0.951 | 4.831 | 57.1 | 276 |
| A | 3.884 | 0.983 | 3.818 | 71.1 | 271 |
| V | 6.681 | 0.930 | 6.213 | 99.1 | 616 |

TABLE 8-continued

Protein Content Determination

| M | 0.221 | 2.433 | 0.538 | 131.2 | 71 |
| I | 1.606 | 1.036 | 1.664 | 113.2 | 188 |
| L | 5.379 | 0.961 | 5.169 | 113.2 | 585 |
| Y | 3.374 | 0.954 | 3.219 | 163.2 | 525 |
| F | 2.229 | 0.992 | 2.211 | 147.2 | 325 |
| H | 1.442 | 0.981 | 1.415 | 137.2 | 194 |
| K | 4.616 | 0.984 | 5.542 | 125.2 | 582 |
| R | 1.922 | 1.005 | 1.392 | 156.2 | 302 |

| | |
|---|---|
| Total Quantity Injected on column (ng): | 7250 |
| Reconstitution Volume (μl): | 220 |
| [3]Total Quantity Hydrolyzed (ng): | 31900 |
| Total Quantity Hydrolyzed (μg): | 31.9 |
| Original Sample Volume (μl): | 45 |
| Diluted Sample Volume (μl): | 45 |
| Aliquot Value for Hydrolysis (μl): | 45 |
| Protein concentration (mg/ml): | 0.709 |
| Protein Concentration (mg/ml) after correction for W/C: | 0.740 |

[1]Protein content is not corrected for cysteine and tryptophan.
[2]A BSA derived correction factor has been applied to each amino acid detected.
[3]Total ng hydrolyzed = (Total ng injected × reconstitution volume)/Injection volume (50 μl).

TABLE 9

Amino Acid Composition

| Amino Acid Symbol | Amino Acid | Number | Predicted % | Actual % |
|---|---|---|---|---|
| A | Ala | 68 | 5.06 | 5.6 |
| C | Cys | 32 | 2.38 | — |
| D | Asp | 56 | 4.17 | — |
| E | Glu | 68 | 5.06 | — |
| F | Phe | 40 | 2.98 | 3.3 |
| G | Gly | 90 | 6.70 | 7.1 |
| H | His | 28 | 2.08 | 2.1 |
| I | Ile | 30 | 2.23 | 2.5 |
| K | Lys | 96 | 7.14 | 6.6 |
| L | Leu | 98 | 7.29 | 7.6 |
| M | Met | 10 | 0.74 | 0.7 |
| N | Asn | 50 | 3.72 | — |
| P | Pro | 94 | 6.99 | 9.4 |
| Q | Gln | 64 | 4.76 | — |
| R | Arg | 36 | 2.68 | 2.8 |
| S | Ser | 170 | 12.65 | 12.7 |
| T | Thr | 100 | 7.44 | 7.2 |
| V | Val | 126 | 9.38 | 9.1 |
| W | Trp | 24 | 6.98 | — |
| Y | Tyr | 64 | 4.76 | 4.8 |
| N/D | Asn/Asp | 106 | 7.89 | 8.6 |
| Q/E | Gln/Glu | 132 | 9.82 | 10.8 |

5. MALDI-TOF MS Analysis

LDP-02/3A9/Lot#1 was analyzed by MALDI-TOF MS to determine the molecular weight. A main peak with a mass centered at 149,808 Da was detected. The peak centered at 74,927 Da represented the +2 ion of the species found in the main peak. It should be noted that the mass of +2 ion is not exactly half of the M+H ion; this slight disparity is likely caused by experimental inaccuracy, which is within +/−0.2% of the measured value.

Based on the primary predicted sequence of the antibody, the expected molecular mass should be 147,154 Da. The mass difference of 2,654 Da between the observed and the predicted IgG molecular masses, most probably, can be attributed to glycosylation of the molecule. This observed difference would represent a glycosylation level of approximately 1.8%.

B. Affinity

First, titration of LDP-02/3A9/Lot#1 and murine ACT-1 (Lot#2) was performed using flow cytometry on human derived HUT-78 cells. Briefly, $1.0 \times 10^6$ HUT-78 cells were suspended in a volume of 100 μl of either biotinylated murine ACT-1 (Lot#2), biotinylated murine IgG1 (Lot#1 made at LeukoSite, Inc.), biotinylated LDP-02/3A9/Lot#1, or biotinylated human IgG (Jackson ImmunoResearch, Avondale, Pa.; Lot 25794) for 20 minutes at 4° C., after which the antibodies were removed. Unless otherwise indicated, all reagents were diluted in 0.15 M PBS/1.0% FCS/0.1% sodium azide. The varying concentrations for both antibodies included 30 μg/ml (murine ACT-1 only), 15 μg/ml, 7.5 μg/ml, and subsequent 1:10 dilutions of each. After removal of the primary antibodies, the cells were then suspended in 100 μl streptavidin phycoerthrin (Dako Corp., Carpinteria, Calif.) diluted 1:200. After washing in 200 μl PBS, cells were resuspended in 0.5 ml of PBS/1% formalin and refrigerated until analyzed. Samples were analyzed on a FACScan (Becton Dickinson Corp., San Jose, Calif.) using a 488 nm laser to excite phycoerythrin. For each sample, a minimum of 10,000 cells was analyzed and half-maximal mean channel fluorescence (MCF) was calculated. All samples were performed in duplicate.

Figure 15:
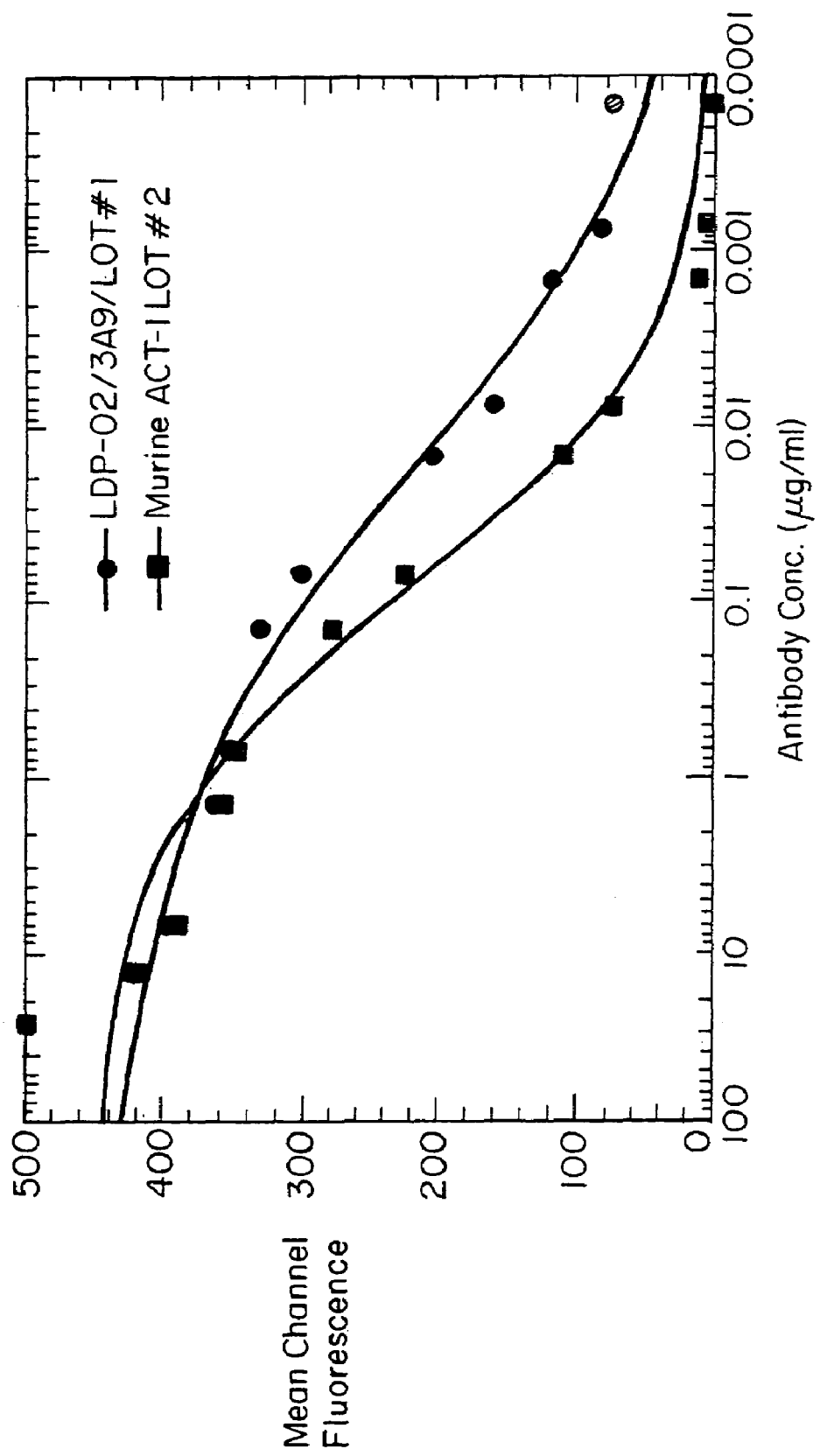
FIG. 15 is a graph illustrating the results of a titration of biotinylated murine Act-1 and humanized Act-1 (LDP-02/3A9/LOT#1, Example 4) performed by flow cytometry on Hut-78 cells.

These titration studies indicated that at concentrations of approximately 1.0 μg/ml, maximal fluorescence was approached using both murine ACT-1 and LDP-02/3A9/Lot#1 (FIG. 15). Half-maximal mean channel fluorescence was achieved at lower concentrations of LDP-02 than for murine ACT-1 (0.1 μg/ml for biotinylated murine ACT-1 Lot#2, and 0.02 μg/ml for LDP-02/3A9/Lot#, respectively).

Relative assessments of affinity (and specificity) were performed using flow cytometry and cross-competitive binding of LDP-02 and the murine Act-1 antibody, and vice versa on human-derived HuT-78 cells. Briefly, $1.0 \times 10^6$ HuT-78 cells were suspended in either 100 μl of biotinylated murine Act-1 (Lot#2) at 0.1 μg/ml with varying concentrations of unconjugated 1°HUM ACT-1 or unconjugated murine Act-1 for 20 minutes at 4° C., after which the antibodies were removed. In a separate experiment, 100 μl of biotinylated LDP-02/3A9/Lot#1 at 0.02 μg/ml was used with varying concentrations of unconjugated murine ACT-1 (Lot#2) and unconjugated LDP-02/3A9/Lot#1. The concentration of biotinylated antibodies held constant were the concentrations resulting in half-maximal mean channel fluorescence (MCF) on HUT-78 cells stained under identical conditions, as demonstrated above. Unless otherwise indicated, all reagents were diluted in 0.15 M PBS/1.0% FCS/0.1% sodium azide. The varying concentrations for both antibodies ranged in half-log increments from $2.0 \times 10^{-6}$ M to $5.0 \times 10^{-11}$ M. After removal of the primary antibodies, the cells were then suspended in 100 μl streptavidin phycoerythrin (Dako Corp., Carpinteria, Calif.) diluted 1:200. After washing in 200 μl PBS, cells were resuspended in 0.5 ml of PBS/1% formalin and refrigerated until analyzed. Samples were analyzed on a FACScan (Becton Dickinson Corp., San Jose, Calif.) using a 488 nm laser to excite phycoerythrin. For each sample, a minimum of 10,000 cells was analyzed and MCF calculated. All samples were performed in duplicate. The $IC_{50}$ was determined as the concentration of unconjugated antibody producing a 50% reduction in the MCF from the biotinylated homologue antibody.

Figure 16:
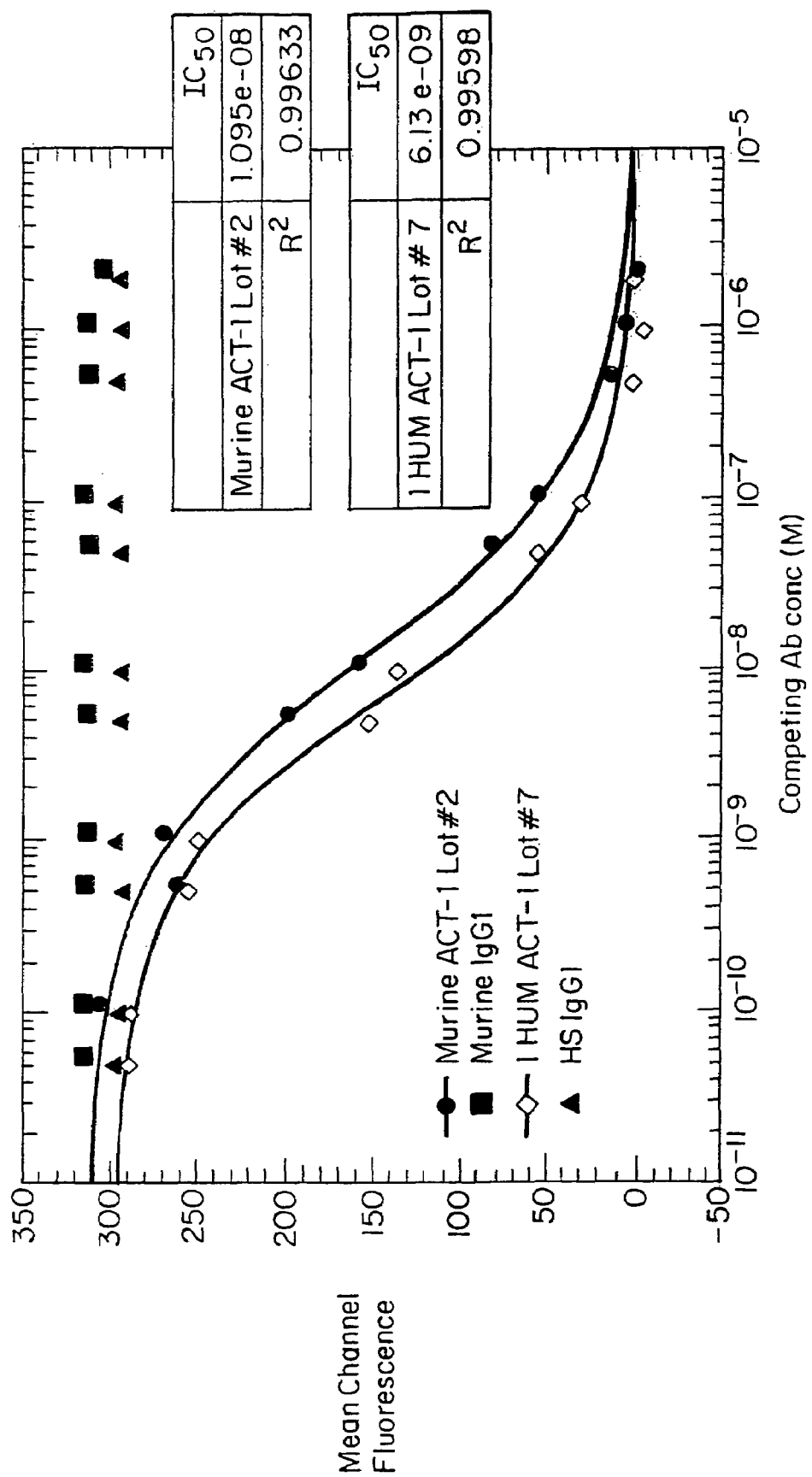
FIG. 16 is a graph illustrating the competitive inhibition of binding of biotinylated murine Act-1 by murine Act-1 or a humanized Act-1 immunoglobulin (LDP-02/3A9/LOT#1, Example 4), compared with control murine IgG1 or human IgG1.

Estimates of affinity were performed in five independent cross-competitive experiments between LDP-02 (1° HUM ACT-1) and murine ACT-1. When biotinylated murine Act-1 was used as the antibody held constant in the assay, mean $IC_{50}$ values (±1 SEM) for LDP-02 (5.43±0.86 nM) were statistically lower than that for murine ACT-1 (7.94±1.17 nM;

p=0.02, two-tail t-test: paired two sample for means), while irrelevant human IgG1 or murine IgG1 had no competitive effect (all experiments summarized in Table 10; one experiment shown in FIG. 16). Similarly, when biotinylated LDP-02/3A9/Lot#1 was the antibody held constant in the assay, a greater concentration of unconjugated murine Act-1 than of LDP-02/3A9/Lot#1 was required to compete LDP-02 off HuT-78 cell membranes ($IC_{50}$=6.3 nM vs. 4.3 nM, respectively). In each experiment, LDP-02 had a lower $IC_{50}$ than did murine Act-1. These results demonstrate that LDP-02 was specific for the epitope recognized by murine Act-1, and that its binding affinity was better than that of the murine antibody.

TABLE 10

Murine ACT-1 and Humanized ACT-1 (LDP-02) Affinity Assessment

| Experiment # | Antibody | Lot # | $IC_{50}$ (nM) |
|---|---|---|---|
| 1 | ACT-1 (murine) | 2 | 7.57 |
| 2 | | 2 | 10.95 |
| 3 | | 2 | 6.02 |
| 4 | | 2 | 4.91 |
| 5 | | 2 | 10.24 |
| | | MEAN ± SEM | 7.94 ± 1.17 |
| 1 | LDP-02 (humanized) | 7 | 4.34 |
| 2 | | 7 | 6.13 |
| 3 | | 8/9 | 4.71 |
| 4 | | 8/9 | 3.53 |
| 5 | | 8/9 | 8.44 |
| | | MEAN ± SEM | 5.43 ± 0.86 | p = 0.02
Two-tail t-Test: Paired Two Sample for Means

C. Species Cross-reactivity

Flow cytometry was used to evaluate species cross-reactivity. 100 μl of EDTA-anticoagulated blood drawn from either a human, dog, cat, guinea pig, or rat was added to FACS tubes. Plasma was removed and blood pellets were then resuspended in 100 μl of either biotinylated LDP-02/3A9/LOT#1, irrelevant biotinylated human IgG (Jackson ImmunoResearch, Avondale, Pa.), biotinylated murine Act-1 Lot#2, or irrelevant biotinylated Murine IgG1 (Dako Corp., Carpinteria, Calif.) at a concentration of 15 μg/ml. Unless otherwise indicated, all reagents were diluted in 0.15 M PBS/1.0% FCS/0.1% sodium azide. Samples were incubated with antibodies for 20 minutes at 4° C. after which the antibodies were removed by washing. Cells were then incubated with 100 μl of strepavidin phycoerythrin diluted 1:200 (Southern Biotechnology Associates, Inc., Birmingham, Ala.) for 20 minutes at 4° C. Red blood cells were then lysed using a commercial lysing reagent (FACS Lysing Solution, Becton Dickinson, San Jose, Calif.) according to manufacturer's protocol. After washing in PBS, cells were resuspended in 0.5 ml of PBS/1% formalin and refrigerated until analyzed. Samples were analyzed on a FACScan (Becton Dickinson Corp., San Jose, Calif.) using a 488 nm laser to excite phycoerythrin. Lymphocyte acquisition gate was set on forward and 90 degree light scatter parameters. For each sample, 10,000 cells were analyzed.

Biotinylated LDP-02/3A9/Lot#1 recognized a subpopulation of human lymphocytes with a heterogenous staining pattern, similar to that produced with murine Act-1, and distinct from the pattern produced by staining with human or murine isotype-matched controls. In addition, when examined on lymphocytes from dog or cat, both LDP-02/3A9/Lot#1 and murine Act-1 produced a similar heterogeneous staining pattern as that derived using human lymphocytes. LDP-02/3A9/Lot#1 or murine ACT-1 did not recognize lymphocytes from rat or guinea pig under these conditions.

D. C1q Binding

Flow cytometry was used to assess the potential of LPD-02 to bind human complement component C1q, using a technique previously described (Sims, M. J. et al., *J. Immunol.* 151: 2296-2308 (1993)). Human peripheral blood mononuclear cells (PBMCs) were isolated by standard Ficoll density separation. 375,000 cells were first blocked with 10% normal rabbit serum/PBS for 10 minutes at 4° C. After removal by washing, cells were incubated with 100 μl of either (a) CAMPATH-1H (Therapeutic Antibody Center, Cambridge, U.K.), (b) human IgG1 (Sigma Chemical Co., St. Louis, Mo.), (c) LDP-01 (a derivative of the anti-CD18 antibody described in WO 93/02191 (published Feb. 4, 1993) and Sims, M. J., et al., *J. Immunol.* 151(4): 2296-2308 (1993), which contains two amino acid substitutions in the IgG1 heavy chain constant region ($Leu^{234} \rightarrow Ala^{234}$ and $Gly^{237} \rightarrow Ala^{237}$), also referred to as "FcRmut CD18", Therapeutic Antibody Center, Cambridge, U.K.), or (d) LDP-02 (1° C. hum ACT-1 Lot#8/9) at 10 μg/ml for 20 minutes at 4° C. CAMPATH-1H served as a positive control antibody, while LDP-01 and human IgG1 were used as negative control antibodies. All reagents were diluted in 2% BSA/PBS. As an additional negative control, 2% BSA/PBS was also added alone. Antibody was then removed by washing, and cells were resuspended in 50 μl human complement component C1q (Sigma Chemical Co., St. Louis, Mo.) at 10 μg/ml for 30 minutes at 4° C. Cells were then washed and resuspended in 100 μl FITC-conjugated rabbit anti-human C1q (Dako Corp., Carpinteria, Calif.) antibody at 20 μg/ml for 20 minutes at 4° C. After washing in 200 μl PBS, cells were resuspended in 0.5 ml of PBS/1% formalin and refrigerated until analyzed. Samples were analyzed on a FACScan (Becton Dickinson Corp., San Jose, Calif.) using a 488 nm laser to excite FITC. For each sample, a minimum of 10,000 cells were analyzed and mean channel fluorescence (MCF) calculated.

Human PBMCs incubated with CAMPATH-1H bound human C1q, resulting in a significant shift in MCF, while the staining patterns elicited by incubation of PBMCs with LDP-01, BSA, or human IgG1 were all similar and characterized by relatively low background staining. The pattern of staining produced by PMBC preincubation with LDP-02 was identical to that produced in these negative control samples, demonstrating that LDP-02 does not bind C1q under these conditions.

E. Complement-mediated Lysis

The ability of LDP-02/3A9/Lot#1 to participate in complement mediated cell lysis was examined using a protocol previously described in Bindon, C. I., et al. (*Transplantation*, 40: 538-544 (1985)). Heparinized human blood was drawn aseptically, and plasma was collected and immediately placed on ice. Peripheral blood mononuclear cells (PBMCs) were isolated by centrifugation for 15 minutes over a layer of Ficoll-Hypaque, density 1.077 g/ml, and were washed twice in complete medium consisting of RPMI 1640/10% FCS/100 U/ml penicillin/100 μg/ml streptomycin/2.0 mM L-glutamine. 25 million cells were then incubated at 37° C. for 1 hr in 150 μCi sodium $^{51}$chromate in sterile saline (E.I. du Pont de Nemours & Co. Inc., Wilmington, Del.). Cells were washed twice in medium and resuspended at $10^6$/ml. 50 μl of the suspension ($5.0 \times 10^4$ cells) were then added to wells of a U-bottom microtiter plate containing 100 μl of either (a) CAMPATH-1H (Therapeutic Center, Cambridge, U.K.), (b) CAMPATH-1 G (Therapeutic Center, Cambridge, U.K.), (c) human IgG1 (Sigma Chemical Co., St. Louis, Mo.), (d) LDP-02/3A9/

Lot#1, or (e) LDP-01 (FcRmut CD18, Therapeutic Antibody Center, Cambridge, U.K. (see above)) at concentrations of 50, 25, 5, 2.5, and 0.5 µg/ml in medium. CAMPATH-1 antibodies were used as positive control antibodies in the assay, while human IgG1 and LDP-01 were used as negative controls. Additional wells contained cells suspended in 100 µl of 0.1% Triton-X-100 (Fisher Scientific, Fair Lawn, N.J.) in complete medium. Cells incubated with Triton-X-100 were used to measure total release, while control wells with no antibody were used to measure spontaneous release. After incubation for 15 minutes at room temperature, 50 µl of autologous plasma as a complement source was added to each well to a final concentration of 20%. The cells were incubated for 45 minutes at 37° C., then centrifuged at 100 g for 2 minutes, and 100 µl of the supernatants were collected. Released $^{51}$Cr was measured on a Cobra II gamma counter (Packard Instruments, Downers Grove, Ill.). All samples were performed in duplicate. The percentage of specific $^{51}$Cr release was calculated using the formula:

$$\text{specific release} = \frac{(\text{test} - \text{spontaneous}) \times 100\%}{\text{total} - \text{spontaneous}}$$

Figure 17:
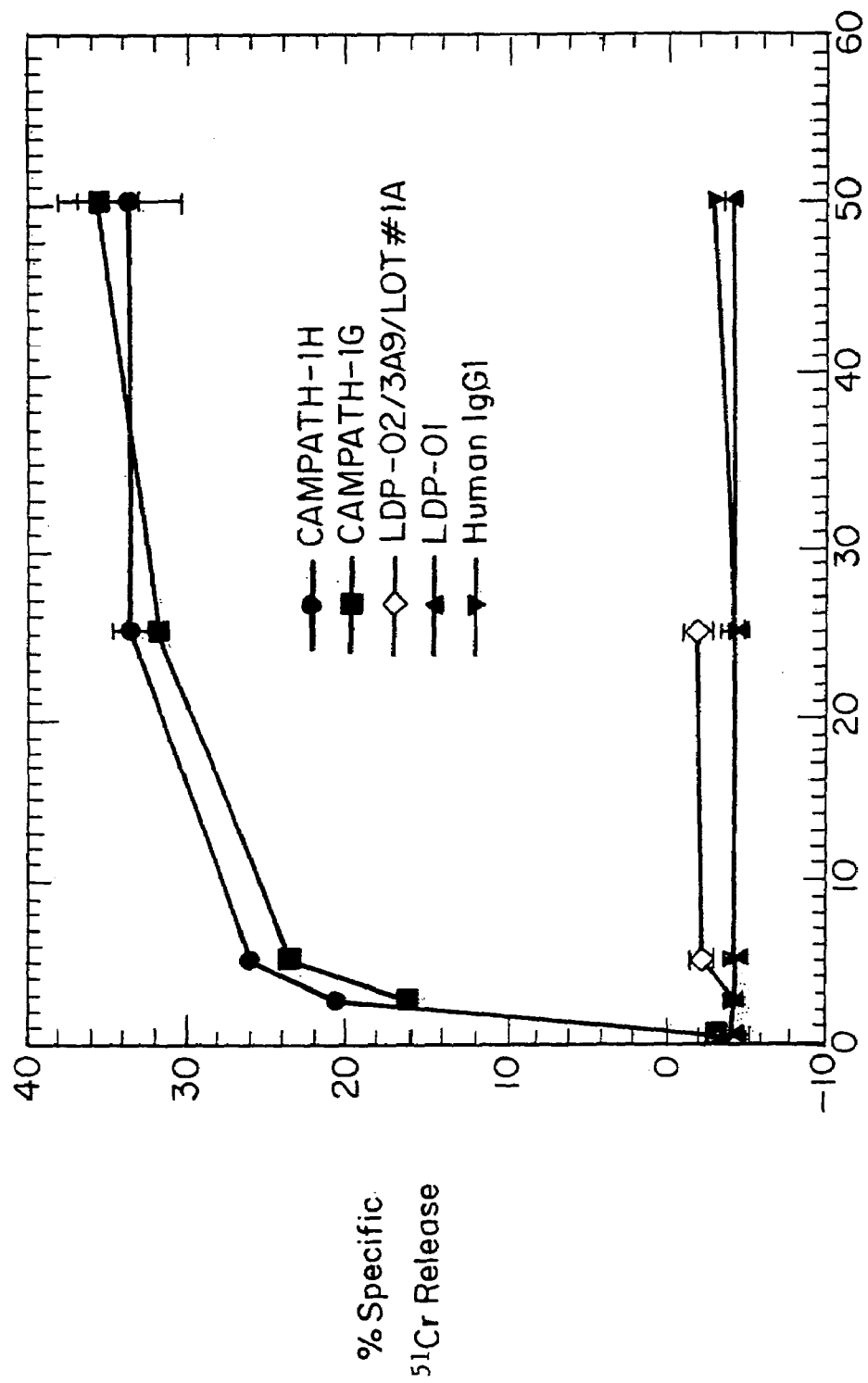
FIG. 17 is a graph illustrating the results of a $^{51}$chromium release assay for complement mediated cell lysis of human peripheral blood mononuclear cells in the presence of (a) CAMPATH-1H, (b) CAMPATH-1G, (c) human IgG1, (d) LDP-02/3A9/Lot#1 (Example 4), or (e) LDP-01 (humanized anti-CD18, Fc-mutated) at concentrations of 50, 25, 5, 2.5, and 0.5 µg/ml.

As previously reported by Bindon et al. (*Transplantation*, 40: 538-544 (1985)), both CAMPATH-1H and CAMPATH-1G induced up to 35% complement-mediated lysis of human PBMCs in a dose-dependent manner. In addition, as expected, human IgG1 and LDP-01 (Fc-mut CD18) controls did not induce any detectable cell lysis. LDP-02 did not mediate cell lysis at any of the concentrations examined, up to and including 25 µg/ml (FIG. 17).

F. Antibody Dependent Cell-mediated Cytotoxicity (ADCC)

Human CD3+ blasts were used as target cells to assess the ability of LDP-02 to participate in antibody dependent cell-mediated cytotoxicity (ADCC). CD3+ blasts were generated in 24-well plates coated with the anti-CD3 antibody RT66 at a concentration of 5 µg/ml diluted in PBS. Human peripheral blood mononuclear cells (PBMCS) were isolated by centrifugation for 15 minutes over a layer of Ficoll-Hypaque, density 1.077 g/ml, washed and resuspended in complete medium, as described in the previous section. 2 million cells were then added to each well of the 24-well plate and incubated at 37° C., 5% $CO_2$ for 4 days. Cells were then transferred to a culture flask and incubated at 37° C., 5% $CO_2$ in medium with human recombinant IL-2 (Genzyme Corp., Cambridge, Mass.) at a concentration of 10 units/ml. After three days in culture, 10.0×10$^6$ CD3 blasts were then incubated at 37° C. for 45 minutes in 150 µCi sodium $^{51}$chromate in sterile saline (E.I. du Pont de Nemours & Co. Inc., Wilmington, Del.; Lot#95M682). After two washes in complete medium, cells were resuspended to 2×10$^5$ cells/ml, and 50 µl (10,000 cells) of the suspension was added to wells of a U-bottom 96 well microtiter plate. The wells contained 50 µl of either CAMPATH-1H (Therapeutic Antibody Center, Cambridge, U.K.) or LDP-02/3A9/Lot#1 at final concentrations of 50, 5, 2.5, 0.5, 0.25, or 0.05 µg/ml in medium. Cells were incubated with antibodies for 30 minutes at room temperature after which 0.5×10$^6$ freshly isolated PBMC's (ficoll-hypaque gradient, 2 washes in complete medium at 37° C.) from a different donor were added to each well as effector cells (effector:target ratio of 50:1). To additional wells, 100 µl of 5% Triton-X-100 in medium (Fisher Scientific, Fair Lawn, N.J.) was added. Cells incubated with Triton-X-100 were used to measure total release, while controls with no antibody and effector cells were included to measure spontaneous radioactivity release. Cells were centrifuged at 100 g for 2 minutes at room temperature and incubated for 20 hours at 37° C., 5% $CO_2$ after which cells were transferred to a V-bottom 96-well plate and pelleted at room temperature. 100 µl of supernatants were collected, and released radioactivity was measured on a Cobra II gamma counter (Packard Instruments, Downers Grove, Ill.). All samples were performed in duplicate. The percentage of specific $^{51}$Cr release was calculated using the formula:

$$\text{specific release} = \frac{(\text{test} - \text{spontaneous}) \times 100\%}{\text{total} - \text{spontaneous}}$$

As previously demonstrated by Sims, M. J. et al., *J. Immunol.*, 151(4):2296-2308 (1993), CAMPATH-1H participated in ADCC in a dose-dependent manner, eliciting up to approximately 30% specific $^{51}$Cr release at concentrations ≧5.0 µg/ml. No specific release was detected in wells containing LDP-02 at any of the concentrations examined.

G. Inhibition of Adhesion to MAdCAM-1

The ability of LDP-02 to inhibit binding of α4β7 to MAdCAM-1 was assessed using fluorescently labeled α4β7+ RPMI 8866 cells (a human B cell lymphoma) and a MAdCAM-1 chimera comprising the entire extracellular domain of human MAdCAM-1 fused to the Fc region of a human IgG1 (a constant region derived from the same construct used to make the constant region of Fc-mutated LDP-02).

1. Construction of MAdCAM-IgG Chimera

A Human MAdCAM-1 clone designated pcDhuMAd4 (clone 4 cDNA in pCDNA3; Shyjan, A. M. et al., *J. Immunol.*, 156: 2851-2857 (1996); the teachings of which are incorporated herein by reference in their entirety) was used as a template for PCR amplification of extracellular regions of human MAdCAM-1 to be fused with the constant region of human IgG1, as described in International Appplication No. PCT/US96/02153 (designating the U.S.), filed Feb. 12, 1996, which is a continuation-in-part of U.S. Ser. No. 08/523,004, filed Sep. 1, 1995, which is a continuation-in-part of U.S. Ser. No. 08/386,857, filed Feb. 10, 1995, the teachings of which are each incorporated herein by reference in their entirety. To construct the MAdCAM-IgG chimera, primer HUMADIG4/2 (SEQ ID NO:62), which contains the 5' end of human MAdCAM-1 coding sequence (ATG codon, bold), was synthesized:

```
HindIII
5'-GGAAGCTTCCACCATGGATTTCGGACTGGCCC-3'
```

This 5' primer was used in conjunction with a 3' primer designated HUMADIG3 to amplify a region encoding the entire extracellular domain of human MAdCAM-1. The 3' primer HUMADIG3 (SEQ ID NO:63) has the following sequence:

```
SpeI
5'-GGACTAGTGGTTTGGACGAGCCTGTTG-3'
```

The primers were designed with a 5' HindIII site or 3' SpeI sites as indicated. These primers were used to PCR amplify a MAdCAM fragment using a PCR optimizer kit from Invitrogen (San Diego, Calif.). The PCR products were digested with the enzymes HindIII and SpeI to generate ends for cloning, and were purified by gel electrophoresis using the Glassmax DNA isolation system (Gibco, Bethesda, Md.).

A ~1 kb fragment encompassing the CH1, H (hinge), CH2 and CH3 regions was excised by digestion with SpeI and EcoRI from a construct encoding a human immunoglobulin γ1 heavy chain having an Fc-mutated human constant region. The human constant region in this construct was originally obtained by PCR amplification of the CAMPATH-1H heavy chain (Reichmann, L. et al., *Nature*, 322: 323-327 (1988)) as described by Sims, M. J. et al. (*J. Immunol.*, 151: 2296-2308 (1993)) and Waldmann et al. (WO 93/02191, Feb. 4, 1993 (page 23)), the teachings of which are each incorporated herein by reference in their entirety. The mutations in the constant region of this construct (Leu$^{234}$→Ala$^{234}$ and Gly$^{237}$→Ala$^{237}$) were designed to reduce binding to human Fcγ receptors, and were produced by oligonucleotide-directed mutagenesis. Thus, the MAdCAM-Ig fusion produced contains the SpeI-EcoRI constant region fragment described by Sims et al. (*J. Immunol.*, 151: 2296-2308 (1993)) and Waldmann et al. (WO 93/02191), except for the introduction of Leu$^{234}$→Ala$^{234}$ and Gly$^{237}$→Ala$^{237}$ mutations.

The 1 kb SpeI-EcoRI fragment encoding the Fc-mutated IgG1 constant region was isolated by gel electrophoresis using the Glassmax DNA isolation system (Gibco, Bethesda Md.). This constant region fragment and the HindIII-SpeI fragment containing the entire extracellular domain of MAdCAM were ligated in a three-way ligation to vector pEE12 (Stephens, P. L. and M. L. Cockett, *Nucl. Acids Res.*, 17: 7110 (1989) and Bebbington, C. R. and C. C. G. Hentschel, 1987, *The use of vectors based on gene amplification for the expression of cloned genes in mammalian cells*, (Academic Press, N.Y.), which had been digested with HindIII and EcoRI. Transformants of the bacterial strain DH10B were obtained. Colonies were grown and mini-plasmid preps were analyzed by restriction mapping. A construct which encodes a fusion protein comprising the entire extracellular domain of MAdCAM-1 (construct HuMAdIg21) fused to the Fc-mutated IgG1 constant region, was sequenced across the entire MAdCAM-1 portion, confirming proper fusion of segments and the absence of PCR induced mutations. The chimera was produced in NSO cells and purified by standard protein A affinity chromatography.

2. Adhesion Assay

A high binding flat-bottom 96-well plate (Costar) was coated for 1 hr at 37° C. with 50 μl of MAdCAM-1 chimera diluted to 2.5 μg/ml in carbonate buffer, pH 9.5. Wells were then washed once with wash buffer (50 mM Tris HCl, 0.14 M NaCl, 1 mM MnCl$_2$, pH 7.2) using a microplate autowasher (Bio-Tek Instruments, Winooski, Vt.) and blocked for 1.5 hrs at 37° C. with 100 μl of 10% FBS diluted in PBS.

RPMI 8866 cells (a human B cell lymphoma line which expresses α4β7 (and not α4β1) (Erle, D. J., et al., *J. Immunol.*, 153:517 (1994); a gift from D. Erle)) were first washed in 20 ml PBS (4° C.) and resuspended to 4.0×10$^6$ cells/ml in PBS. BCECF (2',7'-bis-(2-carboxyethyl)-5-(and 6)-carboxy fluorescein, acetoxymethyl ester; Molecular Probes, Inc., Eugene, Oreg.) was reconstituted to 50 μg/ml in DMSO and added to the cell suspension to a final dilution of 1:500. After incubating for 30 minutes at 37° C., cells were then washed in assay buffer (HBSS with 2% Fetal Bovine Serum, 25 mM HEPES, penicillin/streptomycin, pH 7.2), and 50,000 cells were added to each well of a V-bottom 96-well plate. Cells were then resuspended in 100 μl of either (a) murine Act-1, (b) murine IgG1 (Sigma Chemical Co., St. Louis, Mo.), (c) LDP-02/3A9/Lot#1, or (d) human IgG1 (Sigma Chemical Co., St. Louis, Mo.) at concentrations from 15.0 to 0.00075 μg/ml in assay buffer for 10 minutes at room temperature. The plate coated with MAdCAM-1 chimera was washed to remove blocking buffer, and these fluorescently labeled RPMI 8866 cells were then transferred to each well. The plate was placed on a platform shaker (New Brunswick Scientific Co., Inc., Edison, N.J.) at 40 RPM for 30 minutes at room temperature wrapped in aluminum foil. Unbound cells were removed by a single wash step and fluorescence subsequently measured (excite at 485 nm, read at 535 nm) with a Fluorescence Concentrator Analyzer (IDEXX Laboratories, Inc., Westbrook, Me.) before and after washing. The percent of bound cells for each well was calculated from Relative fluorescent units (RFU) using the formula:

$$\% \text{ bound cells} = \frac{RFU \text{ before wash}}{RFU \text{ after wash}} \times 100$$

Figure 18A:
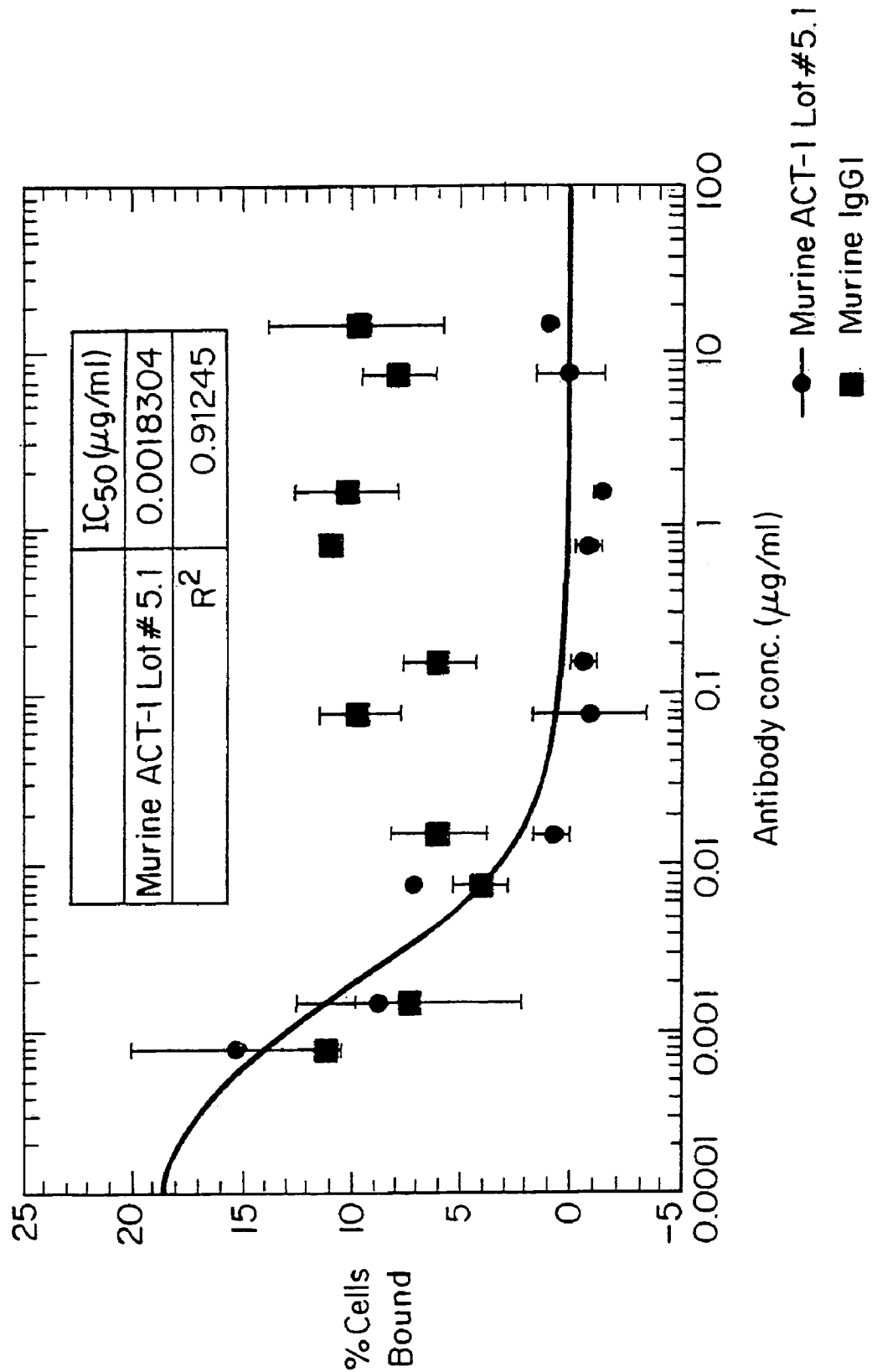
FIGS. 18A-18B are graphs illustrating the results of an adhesion assay monitoring the inhibition of adhesion by murine Act-1 (FIG. 18A), murine IgG1 (FIG. 18A), LDP-02/3A9/Lot#1 (FIG. 18B) or human IgG1 (FIG. 18B) of α4β7-bearing cells (RPMI 8866) and a human MAdCAM-1-Ig chimera (immunoadhesin).
Figure 18B:
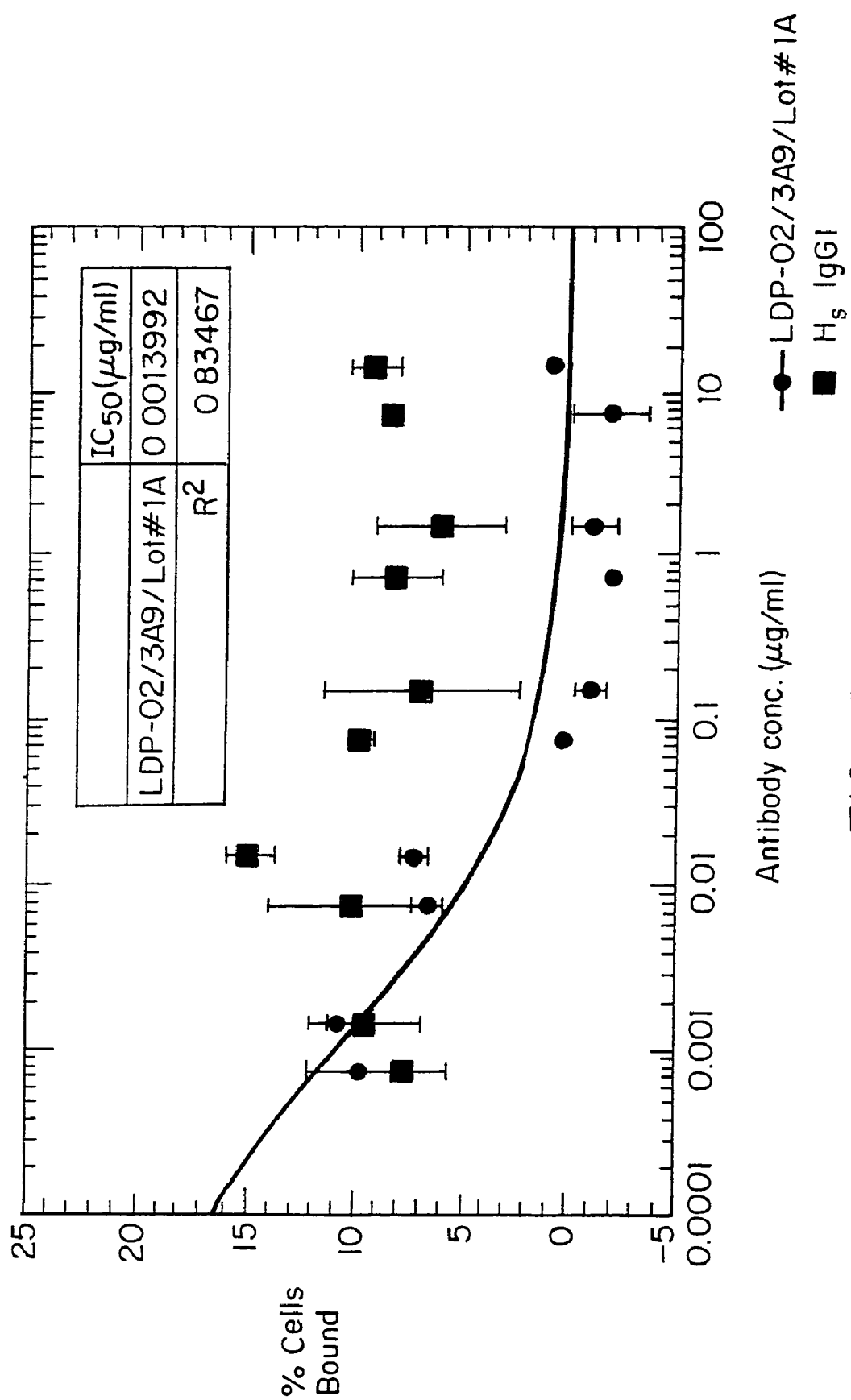

Both LDP-02 and murine Act-1 inhibited adhesion of RPMI 8866 cells to human MAdCAM in a dose dependent manner (FIGS. 18A-18B). The concentrations which inhibited adhesion by 50% (IC$_{50}$) were relatively similar for murine Act-1 (0.0018 μg/ml) and LDP-02 (0.0014 μg/ml). Therefore, LDP-02 functionally inhibited α4β7-mediated adhesion to MAdCAM-1 at least as effectively as murine Act-1.

EXAMPLE 5

Additional Humanized Antibodies

As described above, several variations of the reshaped antibody designed in Example 2 can be made to improve affinity and/or to decrease the antigenicity of the reshaped antibody. Such constructs include, but are not limited to, those having one or more of the following mutations: M4V mutation in the light chain, R38K mutation in the heavy chain, A40R mutation in the heavy chain, and I73T back-mutation in the heavy chain. Mutants can be produced individually (e.g., one mutation in one chain), or in various combinations.

Figure 19:
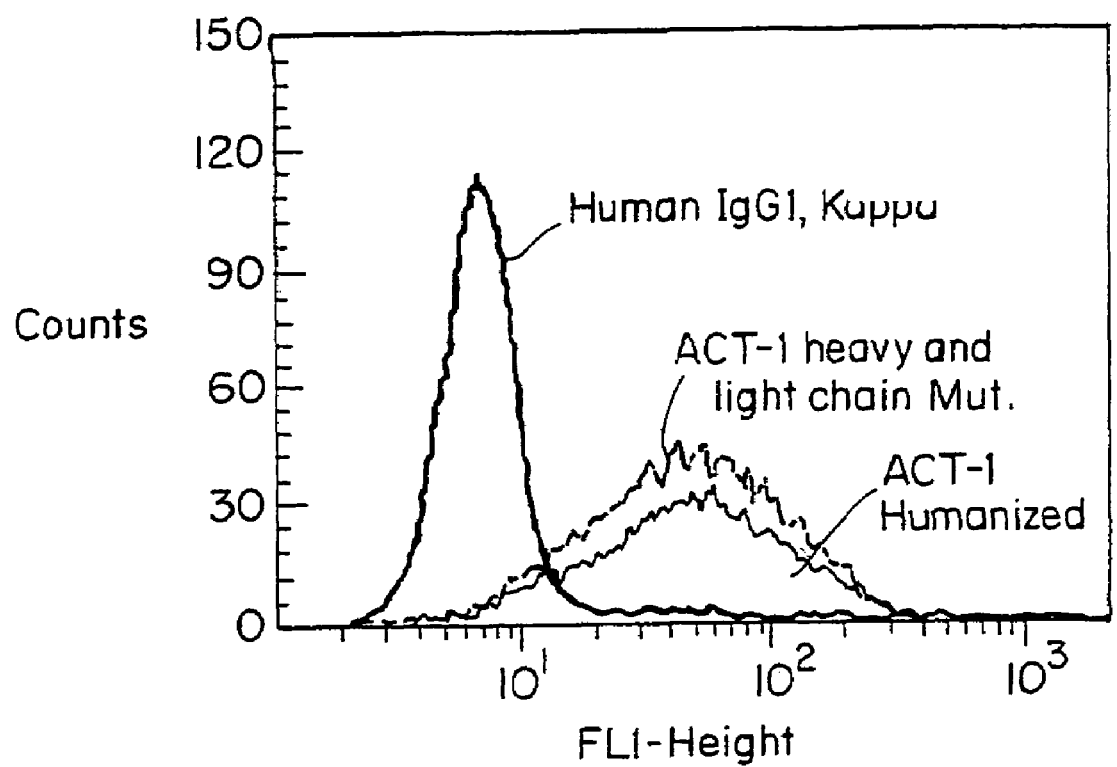
FIG. 19 is a graph comparing the staining of HuT 78 cells using (a) LDP-02 (Fc-mutated), (b) a derivative of LDP-02 (Fc-mutated) having a mutation in the light chain (MV4) plus a double mutation in the heavy chain (R38K, A40R), or (c) an irrelevant, human isotype matched control antibody (IgG1, kappa).

For example, FIG. 19 shows the results of HuT 78 staining using the reshaped antibody (designed in Example 2) or a derivative having an additional mutation in the light chain (MV4) and two additional mutations in the heavy chain (R38K, A40R). These two antibodies show similar staining patterns on HuT 78 cells (FIG. 19). The mutations were made by changing the nucleic acid sequence using a Transformer Site-Directed Mutagenesis Kit (Clontech) according to manufacturer's suggested protocol. Mutations of both heavy chain and light chain variable regions were made with variable fragments cloned into pCR-Script™. The trans oligo Sca I/Stu I (Clontech) was used for the trans oligo. The sequence of the mutagenic oligos (SEQ ID NOS:38-40) were as follows:

```
H/R38K (SEQ ID NO:38):
5'-C TGG CCA ACG

H/I73T (SEQ ID NO:39):
5'-CAC ATT GAC TGT AGA CAC TTC CGC TAG CAC AGC C

L/M4V (SEQ ID NO:40):
5'-CCG GAG GTG ATG TTG TGG TGA CTC
```

All other manipulations, including subcloning into expression vectors pEE6hCMV-B and pEE12, and construction of expression plasmids containing both heavy and light chain genes, were as described for the primary reshaped antibody. Transient transfections and cell staining were also done as described for the primary reshaped antibody.

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. An isolated nucleic acid molecule encoding a humanized immunoglobulin or antigen-binding fragment thereof having binding specificity for α4β7 integrin, wherein said humanized immunoglobulin or antigen-binding fragment thereof comprises a heavy chain and a light chain, said heavy chain comprising the variable region of SEQ ID NO:19, and said light chain comprising the variable region of SEQ ID NO:21.

2. The isolated nucleic acid of claim 1, wherein said isolated nucleic acid molecule comprises a first nucleotide sequence encoding the variable region of SEQ ID NO:19, and a second nucleotide sequence encoding the variable region of SEQ ID NO:21.

3. The isolated nucleic acid of claim 2, wherein said first nucleotide sequence further encodes an IgG constant region or a modified IgG constant region with minimized Fc receptor binding activity, minimized complement fixing activity, or minimized Fc receptor binding activity and minimized complement fixing activity.

4. An expression vector comprising a nucleotide sequence which encodes a humanized immunoglobulin or antigen-binding fragment thereof having binding specificity for α4β7 integrin, wherein said humanized immunoglobulin or antigen-binding fragment thereof comprises a heavy chain and a light chain, said heavy chain comprising the variable region of SEQ ID NO:19, and said light chain comprising the variable region of SEQ ID NO:21.

5. The expression vector of claim 4, wherein said expression vector comprises a first nucleotide sequence that encodes the variable region of SEQ ID NO:19, and a second nucleotide sequence that encodes the variable region of SEQ ID NO:21.

6. The expression vector of claim 5, wherein said first nucleotide sequence further encodes an IgG constant region or a modified IgG constant region with minimized Fc receptor binding activity, minimized complement fixing activity, or minimized Fc receptor binding activity and minimized complement fixing activity.

7. A host cell comprising the expression vector of claim 4.

8. A method of preparing a humanized immunoglobulin or antigen-binding fragment thereof, comprising maintaining a host cell of claim 7 under conditions suitable for expression of a humanized immunoglobulin or antigen-binding fragment thereof, whereby a humanized immunoglobulin or antigen-binding fragment thereof is produced.

9. The method of claim 8, further comprising isolating the humanized immunoglobulin or antigen-binding fragment.

10. An isolated nucleic acid molecule encoding a humanized immunoglobulin heavy chain or antigen-binding portion thereof, wherein said heavy chain or antigen-binding portion thereof comprises the variable region of SEQ ID NO:19.

11. The isolated nucleic acid molecule of claim 10, wherein said heavy chain comprises an IgG constant region or a modified IgG constant region with minimized Fc receptor binding activity, minimized complement fixing activity, or minimized Fc receptor binding activity and minimized complement fixing activity.

12. An expression vector comprising a nucleotide sequence that encodes a humanized immunoglobulin heavy chain or antigen-binding portion thereof, wherein said heavy chain or antigen-binding portion thereof comprises the variable region of SEQ ID NO:19.

13. The expression vector of claim 12, wherein said heavy chain comprises an IgG constant region or a modified IgG constant region with minimized Fc receptor binding activity, minimized complement fixing activity, or minimized Fc receptor binding activity and minimized complement fixing activity.

14. A host cell comprising the expression vector of claim 12.

15. A method of preparing a humanized immunoglobulin heavy chain or antigen-binding portion thereof, comprising maintaining a host cell of claim 14 under conditions suitable for expression of a humanized immunoglobulin heavy chain or antigen-binding portion thereof, whereby a humanized immunoglobulin heavy chain or antigen-binding portion thereof is produced.

16. The method of claim 15, further comprising isolating the humanized immunoglobulin heavy chain or antigen-binding portion thereof.

17. An isolated nucleic acid molecule encoding a humanized immunoglobulin light chain or antigen-binding portion thereof, wherein said light chain or antigen-binding portion thereof comprises the variable region of SEQ ID NO:21.

18. The isolated nucleic acid molecule of claim 17, wherein said humanized immunoglobulin light chain further comprises a constant region.

19. An expression vector encoding a humanized immunoglobulin light chain or antigen-binding portion thereof, wherein said light chain or antigen-binding portion thereof comprises the variable region of SEQ ID NO:21.

20. The expression vector of claim 19, wherein said humanized immunoglobulin light chain further comprises a constant region.

21. A host cell comprising the expression vector of claim 19.

22. A method of preparing a humanized immunoglobulin light chain or antigen-binding portion thereof, comprising maintaining a host cell of claim 21 under conditions suitable for expression of a humanized iinmunoglobulin light chain or antigen-binding portion thereof, whereby a humanized immunoglobulin light chain or antigen-binding portion thereof is produced.

23. The method of claim 22, further comprising isolating the humanized immunoglobulin light chain or antigen-binding portion thereof.

* * * * *

SEQUENCE LISTING

<160> NUMBER OF SEQ ID NOS: 67

<210> SEQ ID NO 1
<211> LENGTH: 494
<212> TYPE: DNA
<213> ORGANISM: Artificial Sequence
<220> FEATURE:
<223> OTHER INFORMATION: Mouse consensus sequence
<220> FEATURE:
<221> NAME/KEY: unsure
<222> LOCATION: (450)...(450)
<223> OTHER INFORMATION: n=A,T,G or C
<220> FEATURE:
<221> NAME/KEY: unsure
<222> LOCATION: (466)...(466)
<223> OTHER INFORMATION: n=A,T,G or C
<220> FEATURE:
<221> NAME/KEY: unsure
<222> LOCATION: (467)...(467)
<223> OTHER INFORMATION: n=A,T,G or C
<220> FEATURE:
<221> NAME/KEY: unsure
<222> LOCATION: (482)...(482)
<223> OTHER INFORMATION: n=A,T,G or C
<220> FEATURE:
<221> NAME/KEY: unsure
<222> LOCATION: (483)...(483)
<223> OTHER INFORMATION: n=A,T,G or C

<400> SEQUENCE: 1

```
ttackrgwmk wcatgrratg sasctrkrtc atyytcttct tggtatcaac agctacaagt      60
gtccactccc aggtccaact gcagcagcct ggggctgagc ttgtgaagcc tgggacttca     120
gtgaagctgt cctgcaaggg ttatggctac accttcacca gctactggat gcactgggtg     180
aagcagaggc ctggacaagg ccttgagtgg atcggagaga ttgatccttc tgagagtaat     240
actaactaca atcaaaaatt caagggcaag gccacattga ctgtagacat ttcctccagc     300
acagcctaca tgcagctcag cagcctgaca tctgaggact ctgcggtcta ctattgtgca     360
agagggggtt acgacggatg ggactatgct attgactact ggggtcaagg cacctcagtc     420
accgtctcct cagccaaaac gacaccrycn csyktmtmyc yysbdnnccc ykgrwscytg     480
gnngaagctt ggga                                                       494
```

<210> SEQ ID NO 2
<211> LENGTH: 144
<212> TYPE: PRT
<213> ORGANISM: Artificial Sequence
<220> FEATURE:
<223> OTHER INFORMATION: Mouse consensus sequence
<220> FEATURE:
<221> NAME/KEY: UNSURE
<222> LOCATION: (2)...(6)
<223> OTHER INFORMATION: Xaa = Any Amino Acid
<220> FEATURE:
<221> NAME/KEY: UNSURE
<222> LOCATION: (8)...(8)
<223> OTHER INFORMATION: Xaa = Any Amino Acid

<400> SEQUENCE: 2

```
Met Xaa Xaa Xaa Xaa Xaa Ile Xaa Phe Leu Val Ser Thr Ala Thr Ser
 1               5                  10                  15

Val His Ser Gln Val Gln Leu Gln Gln Pro Gly Ala Glu Leu Val Lys
            20                  25                  30

Pro Gly Thr Ser Val Lys Leu Ser Cys Lys Gly Tyr Gly Tyr Thr Phe
        35                  40                  45
```

```
Thr Ser Tyr Trp Met His Trp Val Lys Gln Arg Pro Gly Gln Gly Leu
 50                  55                  60

Glu Trp Ile Gly Glu Ile Asp Pro Ser Glu Ser Asn Thr Asn Tyr Asn
 65                  70                  75                  80

Gln Lys Phe Lys Gly Lys Ala Thr Leu Thr Val Asp Ile Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Ser Val Thr Val Ser Ser Ala Lys Thr Thr
130                 135                 140
```

<210> SEQ ID NO 3
<211> LENGTH: 428
<212> TYPE: DNA
<213> ORGANISM: Unknown
<220> FEATURE:
<223> OTHER INFORMATION: Mouse
<220> FEATURE:
<221> NAME/KEY: CDS
<222> LOCATION: (18)...(428)

<400> SEQUENCE: 3

```
ttacttgacg actcggg atg gga tgg agc tat atc atc ttc ttc ttg gta        50
                   Met Gly Trp Ser Tyr Ile Ile Phe Phe Leu Val
                    1               5                  10 tca aca gct aca agt gtc cac tcc cag gtc caa ctg cag cag cct ggg        98
Ser Thr Ala Thr Ser Val His Ser Gln Val Gln Leu Gln Gln Pro Gly
             15                  20                  25 gct gag ctt gtg aag cct ggg act tca gtg aag ctg tcc tgc aag ggt       146
Ala Glu Leu Val Lys Pro Gly Thr Ser Val Lys Leu Ser Cys Lys Gly
         30                  35                  40 tat ggc tac acc ttc acc agc tac tgg atg cac tgg gtg aag cag agg       194
Tyr Gly Tyr Thr Phe Thr Ser Tyr Trp Met His Trp Val Lys Gln Arg
     45                  50                  55 cct gga caa ggc ctt gag tgg atc gga gag att gat cct tct gag agt       242
Pro Gly Gln Gly Leu Glu Trp Ile Gly Glu Ile Asp Pro Ser Glu Ser
 60                  65                  70                  75 aat act aac tac aat caa aaa ttc aag ggc aag gcc aca ttg act gta       290
Asn Thr Asn Tyr Asn Gln Lys Phe Lys Gly Lys Ala Thr Leu Thr Val
                 80                  85                  90 gac att tcc tcc agc aca gcc tac atg cag ctc agc agc ctg aca tct       338
Asp Ile Ser Ser Ser Thr Ala Tyr Met Gln Leu Ser Ser Leu Thr Ser
             95                 100                 105 gag gac tct gcg gtc tac tat tgt gca aga ggg ggt tac gac gga tgg       386
Glu Asp Ser Ala Val Tyr Tyr Cys Ala Arg Gly Gly Tyr Asp Gly Trp
         110                 115                 120 gac tat gct att gac tac tgg ggt caa ggc aca tca gtc acc                428
Asp Tyr Ala Ile Asp Tyr Trp Gly Gln Gly Thr Ser Val Thr
     125                 130                 135
```

<210> SEQ ID NO 4
<211> LENGTH: 137
<212> TYPE: PRT
<213> ORGANISM: Unknown
<220> FEATURE:
<223> OTHER INFORMATION: Mouse

<400> SEQUENCE: 4

```
Met Gly Trp Ser Tyr Ile Ile Phe Phe Leu Val Ser Thr Ala Thr Ser
 1               5                  10                  15
```

```
Val His Ser Gln Val Gln Leu Gln Gln Pro Gly Ala Glu Leu Val Lys
        20                  25                  30

Pro Gly Thr Ser Val Lys Leu Ser Cys Lys Gly Tyr Gly Tyr Thr Phe
            35                  40                  45

Thr Ser Tyr Trp Met His Trp Val Lys Gln Arg Pro Gly Gln Gly Leu
    50                  55                  60

Glu Trp Ile Gly Glu Ile Asp Pro Ser Glu Ser Asn Thr Asn Tyr Asn
65                  70                  75                  80

Gln Lys Phe Lys Gly Lys Ala Thr Leu Thr Val Asp Ile Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Ser Val Thr
        130                 135

<210> SEQ ID NO 5
<211> LENGTH: 535
<212> TYPE: DNA
<213> ORGANISM: Artificial Sequence
<220> FEATURE:
<223> OTHER INFORMATION: Mouse consensus sequence
<220> FEATURE:
<221> NAME/KEY: CDS
<222> LOCATION: (16)...(435)

<400> SEQUENCE: 5
cgattactag tcgac atg aag ttg cct gtt agg ctg ttg gtg ctt ctg ttg      51
                Met Lys Leu Pro Val Arg Leu Leu Val Leu Leu Leu
                  1               5                  10 ttc tgg att cct gtt tcc gga ggt gat gtt gtg gtg act caa act cca      99
Phe Trp Ile Pro Val Ser Gly Gly Asp Val Val Val Thr Gln Thr Pro
            15                  20                  25 ctc tcc ctg cct gtc agc ttt gga gat caa gtt tct atc tct tgc agg     147
Leu Ser Leu Pro Val Ser Phe Gly Asp Gln Val Ser Ile Ser Cys Arg
        30                  35                  40 tct agt cag agt ctt gca aag agt tat ggg aac acc tat ttg tct tgg     195
Ser Ser Gln Ser Leu Ala Lys Ser Tyr Gly Asn Thr Tyr Leu Ser Trp
45                  50                  55                  60 tac ctg cac aag cct ggc cag tct cca cag ctc ctc atc tat ggg att     243
Tyr Leu His Lys Pro Gly Gln Ser Pro Gln Leu Leu Ile Tyr Gly Ile
                65                  70                  75 tcc aac aga ttt tct ggg gtg cca gac agg ttc agt ggc agt ggt tca     291
Ser Asn Arg Phe Ser Gly Val Pro Asp Arg Phe Ser Gly Ser Gly Ser
            80                  85                  90 ggg aca gat ttc aca ctc aag atc agc aca ata aag cct gag gac ttg     339
Gly Thr Asp Phe Thr Leu Lys Ile Ser Thr Ile Lys Pro Glu Asp Leu
        95                  100                 105 gga atg tat tac tgc tta caa ggt aca cat cag ccg tac acg ttc gga     387
Gly Met Tyr Tyr Cys Leu Gln Gly Thr His Gln Pro Tyr Thr Phe Gly
    110                 115                 120 ggg ggg acc aag ctg gaa ata aaa cgg gct gat gct gca cca act gta     435
Gly Gly Thr Lys Leu Glu Ile Lys Arg Ala Asp Ala Ala Pro Thr Val
125                 130                 135                 140 tccatcttcc caccatccag taagcttggg aatccatatg actagtagat cctctagagt     495
cgacctgcag gcatgcaagc ttccctatag tgagtcgtat                            535
```

<210> SEQ ID NO 6
<211> LENGTH: 140
<212> TYPE: PRT
<213> ORGANISM: Artificial Sequence
<220> FEATURE:
<223> OTHER INFORMATION: Mouse consensus sequence

<400> SEQUENCE: 6

```
Met Lys Leu Pro Val Arg Leu Leu Val Leu Leu Phe Trp Ile Pro
 1               5                   10                  15

Val Ser Gly Gly Asp Val Val Thr Gln Thr Pro Leu Ser Leu Pro
                20                  25                  30

Val Ser Phe Gly Asp Gln Val Ser Ile Ser Cys Arg Ser Gln Ser
                35                  40                  45

Leu Ala Lys Ser Tyr Gly Asn Thr Tyr Leu Ser Trp Tyr Leu His Lys
        50                  55                      60

Pro Gly Gln Ser Pro Gln Leu Leu Ile Tyr Gly Ile Ser Asn Arg Phe
65                  70                      75                  80

Ser Gly Val Pro Asp Arg Phe Ser Gly Ser Gly Ser Gly Thr Asp Phe
                85                  90                      95

Thr Leu Lys Ile Ser Thr Ile Lys Pro Glu Asp Leu Gly Met Tyr Tyr
                100                 105                     110

Cys Leu Gln Gly Thr His Gln Pro Tyr Thr Phe Gly Gly Gly Thr Lys
                115                 120                     125

Leu Glu Ile Lys Arg Ala Asp Ala Ala Pro Thr Val
                130             135                 140
```

<210> SEQ ID NO 7
<211> LENGTH: 112
<212> TYPE: PRT
<213> ORGANISM: Unknown
<220> FEATURE:
<223> OTHER INFORMATION: Mouse

<400> SEQUENCE: 7

```
Asp Val Val Thr Gln Thr Pro Leu Ser Leu Pro Val Ser Phe Gly
 1               5                   10                  15

Asp Gln Val Ser Ile Ser Cys Arg Ser Ser Gln Ser Leu Ala Lys Ser
                20                  25                      30

Tyr Gly Asn Thr Tyr Leu Ser Trp Tyr Leu His Lys Pro Gly Gln Ser
            35                  40                  45

Pro Gln Leu Leu Ile Tyr Gly Ile Ser Asn Arg Phe Ser Gly Val Pro
        50                  55                      60

Asp Arg Phe Ser Gly Ser Gly Ser Gly Thr Asp Phe Thr Leu Lys Ile
65                  70                      75                  80

Ser Thr Ile Lys Pro Glu Asp Leu Gly Met Tyr Tyr Cys Leu Gln Gly
                85                  90                      95

Thr His Gln Pro Tyr Thr Phe Gly Gly Gly Thr Lys Leu Glu Ile Lys
                100                 105                     110
```

<210> SEQ ID NO 8
<211> LENGTH: 112
<212> TYPE: PRT
<213> ORGANISM: Homo sapiens

<400> SEQUENCE: 8

```
Asp Ile Val Met Thr Gln Ser Pro Leu Ser Leu Pro Val Thr Pro Gly
 1               5                   10                  15
```

-continued

```
Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Val Glu Ile Lys
            100                 105                 110
```

<210> SEQ ID NO 9
<211> LENGTH: 121
<212> TYPE: PRT
<213> ORGANISM: Unknown
<220> FEATURE:
<223> OTHER INFORMATION: Mouse

<400> SEQUENCE: 9

```
Gln Val Gln Leu Gln Gln Pro Gly Ala Glu Leu Val Lys Pro Gly Thr
1               5                   10                  15

Ser Val Lys Leu Ser Cys Lys Gly Tyr Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asp Pro Ser Glu Ser Asn Thr Asn Tyr Asn Gln Lys Phe
    50                  55                  60

Lys Gly Lys Ala Thr Leu Thr Val Asp Ile Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Asp Gly Trp Asp Tyr Ala Ile Asp Tyr Trp Gly
            100                 105                 110

Gln Gly Thr Ser Val Thr Val Ser Ser
        115                 120
```

<210> SEQ ID NO 10
<211> LENGTH: 119
<212> TYPE: PRT
<213> ORGANISM: Homo sapiens

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
```

```
                      100                 105                 110
Thr Leu Val Thr Val Ser Ser
        115

<210> SEQ ID NO 11
<211> LENGTH: 396
<212> TYPE: DNA
<213> ORGANISM: Unknown
<220> FEATURE:
<223> OTHER INFORMATION: Mouse
<220> FEATURE:
<221> NAME/KEY: CDS
<222> LOCATION: (1)...(396)

<400> SEQUENCE: 11 atg aag ttg cct gtt agg ctg ttg gtg ctt ctg ttg ttc tgg att cct    48
Met Lys Leu Pro Val Arg Leu Leu Val Leu Leu Leu Phe Trp Ile Pro
  1               5                  10                  15 gtt tcc gga ggt gat gtt gtg gtg act caa act cca ctc tcc ctg cct    96
Val Ser Gly Gly Asp Val Val Val Thr Gln Thr Pro Leu Ser Leu Pro
             20                  25                  30 gtc agc ttt gga gat caa gtt tct atc tct tgc agg tct agt cag agt   144
Val Ser Phe Gly Asp Gln Val Ser Ile Ser Cys Arg Ser Ser Gln Ser
         35                  40                  45 ctt gca aag agt tat ggg aac acc tat ttg tct tgg tac ctg cac aag   192
Leu Ala Lys Ser Tyr Gly Asn Thr Tyr Leu Ser Trp Tyr Leu His Lys
     50                  55                  60 cct ggc cag tct cca cag ctc ctc atc tat ggg att tcc aac aga ttt   240
Pro Gly Gln Ser Pro Gln Leu Leu Ile Tyr Gly Ile Ser Asn Arg Phe
 65                  70                  75                  80 tct ggg gtg cca gac agg ttc agt ggc agt ggt tca ggg aca gat ttc   288
Ser Gly Val Pro Asp Arg Phe Ser Gly Ser Gly Ser Gly Thr Asp Phe
                 85                  90                  95 aca ctc aag atc agc aca ata aag cct gag gac ttg gga atg tat tac   336
Thr Leu Lys Ile Ser Thr Ile Lys Pro Glu Asp Leu Gly Met Tyr Tyr
            100                 105                 110 tgc tta caa ggt aca cat cag ccg tac acg ttc gga ggg ggg acc aag   384
Cys Leu Gln Gly Thr His Gln Pro Tyr Thr Phe Gly Gly Gly Thr Lys
        115                 120                 125 ctg gaa ata aaa                                                   396
Leu Glu Ile Lys
    130

<210> SEQ ID NO 12
<211> LENGTH: 132
<212> TYPE: PRT
<213> ORGANISM: Unknown
<220> FEATURE:
<223> OTHER INFORMATION: Mouse

<400> SEQUENCE: 12

Met Lys Leu Pro Val Arg Leu Leu Val Leu Leu Leu Phe Trp Ile Pro
  1               5                  10                  15

Val Ser Gly Gly Asp Val Val Val Thr Gln Thr Pro Leu Ser Leu Pro
             20                  25                  30

Val Ser Phe Gly Asp Gln Val Ser Ile Ser Cys Arg Ser Ser Gln Ser
         35                  40                  45

Leu Ala Lys Ser Tyr Gly Asn Thr Tyr Leu Ser Trp Tyr Leu His Lys
     50                  55                  60

Pro Gly Gln Ser Pro Gln Leu Leu Ile Tyr Gly Ile Ser Asn Arg Phe
 65                  70                  75                  80
```

-continued

```
        Ser Gly Val Pro Asp Arg Phe Ser Gly Ser Gly Ser Gly Thr Asp Phe
                        85                  90                  95

Thr Leu Lys Ile Ser Thr Ile Lys Pro Glu Asp Leu Gly Met Tyr Tyr
                    100                 105                 110

Cys Leu Gln Gly Thr His Gln Pro Tyr Thr Phe Gly Gly Gly Thr Lys
                    115                 120                 125

Leu Glu Ile Lys
                130
```

<210> SEQ ID NO 13
<211> LENGTH: 336
<212> TYPE: DNA
<213> ORGANISM: Homo sapiens

<400> SEQUENCE: 13

| | | |
|---|---|---|
| gatattgtga tgactcagtc tccactctcc ctgcccgtca cccctggaga gccggcctcc | 60 |
| atctcctgca ggtctagtca gagcctcctc catagtaatg gatcaaacta tttggattgg | 120 |
| tacctgcaga agccagggca gtctccacag ctcctgatct atttgggttc taatcgggcc | 180 |
| tccggggtcc ctgacaggtt cagtggcagt ggatcaggca cagattttac actgaaaatc | 240 |
| agcagagtgg aggctgagga tgttggggtt tattactgca tgcaagctct accaactcct | 300 |
| cagacgttcg gccaagggac caaggtggaa atcaaa | 336 |

<210> SEQ ID NO 14
<211> LENGTH: 420
<212> TYPE: DNA
<213> ORGANISM: Artificial Sequence
<220> FEATURE:
<223> OTHER INFORMATION: Mouse Act-1 antibody heavy chain variable
      region with a signal peptide sequence
<220> FEATURE:
<221> NAME/KEY: CDS
<222> LOCATION: (1)...(420)

<400> SEQUENCE: 14

```
atg gga tgg agc tgt atc atc ctc ttc ttg gta tca aca gct aca agt       48
Met Gly Trp Ser Cys Ile Ile Leu Phe Leu Val Ser Thr Ala Thr Ser
 1               5                  10                  15 gtc cac tcc cag gtc caa ctg cag cag cct ggg gct gag ctt gtg aag       96
Val His Ser Gln Val Gln Leu Gln Gln Pro Gly Ala Glu Leu Val Lys
             20                  25                  30 cct ggg act tca gtg aag ctg tcc tgc aag ggt tat ggc tac acc ttc      144
Pro Gly Thr Ser Val Lys Leu Ser Cys Lys Gly Tyr Gly Tyr Thr Phe
         35                  40                  45 acc agc tac tgg atg cac tgg gtg aag cag agg cct gga caa ggc ctt      192
Thr Ser Tyr Trp Met His Trp Val Lys Gln Arg Pro Gly Gln Gly Leu
     50                  55                  60 gag tgg atc gga gag att gat cct tct gag agt aat act aac tac aat      240
Glu Trp Ile Gly Glu Ile Asp Pro Ser Glu Ser Asn Thr Asn Tyr Asn
 65                  70                  75                  80 caa aaa ttc aag ggc aag gcc aca ttg act gta gac att tcc tcc agc      288
Gln Lys Phe Lys Gly Lys Ala Thr Leu Thr Val Asp Ile Ser Ser Ser
                 85                  90                  95 aca gcc tac atg cag ctc agc agc ctg aca tct gag gac tct gcg gtc      336
Thr Ala Tyr Met Gln Leu Ser Ser Leu Thr Ser Glu Asp Ser Ala Val
            100                 105                 110 tac tat tgt gca aga ggg ggt tac gac gga tgg gac tat gct att gac      384
Tyr Tyr Cys Ala Arg Gly Gly Tyr Asp Gly Trp Asp Tyr Ala Ile Asp
        115                 120                 125 tac tgg ggt caa ggc acc tca gtc acc gtc tcc tca                      420
Tyr Trp Gly Gln Gly Thr Ser Val Thr Val Ser Ser
    130                 135                 140
```

```
Tyr Trp Gly Gln Gly Thr Ser Val Thr Val Ser Ser
    130                 135                 140

<210> SEQ ID NO 15
<211> LENGTH: 140
<212> TYPE: PRT
<213> ORGANISM: Artificial Sequence
<220> FEATURE:
<223> OTHER INFORMATION: Mouse Act-1 antibody heavy chain variable
      region with a signal peptide sequence

<400> SEQUENCE: 15

Met Gly Trp Ser Cys Ile Ile Leu Phe Leu Val Ser Thr Ala Thr Ser
1               5                   10                  15

Val His Ser Gln Val Gln Leu Gln Gln Pro Gly Ala Glu Leu Val Lys
            20                  25                  30

Pro Gly Thr Ser Val Lys Leu Ser Cys Lys Gly Tyr Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asp Pro Ser Glu Ser Asn Thr Asn Tyr Asn
65                  70                  75                  80

Gln Lys Phe Lys Gly Lys Ala Thr Leu Thr Val Asp Ile Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Ser Val Thr Val Ser Ser
    130                 135                 140

<210> SEQ ID NO 16
<211> LENGTH: 414
<212> TYPE: DNA
<213> ORGANISM: Artificial Sequence
<220> FEATURE:
<223> OTHER INFORMATION: Human 21/28'CL antibody heavy chain variable
      region with a signal peptide sequence
<220> FEATURE:
<221> NAME/KEY: CDS
<222> LOCATION: (1)...(414)

<400> SEQUENCE: 16 atg gag ttt ggg ctg agc tgg ctt ttt ctt gtg gct att tta aaa ggt      48
Met Glu Phe Gly Leu Ser Trp Leu Phe Leu Val Ala Ile Leu Lys Gly
1               5                   10                  15 gtc cag tgt cag gtg cag ctt gtg cag tct ggg gct gag gtg aag aag      96
Val Gln Cys Gln Val Gln Leu Val Gln Ser Gly Ala Glu Val Lys Lys
            20                  25                  30 cct ggg gcc tca gtg aag gtt tcc tgc aag gct tct gga tac acc ttc     144
Pro Gly Ala Ser Val Lys Val Ser Cys Lys Ala Ser Gly Tyr Thr Phe
        35                  40                  45 act agc tat gct atg cat tgg gtg cgc cag gcc ccc gga caa agg ctt     192
Thr Ser Tyr Ala Met His Trp Val Arg Gln Ala Pro Gly Gln Arg Leu
    50                  55                  60 gag tgg atg gga tgg atc aac gct ggc aat ggt aac aca aaa tat tca     240
Glu Trp Met Gly Trp Ile Asn Ala Gly Asn Gly Asn Thr Lys Tyr Ser
65                  70                  75                  80 cag aag ttc cag ggc aga gtc acc att acc agg gac aca tcc gcg agc     288
Gln Lys Phe Gln Gly Arg Val Thr Ile Thr Arg Asp Thr Ser Ala Ser
                85                  90                  95
```

```
aca gcc tac atg gag ctg agc agc ctg aga tct gaa gac acg gct gtg        336
Thr Ala Tyr Met Glu Leu Ser Ser Leu Arg Ser Glu Asp Thr Ala Val
            100                 105                 110 tat tac tgt gcg aga gga ggt tac tat ggt tcg ggg agc aac tac tgg        384
Tyr Tyr Cys Ala Arg Gly Gly Tyr Tyr Gly Ser Gly Ser Asn Tyr Trp
        115                 120                 125 ggc cag gga acc ctg gtc acc gtc tcc tca                                414
Gly Gln Gly Thr Leu Val Thr Val Ser Ser
    130                 135
```

<210> SEQ ID NO 17
<211> LENGTH: 138
<212> TYPE: PRT
<213> ORGANISM: Artificial Sequence
<220> FEATURE:
<223> OTHER INFORMATION: Human 21/28'CL antibody heavy chain variable
      region with a signal peptide sequence

<400> SEQUENCE: 17

```
Met Glu Phe Gly Leu Ser Trp Leu Phe Leu Val Ala Ile Leu Lys Gly
 1               5                  10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Tyr Tyr Gly Ser Gly Ser Asn Tyr Trp
        115                 120                 125

Gly Gln Gly Thr Leu Val Thr Val Ser Ser
    130                 135
```

<210> SEQ ID NO 18
<211> LENGTH: 540
<212> TYPE: DNA
<213> ORGANISM: Artificial Sequence
<220> FEATURE:
<223> OTHER INFORMATION: Portion of humanized Act-1 antibody heavy chain
      with a heavy chain signal peptide sequence
<220> FEATURE:
<221> NAME/KEY: CDS
<222> LOCATION: (1)...(540)

<400> SEQUENCE: 18

```
atg aaa tgc acc tgg gtc att ctc ttc ttg gta tca aca gct aca agt         48
Met Lys Cys Thr Trp Val Ile Leu Phe Leu Val Ser Thr Ala Thr Ser
 1               5                  10                  15 gtc cac tcc cag gtc caa cta gtg cag tct ggg gct gag gtt aag aag         96
Val His Ser Gln Val Gln Leu Val Gln Ser Gly Ala Glu Val Lys Lys
            20                  25                  30 cct ggg gct tca gtg aag gtg tcc tgc aag ggt tct ggc tac acc ttc        144
Pro Gly Ala Ser Val Lys Val Ser Cys Lys Gly Ser Gly Tyr Thr Phe
        35                  40                  45 acc agc tac tgg atg cat tgg gtg agg cag gcg cct ggc caa cgt cta        192
Thr Ser Tyr Trp Met His Trp Val Arg Gln Ala Pro Gly Gln Arg Leu
    50                  55                  60
```

```
gag tgg atc gga gag att gat cct tct gag agt aat act aac tac aat      240
Glu Trp Ile Gly Glu Ile Asp Pro Ser Glu Ser Asn Thr Asn Tyr Asn
 65                  70                  75                  80 caa aaa ttc aag gga cgc gtc aca ttg act gta gac att tcc gct agc      288
Gln Lys Phe Lys Gly Arg Val Thr Leu Thr Val Asp Ile Ser Ala Ser
                 85                  90                  95 aca gcc tac atg gag ctc agc agc ctg aga tct gag gac act gcg gtc      336
Thr Ala Tyr Met Glu Leu Ser Ser Leu Arg Ser Glu Asp Thr Ala Val
            100                 105                 110 tac tat tgt gca aga ggg ggt tac gac gga tgg gac tat gct att gac      384
Tyr Tyr Cys Ala Arg Gly Gly Tyr Asp Gly Trp Asp Tyr Ala Ile Asp
        115                 120                 125 tac tgg ggt caa ggc acc ctg gtc acc gtc tcc tca gcc tcc acc aag      432
Tyr Trp Gly Gln Gly Thr Leu Val Thr Val Ser Ser Ala Ser Thr Lys
    130                 135                 140 ggc cca tcg gtc ttc ccc ctg gca ccc tcc tcc aag agc acc tct ggg      480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg      528
Gly Thr Ala Ala Leu Gly Cys Leu Val Lys Asp Tyr Phe Pro Glu Pro
                165                 170                 175 gtg acg gtg tcg                                                      540
Val Thr Val Ser
            180

<210> SEQ ID NO 19
<211> LENGTH: 180
<212> TYPE: PRT
<213> ORGANISM: Artificial Sequence
<220> FEATURE:
<223> OTHER INFORMATION: Portion of humanized Act-1 antibody heavy chain
      with a heavy chain signal peptide sequence

<400> SEQUENCE: 19

Met Lys Cys Thr Trp Val Ile Leu Phe Leu Val Ser Thr Ala Thr Ser
 1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Gly Ser Gly Tyr Thr Phe
         35                  40                  45

Thr Ser Tyr Trp Met His Trp Val Arg Gln Ala Pro Gly Gln Arg Leu
     50                  55                  60

Glu Trp Ile Gly Glu Ile Asp Pro Ser Glu Ser Asn Thr Asn Tyr Asn
 65                  70                  75                  80

Gln Lys Phe Lys Gly Arg Val Thr Leu Thr Val Asp Ile Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser
            180
```

<210> SEQ ID NO 20
<211> LENGTH: 413
<212> TYPE: DNA
<213> ORGANISM: Artificial Sequence
<220> FEATURE:
<223> OTHER INFORMATION: Portion of humanized Act-1 antibody light chain
     with a light chain signal peptide sequence

<400> SEQUENCE: 20

```
atgaagttgc ctgttaggct gttggtgctt ctgttgttct ggattcctgt tccggaggt      60
gatgttgtga tgactcaaag tccactctcc ctgcctgtca ccctggaga accagcttct     120
atctcttgca ggtctagtca gagtcttgca aagagttatg gaacaccta tttgtcttgg    180
tacctgcaga agcctggcca gtctccacag ctcctcatct atgggatttc aacagattt    240
tctggggtgc cagacaggtt cagtggcagt ggttcaggga cagatttcac actcaagatc   300
cgcgagtag aggctgagga cgtgggagtg tattactgct tacaaggtac acatcagccg    360
tacacgttcg gacagggac caaggtggaa ataaaacggg ctgatgcggc gcc            413
```

<210> SEQ ID NO 21
<211> LENGTH: 138
<212> TYPE: PRT
<213> ORGANISM: Artificial Sequence
<220> FEATURE:
<223> OTHER INFORMATION: Portion of humanized Act-1 antibody light chain
     with a light chain signal peptide sequence

<400> SEQUENCE: 21

```
Met Lys Leu Pro Val Arg Leu Leu Val Leu Leu Phe Trp Ile Pro
  1               5                  10                 15

Val Ser Gly Gly Asp Val Val Met Thr Gln Ser Pro Leu Ser Leu Pro
                 20                 25                 30

Val Thr Pro Gly Glu Pro Ala Ser Ile Ser Cys Arg Ser Ser Gln Ser
             35                 40                 45

Leu Ala Lys Ser Tyr Gly Asn Thr Tyr Leu Ser Trp Tyr Leu Gln Lys
         50                 55                 60

Pro Gly Gln Ser Pro Gln Leu Leu Ile Tyr Gly Ile Ser Asn Arg Phe
 65                 70                 75                 80

Ser Gly Val Pro Asp Arg Phe Ser Gly Ser Gly Ser Gly Thr Asp Phe
                 85                 90                 95

Thr Leu Lys Ile Ser Arg Val Glu Ala Glu Asp Val Gly Val Tyr Tyr
             100                105                110

Cys Leu Gln Gly Thr His Gln Pro Tyr Thr Phe Gly Gln Gly Thr Lys
         115                120                125

Val Glu Ile Lys Arg Ala Asp Ala Ala Pro
     130                135
```

<210> SEQ ID NO 22
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 22

```
tttccggagg tgatgttgtg atgactcaaa gtccactctc cctgcctgtc accctggag     60
aaccagcttc tatctcttgc aggtctagtc agag                                94
```

<210> SEQ ID NO 23
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 23
actggccagg cttctgcagg taccaagaca aataggtgtt cccataactc tttgcaagac    60
tctgactaga cctgcaagag atagaagctg gttc                                94

<210> SEQ ID NO 24
<211> LENGTH: 83
<212> TYPE: DNA
<213> ORGANISM: Artificial Sequence
<220> FEATURE:
<223> OTHER INFORMATION: Synthetic oligonucleotide

<400> SEQUENCE: 24
cctggccagt ctccacagct cctcatctat gggatttcca acagattttc tggggtgcca    60
gacaggttca gtggcagtgg ttc                                            83

<210> SEQ ID NO 25
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 25
actcgcgaga tcttgagtgt gaaatctgtc cctgaaccac tgccactgaa cctgtctggc    60
accccagaaa atctgttgga aatc                                           84

<210> SEQ ID NO 26
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 26
tctcgcgagt agaggctgag gacgtgggag tgtattactg cttacaaggt acacatcagc    60
cgtacac                                                              67

<210> SEQ ID NO 27
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 27
atggcgccgc atcagcccgt tttatttcca ccttggtccc ctgtccgaac gtgtacggct    60
gatgtgtacc ttgtaagcag taatac                                         86

<210> SEQ ID NO 28
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 28

```
ataagcttcg ccatgaaatg cacctgggtc attctcttct tggtatcaac agctacaagt    60
gtccactccc aggtccaact agtgcaccgg tta                                 93

<210> SEQ ID NO 29
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 29
taaccggtgc actagttgga cctgggagtg gacacttgta gctgttgata ccaagaagag    60
aatgacccag gtgcatttca tggcgaagct tat                                 93

<210> SEQ ID NO 30
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 30
caactagtgc agtctggggc tgaggttaag aagcctgggg cttcagtgaa ggtgtcctgc    60
aagggttctg gctacacctt caccagc                                        87

<210> SEQ ID NO 31
<211> LENGTH: 88
<212> TYPE: DNA
<213> ORGANISM: Artificial Sequence
<220> FEATURE:
<223> OTHER INFORMATION: Synthetic oligonucleotide

<400> SEQUENCE: 31
taaccggtac tctagacgtt ggccaggcgc ctgcctcacc caatgcatcc agtagctggt    60
gaaggtgtag ccagaaccct tgcaggac                                       88

<210> SEQ ID NO 32
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 32
cgtctagagt ggatcggaga gattgatcct tctgagagta atactaacta caatcaaaaa    60
ttcaagggac gcgtca                                                    76

<210> SEQ ID NO 33
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 33
taaccggtgt gctagcggaa atgtctacag tcaatgtgac gcgtcccttg aatttttgat    60
tgtagttagt attact                                                    76

<210> SEQ ID NO 34
<211> LENGTH: 88
<212> TYPE: DNA
<213> ORGANISM: Artificial Sequence
```

```
<220> FEATURE:
<223> OTHER INFORMATION: Synthetic oligonucleotide

<400> SEQUENCE: 34
ccgctagcac agcctacatg gagctcagca gcctgagatc tgaggacact gcggtctact    60
attgtgcaag aggggttac gacggatg                                        88

<210> SEQ ID NO 35
<211> LENGTH: 88
<212> TYPE: DNA
<213> ORGANISM: Artificial Sequence
<220> FEATURE:
<223> OTHER INFORMATION: Synthetic oligonucleotide

<400> SEQUENCE: 35
tcaccggtgc ggtgaccagg gtgccttgac cccagtagtc aatagcatag tcccatccgt    60
cgtaaccccc tcttgcacaa tagtagac                                       88

<210> SEQ ID NO 36
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 36
ctggtcaccg tctcctcagc ctccaccaag ggcccatcgg tcttccccct ggcaccctcc    60
tccaagagca cctctggggg cacag                                          85

<210> SEQ ID NO 37
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 37
tcaccggttc ggggaagtag tccttgacca ggcagcccag ggccgctgtg cccccagagg    60
tgctcttgga ggagggtgcc agggg                                          85

<210> SEQ ID NO 38
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 38
ctggccaacg                                                           10

<210> SEQ ID NO 39
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 39
cacattgact gtagacactt ccgctagcac agcc                                34

<210> SEQ ID NO 40
<211> LENGTH: 24
<212> TYPE: DNA
```

-continued

```
<213> ORGANISM: Artificial Sequence
<220> FEATURE:
<223> OTHER INFORMATION: Synthetic oligonucleotide

<400> SEQUENCE: 40
ccggaggtga tgttgtggtg actc                                              24

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
taagcttccg ccatgggatg gagc                                              24

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
ggtgacacta gtgccttgac cccag                                             25

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
taagcttccg ccatgaagtt gcct                                              24

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
ggcgccgcat cagcccgttt t                                                 21

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cggcgccatc tgtcttcatc                                                   20

<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 46
aagcttctaa cactctcc                                                     18
```

```
<210> SEQ ID NO 47
<211> LENGTH: 19
<212> TYPE: PRT
<213> ORGANISM: Unknown
<220> FEATURE:
<223> OTHER INFORMATION: Mouse

<400> SEQUENCE: 47

Asp Val Val Val Thr Gln Thr Pro Leu Ser Leu Pro Val Ser Phe Asp
1               5                   10                  15
Gly Gln Val

<210> SEQ ID NO 48
<211> LENGTH: 11
<212> TYPE: PRT
<213> ORGANISM: Unknown
<220> FEATURE:
<223> OTHER INFORMATION: Mouse

<400> SEQUENCE: 48

Asp Val Val Val Thr Gln Thr Pro Leu Ser Leu
1               5                   10

<210> SEQ ID NO 49
<211> LENGTH: 8
<212> TYPE: PRT
<213> ORGANISM: Unknown
<220> FEATURE:
<223> OTHER INFORMATION: Mouse

<400> SEQUENCE: 49

Asp Tyr Ala Ile Asp Tyr Trp Gly
1               5

<210> SEQ ID NO 50
<211> LENGTH: 113
<212> TYPE: PRT
<213> ORGANISM: Artificial Sequence
<220> FEATURE:
<223> OTHER INFORMATION: Mouse consensus sequence

<400> SEQUENCE: 50

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr His Val Pro Pro Tyr Thr Phe Gly Gly Gly Thr Lys Leu Glu Ile
            100                 105                 110
Lys

<210> SEQ ID NO 51
<211> LENGTH: 114
<212> TYPE: PRT
```

```
<213> ORGANISM: Artificial Sequence
<220> FEATURE:
<223> OTHER INFORMATION: Human consensus sequence
<220> FEATURE:
<221> NAME/KEY: UNSURE
<222> LOCATION: (33)...(33)
<223> OTHER INFORMATION: Xaa = Any Amino Acid
<220> FEATURE:
<221> NAME/KEY: UNSURE
<222> LOCATION: (100)...(100)
<223> OTHER INFORMATION: Xaa = Any Amino Acid
<220> FEATURE:
<221> NAME/KEY: UNSURE
<222> LOCATION: (103)...(103)
<223> OTHER INFORMATION: Xaa = Any Amino Acid

<400> SEQUENCE: 51

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Xaa Asp Gly Asn Asn Tyr Leu Asn Trp Tyr Leu Gln Lys Pro Gly Gln
         35                  40                  45

Ser Pro Gln Leu Leu Ile Tyr Leu Val Ser Asn Arg Ala Ser Gly Val
 50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                 85                  90                  95

Ala Leu Gln Xaa Pro Arg Xaa Thr Phe Gly Gln Gly Thr Lys Val Glu
            100                 105                 110

Ile Lys

<210> SEQ ID NO 52
<211> LENGTH: 112
<212> TYPE: PRT
<213> ORGANISM: Artificial Sequence
<220> FEATURE:
<223> OTHER INFORMATION: Reshaped humanized sequence

<400> SEQUENCE: 52

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Ala Lys Ser
             20                  25                  30

Tyr Gly Asn Thr Tyr Leu Ser Trp Tyr Leu Gln Lys Pro Gly Gln Ser
         35                  40                  45

Pro Gln Leu Leu Ile Tyr Gly Ile Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                 85                  90                  95

Thr His Gln Pro Tyr Thr Phe Gly Gln Gly Thr Lys Val Glu Ile Lys
            100                 105                 110

<210> SEQ ID NO 53
<211> LENGTH: 127
<212> TYPE: PRT
<213> ORGANISM: Artificial Sequence
<220> FEATURE:
<223> OTHER INFORMATION: Mouse consensus sequence
```

```
<220> FEATURE:
<221> NAME/KEY: UNSURE
<222> LOCATION: (106)...(107)
<223> OTHER INFORMATION: Xaa = Any Amino Acid
<220> FEATURE:
<221> NAME/KEY: UNSURE
<222> LOCATION: (110)...(110)
<223> OTHER INFORMATION: Xaa = Any Amino Acid

<400> SEQUENCE: 53

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Arg Ile Asp Pro Asn Ser Gly Gly Thr Asn Tyr Asn Glu Lys Phe
     50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
             85                  90                  95

Ala Arg Tyr Tyr Tyr Gly Gly Ser Ser Xaa Xaa Val Tyr Xaa Tyr Trp
            100                 105                 110

Tyr Phe Asp Tyr Trp Gly Gln Gly Thr Thr Val Thr Val Ser Ser
            115                 120                 125

<210> SEQ ID NO 54
<211> LENGTH: 129
<212> TYPE: PRT
<213> ORGANISM: Artificial Sequence
<220> FEATURE:
<223> OTHER INFORMATION: Human consensus sequence
<220> FEATURE:
<221> NAME/KEY: UNSURE
<222> LOCATION: (115)...(115)
<223> OTHER INFORMATION: Xaa = Any Amino Acid

<400> SEQUENCE: 54

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Ala Ile Ser Trp Val Arg Gln Ala Pro Gly Gln Gly Leu Glu Trp Met
         35                  40                  45

Gly Trp Ile Asn Pro Tyr Gly Asn Gly Asp Thr Asn Tyr Ala Gln Lys
     50                  55                  60

Phe Gln Gly Arg Val Thr Ile Thr Ala Asp Thr Ser Thr Ser Thr Ala
 65                  70                  75                  80

Tyr Met Glu Leu Ser Ser Leu Arg Ser Glu Asp Thr Ala Val Tyr Tyr
             85                  90                  95

Cys Ala Arg Ala Pro Gly Tyr Gly Ser Gly Gly Cys Tyr Arg Gly
            100                 105                 110

Asp Tyr Xaa Phe Asp Tyr Trp Gly Gln Gly Thr Leu Val Thr Val Ser
            115                 120                 125

Ser

<210> SEQ ID NO 55
<211> LENGTH: 121
<212> TYPE: PRT
```

<213> ORGANISM: Artificial Sequence
<220> FEATURE:
<223> OTHER INFORMATION: Reshaped humanized sequence

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asp Pro Ser Glu Ser Asn Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Trp Asp Tyr Ala Ile Asp Tyr Trp Gly
            100                 105                 110

Gln Gly Thr Leu Val Thr Val Ser Ser
        115                 120

<210> SEQ ID NO 56
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (30)...(30)
<223> OTHER INFORMATION: n = I

<400> SEQUENCE: 56
cccaagcttc cagggrccar kggataracn grtgg                              35

<210> SEQ ID NO 57
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 57
cccaagctta cgaggggggaa gacatttggg aa                                32

<210> SEQ ID NO 58
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 58
gggaattcat graatgsasc tgggtywtyc tctt                               34

<210> SEQ ID NO 59
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 59

```
actagtcgac atgaagwtgt ggbtraactg grt                                    33

<210> SEQ ID NO 60
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 60
cccaagctta ctggatggtg ggaagatgga                                        30

<210> SEQ ID NO 61
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 61
actagtcgac atggatttwc argtgcagat twtcagctt                              39

<210> SEQ ID NO 62
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 62
ggaagcttcc accatggatt tcggactggc cc                                     32

<210> SEQ ID NO 63
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 63
ggactagtgg tttggacgag cctgttg                                           27

<210> SEQ ID NO 64
<211> LENGTH: 396
<212> TYPE: DNA
<213> ORGANISM: Unknown
<220> FEATURE:
<223> OTHER INFORMATION: Mouse

<400> SEQUENCE: 64
ttttatttcc agcttggtcc ccctccgaa cgtgtacggc tgatgtgtac cttgtaagca        60
gtaatacatt cccaagtcct caggctttat tgtgctgatc ttgagtgtga aatctgtccc      120
tgaaccactg ccactgaacc tgtctggcac cccagaaaat ctgttggaaa tcccatagat      180
gaggagctgt ggagactggc caggcttgtg caggtaccaa dacaaatagg tgttcccata      240
actctttgca agactctgac tagacctgca agagatagaa acttgatctc caaagctgac      300
aggcagggag agtggagttt gagtcaccac aacatcacct ccggaaacag gaatccagaa      360
caacagaagc accaacagcc taacaggcaa cttcat                                396

<210> SEQ ID NO 65
<211> LENGTH: 336
<212> TYPE: DNA
```

```
<213> ORGANISM: Homo sapiens

<400> SEQUENCE: 65
tttgatttcc accttggtcc cttggccgaa cgtctgagga gttggtagag cttgcatgca      60
gtaataaacc ccaacatcct cagcctccac tctgctgatt ttctgtgtaa aatctgtgcc     120
tgatccactg ccactgaacc tgtcagggac cccggaggcc cgattagaac caaatagat     180 caggagctgt ggagactgcc ctggcttctg caggtaccaa tccaaatagt ttgatccatt    240
actatggagg aggctctgac tagacctgca ggagatggag gccggctctc caggggtgac    300
gggcagggag agtggagact gagtcatcac aatatc                              336

<210> SEQ ID NO 66
<211> LENGTH: 420
<212> TYPE: DNA
<213> ORGANISM: Artificial Sequence
<220> FEATURE:
<223> OTHER INFORMATION: Mouse Act-1 antibody heavy chain variable
      region with a signal peptide sequence-antisense

<400> SEQUENCE: 66
tgaggagacg gtgactgagg tgccttgacc ccagtagtca atagcatagt cccatccgtc      60
gtaaccccct cttgcacaat agtagaccgc agagtcctca gatgtcaggc tgctgagctg     120
catgtaggct gtgctggagg aaatgtctac agtcaatgtg gccttgccct tgaattttg     180 attgtagtta gtattactct cagaaggatc aatctctccg atccactcaa ggccttgtcc    240
aggcctctgc ttcacccagt gcatccagta gctggtgaag gtgtagccat aacccttgca    300
ggacagcttc actgaagtcc caggcttcac aagctcagcc ccaggctgct gcagttggac    360
ctgggagtgg acacttgtag ctgttgatac caagaagagg atgatacagc tccatcccat    420

<210> SEQ ID NO 67
<211> LENGTH: 414
<212> TYPE: DNA
<213> ORGANISM: Artificial Sequence
<220> FEATURE:
<223> OTHER INFORMATION: Human 21/28'CL antibody heavy chain variable
      region with a signal peptide sequence-antisense

<400> SEQUENCE: 67
tgaggagacg gtgaccaggg ttccctggcc ccagtagttg ctccccgaac catagtaacc      60
tcctctcgca cagtaataca cagccgtgtc ttcagatctc aggctgctca gctccatgta    120
ggctgtgctc gcggatgtgt ccctggtaat ggtgactctg ccctggaact tctgtgaata    180
ttttgtgtta ccattgccag cgttgatcca tcccatccac tcaagccttt gtccggggc     240 ctggcgcacc caatgcatag catagctagt gaaggtgtat ccagaagcct tgcaggaaac    300
cttcactgag gccccaggct tcttcacctc agcccagac tgcacaagct gcacctgaca     360
ctggacacct tttaaaatag ccacaagaaa aagccagctc agcccaaact ccat          414
```